US006287304B1

(12) United States Patent
Eggers et al.

(10) Patent No.: US 6,287,304 B1
(45) Date of Patent: Sep. 11, 2001

(54) INTERSTITIAL CAUTERIZATION OF TISSUE VOLUMES WITH ELECTROSURGICALLY DEPLOYED ELECTRODES

(75) Inventors: Philip E. Eggers, Dublin; Eric A. Eggers, Columbus; Andrew R. Eggers, Ostrander, all of OH (US)

(73) Assignee: Neothermia Corporation, Columbus, OH (US)

( * ) Notice: Subject to any disclaimer, the term of this patent is extended or adjusted under 35 U.S.C. 154(b) by 0 days.

(21) Appl. No.: 09/419,663

(22) Filed: Oct. 15, 1999

(51) Int. Cl.[7] .................................................. A61B 18/18

(52) U.S. Cl. .................. 606/37; 606/47; 606/45; 606/50

(58) Field of Search ........................... 606/37–41, 45–50

(56) References Cited

U.S. PATENT DOCUMENTS

| 1,813,902 | 7/1931 | Bovie . |
| 3,910,279 | 10/1975 | Okada et al. . |
| 3,955,578 | 5/1976 | Chamness et al. . |
| 4,016,886 | 4/1977 | Doss et al. . |
| 4,116,198 | 9/1978 | Roos . |
| 4,121,592 | 10/1978 | Whalley . |
| 4,140,109 | 2/1979 | Savic et al. . |
| 4,520,249 | 5/1985 | Czerlinski . |
| 4,638,802 | 1/1987 | Okada . |
| 4,658,836 | 4/1987 | Turner . |
| 4,679,561 | 7/1987 | Doss . |
| 4,737,628 | 4/1988 | Lovoi . |
| 4,776,334 | 10/1988 | Prionas . |
| 4,821,725 | 4/1989 | Azam et al. . |
| 4,846,196 | 7/1989 | Wiksell et al. . |
| 4,860,744 | 8/1989 | Johnson et al. . |
| 4,869,247 | 9/1989 | Howard, III et al. . |
| 4,872,458 | 10/1989 | Kanehira et al. . |
| 4,919,138 | 4/1990 | Nordenstroom . |
| 4,920,978 | 5/1990 | Colvin . |
| 4,945,912 | 8/1990 | Langberg . |
| 4,979,518 | 12/1990 | Itoh et al. . |
| 5,057,107 | 10/1991 | Parins et al. . |
| 5,069,223 | 12/1991 | McRae . |
| 5,080,660 | 1/1992 | Buelna . |
| 5,122,137 | 6/1992 | Lennox . |
| 5,125,928 | 6/1992 | Parins et al. . |
| 5,163,938 | 11/1992 | Kambara et al. . |

(List continued on next page.)

FOREIGN PATENT DOCUMENTS

| 195 28 440 A1 | 2/1995 | (DE) . |
| 472 368 B1 | 6/1995 | (EP) . |
| 0 829 232 A3 | 3/1998 | (EP) . |

(List continued on next page.)

OTHER PUBLICATIONS

Zlotta AR, Diavan B, Malos C, Noel JC, Peny MO, Silverman DE, Marberger M, Schulman CC. "Percutaneous transperineal radiofrequency ablation of prostate tumor: safety, feasibility, and pathological effects on human prostate cancer." *British Journal of Urology* 1988; 81 (2): 265–267.

(List continued on next page.)

*Primary Examiner*—Michael Peffley
(74) *Attorney, Agent, or Firm*—Mueller and Smith, LPA

(57) ABSTRACT

Apparatus system and method for cauterizing a volume of tissue wherein electrode assemblies are deployed from the forward end region of an instrument in conjunction with an electrosurgical cutting activity. Upon deployment to one or more deployed orientations, the electrodes assemblies are made biactive and the cauterization of tissue is carried out in a bipolar fashion. Following the procedure, the electrode assemblies are retracted toward the instrument and the instrument is withdrawn from the tissue region.

107 Claims, 22 Drawing Sheets

U.S. PATENT DOCUMENTS

| | | |
|---|---|---|
| 5,192,280 | 3/1993 | Parins . |
| 5,224,488 | 7/1993 | Neuffer . |
| 5,251,645 | 10/1993 | Fenn . |
| 5,282,799 | 2/1994 | Rydell . |
| 5,284,144 | 2/1994 | Delannoy et al. . |
| 5,324,288 | 6/1994 | Billings et al. . |
| 5,330,470 | 7/1994 | Hagen . |
| 5,336,227 | 8/1994 | Nakao et al. . |
| 5,370,675 | 12/1994 | Edwards et al. . |
| 5,385,544 | 1/1995 | Edwards et al. . |
| 5,403,311 | 4/1995 | Abele et al. . |
| 5,409,453 | 4/1995 | Landquist et al. . |
| 5,415,656 | 5/1995 | Tihon et al. . |
| 5,421,819 | 6/1995 | Edwards et al. . |
| 5,423,809 | 6/1995 | Klicek . |
| 5,435,805 | 7/1995 | Edwards et al. . |
| 5,454,790 | 10/1995 | Dubrul . |
| 5,458,597 | 10/1995 | Edwards et al. . |
| 5,462,521 | 10/1995 | Brucker et al. . |
| 5,470,308 | 11/1995 | Edwards et al. . |
| 5,470,309 | 11/1995 | Edwards et al. . |
| 5,472,441 | 12/1995 | Edwards et al. . |
| 5,486,161 | 1/1996 | Lax et al. . |
| 5,486,182 | 1/1996 | Nakao et al. . |
| 5,507,743 | 4/1996 | Edwards et al. . |
| 5,514,131 | 5/1996 | Edwards et al. . |
| 5,536,240 | 7/1996 | Edwards et al. . |
| 5,536,267 | 7/1996 | Edwards et al. . |
| 5,540,655 | 7/1996 | Edwards et al. . |
| 5,540,681 | 7/1996 | Strul et al. . |
| 5,545,195 | 8/1996 | Lennox et al. . |
| 5,599,345 | 2/1997 | Edwards et al. . |
| 5,599,346 | 2/1997 | Edwards et al. . |
| 5,607,389 | 3/1997 | Edwards et al. . |
| 5,620,481 | 4/1997 | Desai et al. . |
| 5,626,577 | 5/1997 | Harris . |
| 5,630,426 | 5/1997 | Eggers et al. . |
| 5,651,780 | 7/1997 | Jackson et al. . |
| 5,672,173 | 9/1997 | Gough et al. . |
| 5,672,174 | 9/1997 | Gough et al. . |
| 5,683,384 | 11/1997 | Gough et al. . |
| 5,709,224 | 1/1998 | Behl et al. . |
| 5,720,744 | 2/1998 | Eggleston et al. . |
| 5,728,143 | 3/1998 | Gough et al. . |
| 5,741,271 | 4/1998 | Nakao et al. . |
| 5,749,870 | 5/1998 | Gloth et al. . |
| 5,759,187 | 6/1998 | Nakao et al. . |
| 5,766,215 | 6/1998 | Muri et al. . |
| 5,782,840 | 7/1998 | Nakao . |
| 5,810,806 | 9/1998 | Ritchart et al. . |
| 5,817,092 | 10/1998 | Behl . |
| 5,827,276 | 10/1998 | LeVeen et al. . |
| 5,855,576 | 1/1999 | LeVeen et al. . |
| 5,857,982 | 1/1999 | Millman et al. . |
| 5,868,740 | 2/1999 | LeVeen et al. . |
| 5,882,316 | 3/1999 | Chu et al. . |
| 5,925,044 | 7/1999 | Hofmann et al. . |
| 5,957,923 | 9/1999 | Hahnen et al. . |
| 6,013,086 | 1/2000 | Ouchi et al. . |
| 6,022,362 | 2/2000 | Lee et al. . |

FOREIGN PATENT DOCUMENTS

| | | |
|---|---|---|
| 829232 | 3/1998 | (EP) . |
| 0 908 156 A1 | 4/1999 | (EP) . |
| 2275226 | 1/1976 | (FR) . |
| 2 311 468 A | 1/1997 | (GB) . |
| 1.004723 | 8/1998 | (NL) . |
| 1235497 | 4/1984 | (SU) . |
| 1355226 | 12/1985 | (SU) . |
| WO92/20291 | 11/1992 | (WO) . |
| WO 95/02371 | 1/1995 | (WO) . |
| WO 95/02730 | 1/1995 | (WO) . |
| WO 96/29946 | 10/1996 | (WO) . |
| WO 97/06739 | 2/1997 | (WO) . |
| WO 97/06740 | 2/1997 | (WO) . |
| WO 97/06855 | 2/1997 | (WO) . |
| WO 97/06857 | 2/1997 | (WO) . |
| WO 97/17029 | 5/1997 | (WO) . |
| WO 97/29702 | 8/1997 | (WO) . |
| WO 97/30642 | 8/1997 | (WO) . |
| WO 97/33524 | 9/1997 | (WO) . |
| WO97/36548 | 10/1997 | (WO) . |
| WO98/08441 | 3/1998 | (WO) . |
| WO 99/44506 | 9/1999 | (WO) . |
| WO99/04704 | 9/1999 | (WO) . |
| WO99/43262 | 9/1999 | (WO) . |
| WO99/53851 | 10/1999 | (WO) . |

OTHER PUBLICATIONS

Ferris IDG, Hainer BL, Pfenninger JL, Zuber TJ, Dewitt DE, Line RL. "Electrosurgical loop excision of the cervical transformation zone: the experience of family physicians." *Journal of Family Practice* 1995; 41 (4): 337–344.

Mor–Yosef S, Lopes A, Pearson S, Monaghan JM. "Loop diathermy cone biopsy." *Obstetrics and Gynecology* 1990P 75 (5): 884–886.

Allgier HP, Deibert P, Zuber 1, Olschewski M, Blum HE. "Percutaneous radiofrequency interstitial thermal abation of small hepatocellular carcinoma." *Lancet* 1999; 353: 1676.

Birdwell RL, Jeffrey SS, Kermit EL, Ikeda DM, Nowels KW. "Preliminary Experience with Intraoperative Radiofrequency Breast Tumor Ablation." *Radiology* 1998; 209 (P): 198.

Djavan B, Motta AR, Susani M, Heinz G, Shariat S, Silverman DE, Schulman CC Marberger M. "Transperineal Radiofrequency Interstitial Tumor Ablation of the Prostate: Correlation of Magnetic Resonance Imaging With Histopathologic Examination." *Urology* 1997; 50: 986–993.

Rose DM, Allegra DIP, Bostick PJ, Foshag U, Bilchik AJ. "Radiofrequency Ablation: A Novel Primary Adjunctive Ablative Technique for Hepatic Malignancies." *American Surgeon* 1999; 65: 1009–1014.

Jeffrey SS, et al, Radiofrequency Ablation of Breast Cancer: First Report of Emerging Technology. *Archives of Surgery* 1999; 134: 1064–1068.

Bilchik, AJ, et al. "Radiofrequency Ablation: A minimally Invasive Technique with Multiple Applications." *Cancer Journal Scientific American* 1999; 5: 356–361.

Chang, et al. "Development of a High Performance Multiprobe Cyrosurgical Device," *Biomedical Instrumentation & Technology* Sep./Oct. 1994; 28: 383–390.

Gilbert, et. al. "Temperature Determination in the Frozen Region During Cryosurgery of Rabbit Liver Using MR Image Analysis," *Magnetic Resonance Imaging* Nov. 6, 1997 15: 657–667.

AASLD Abstract *Hepatology* Oct. 1997 p. 240A.

Homasson, et al. "The Operation and Efficay of Cryosurgical, Nitrous Oxide–Driven Cyroprobe," *Cryobiology* 1994; 31: 290–304.

Huang, et al. "Studies on hyperthermic solidification as a supplement to surgical resection in the treatment of 39 advanced cases of liver cancer," *Cancer Letters* 1994: 82: 199–202.

Ireland Cancer Center Achieves Highest National Award and Recognition. University Hospitals of Cleveland Mar. 2, 1998 http://www.prnewswire.com/.

Jolesz, et al. "Interventional Use of Magnetic Resonance Imaging" *Magnetic Resonance Quarterly* 1994; 10:85–96.

Lee, et al. "US–Guided Percutaneous Cryoablation of Prostate Cancer," *Radiology* 1994; 192: 769–776.

Nakagawa, et al. "Comparison of In Vitro Tissue Temperature Profile and Lesion Geometry of Radiofrequency Ablation With a Saline–Irrigated Electrode Versus Temperature Controlling a Canine Thigh Muscle Preparation," *Circulation* Apr. 1995 91: 2264–2273.

Nativ, et al. "Percutaneous ablation of malignant liver tumor in rabbits using low radio frequency energy" *Journal of Experimental Therapeutics & Oncology* 1996; 1: 312–316.

Onik, et al. "Ultrasound–Guided Hepatic Cryosurgery in the Treatment of Metastatic Colon Carcinoma," *Cancer* Feb. 15, 1991; 67: 901–907.

Onik, et al. "Transrectal Ultrasound–Guided Percutaneous Radical Cyrosurgical Ablation of the Prostate," *Cancer* 1993; 72: 1291–9.

Onik, et al. "Percutaneous Transperineal Prostate Cyrosurgery Using Transrectal Ultrasound Guidance: Animal Model," *Urology* Mar. 1991; 27: 277–281.

Polk, et al. "A Technique for the Use of Cryosurgery to Assist Hepatic Resection," *J. Am. Coll. Surg.*, 1995; 180: 171–176.

"Port–Site Recurrence in Cancer Laparoscopy/Why Does it Happen?".

Rabin, et al. "A Compact Cryosurgical Apparatus for Minimally Invasive Procedures," *Biomedical Instrumentation & Technology* May/Jun. 1997; 31: 251–258.

Rewscastle, et al. "Use of a Moratorium To Achieve Consistent Liquid Nitrogen Cyroprobe Performance," *J. Surg. Oncol.* 1997; 66: 110–113.

Rivoire, et al. "Hepatic Cryosurgery Precision: Evaluation of Ultrasonography, Thermometry, and Impedancemetry in a Pig Model," *J. of Surg. Oncol.* 1996; 61: 242–248.

Sall, et al. "Prostatic Urethral Strictures After Transurethral Microwave Thermal Therapy for Beneign Prostatic Hyperplasia," *Urology* 1997; 50: 983–985.

Shafir, et al. "Cyroablation of Unresectable Malignant Liver Tumors," *Am. J. Surg.* 1996; 171: 27–31.

Schulman, et al. "Radiofrequency Interstitial Tumor Ablation (RITA) of the Prostate: A New Modality of Treatment of Localized Prostate Cancer," Poster Sess. Sep. 1, _; P5–30.

Shinohara, et al. "Cryosurgical Treatment of Localized Prostate Cancer (Stages T1–T4): Preliminary Results," *Journal of Urology* Jul. 1996; 156: 115–121.

Tandan, et al. "Laparoscopic cryosurgery for hepatic tumors," *Surg. Endosc.* 1997; 11: 1115–1117.

Tang, et al. "Spectroscopic Differences Between Human Cancer and Normal Lung and Breast Tissues," *Lasers in Surgery and Medicine* 1989; 9: 290–295.

Weaver, et al. "Hepatic Cryosurgery in Treating Colorectal Metastases," *Cancer* 1995; 76: 210–214.

Welling, et al. "Cyroprobe as a 'Handle' for Resection of Metastatic Liver Tumors," *J. of Surg. Oncol.* 1990; 45: 227–228.

Abstract 1640, The Journal of Urology 1997; 157: 420.

Zhou, et al. "The role of cryosurgery in the treatment of hepatic cancer: a report of 113 cases," *J. Cancer Res. Clin. Oncol.* 1993; 120: 100–102.

Undergrad Research 1997, 25(1).

Zlotta, et al. "Radiofrequency Interstitial Tumor Ablation (RITA) Is a Possible New Modality for Treatment of Renal Cancer: Ex Vito and in Vito Experience," *Journal of Endouology* 1997: 11:251–258.

Zlotta, et al. "Possible Mechanisms of Action of Transurethral Needle Ablation of the Prostate on Benign Prostatic Hyperplasia Symptoms: A Neurohistochemical Study," *Journal of Urology* 1997; 157: 894–899.

Anderson, et al. "Implantation Metastasis After Laparascopic Biopsy of Bladder Cancer," *Journal of Urology* 1995 153: 1047–1048.

Barista, I. "Comments on Current and Future Trends in the Multidisciplinary Approach for High–risk Breast Cancer. The Experience of the Milan Cancer Institute," *European Journal of Cancer* 1997; 33: 164–165.

Baum, M. "Does Surgery Disseminate or Accelerate Cancer?" *The Lancet* 1996; 347: 260.

Bangma, et al. "Cutaneous Metastasis Following Laparoscopic Pelvic Lymphadenectomy for Prostatic Carcinoma," *Journal of Urology* May 1995; 153: 1635–1636.

Berger, et al. "Dissemination of cancer cells by needle biopsy of the lung," *Journal of Thoracic and Cardiovascular Surgery* 1972; 63: 430–432.

Boutin, et al. "Prevention of Malignant Seeding after Invasive Diagnostic Procedures in Patients with Pleural Mesothelioma," *Chest* 1995; 108: 754–758.

Breul, et al. "Implantation Metastasis after a Suprapubic Catheter in a Case of Bladder Cancer," *Eur. Urol.* 1992; 22: 86–88.

Caturelli, et al. "Malignant Seeding after Fine–Needle Aspiration Biopsy of the Pancreas," *Diagn. Imag. Clin. Med.* 1985; 54: 88–91.

Cava, et al. "Subcutaneous metastasis following laparoscopy in gastric adenocarcinoma," *European Journal of Surgical Oncology* 1990; 16: 63–67.

Cedrone, et al. "Neoplastic Seeding Complicating Percutaneous Ethanol Injection for Treatment of Hepatocellular Carcinoma," *Radiology* 1992; 183: 787–788.

Enneking, et al. "The Effect of Inadvertent Tumor Contamination of Wounds During the Surgical Resection of Musculoskeletal Neoplasms," *Cancer* 1988; 62: 1251–1256.

Goletti, et al. "Subcutaneous Seeding after Percutaneous Ethanol Injection of Liver Metastasis," *Radiology* 1992; 183: 785–786.

Grabau, et al. "Needle Biopsy of Brest Cancer. Appearance of tumor cells along the Needle Track," *Case Reports* 192–194.

Harter, et al. "Malignant Seeding of the Needle Track during Stereotaxic Core Needle Breast Biopsy," *Radiology* 1992; 185: 713–714.

Hix, et al. "Needle Aspiration in Lung Cancer: Risk of Tumor Implantation is Not Negligible," *Chest* Mar. 1990; 97: 516–517.

Hsiu, et al. "Tumor Implantation After Diagnostic Laparoscopic Biopsy of Serous Ovarian Tumors of Low Malignant Potential," *Obstet Gynecol* 1986; 68: 90S–93S.

Keate, et al. "Seeding of hepatocellular carcinoma to peritoneoscopy insertion site," *Gastrointestinal Endoscopy* 1992; 38: 203.

Lundstedt, Tumor Seeding Occurring After Fine–Needle Biopsy of Abdominal Malignancies, *Acta Radiological* 1991; 32:518–520. 8

McGrath, et al. "Case Report: Cutaneous Seeding Following Fine Needle Biopsy of Colonic Liver Metastasis," *Clinical Radiology* 1991; 43: 130–131.

Moul, et al. "Risk Factors For Perineal Seeding of Prostate Cancer After Needle Biopsy," *Journal of Urology* 1989 142: 86–88.

Norris, et al. "Neoplastic meningitis following surgical resection of isolated cerebellar metastasis: A potentially preventable complication," *Journal of Neuro–Oncology* 1997; 32: 215–223.

Rosenfeld, et al. "Implantation metastasis of pineoblastoma after stereotactic biopsy," *J neurosurg* 1990; 73: 287–290.

Russi, et al. "Unusual Relapse of Hepatocellular Carcinoma," *Cancer* Sep. 15, 1992; 70: 1483–1487.

Sacchini, et al. "Percutaneous transthoracic needle aspiration biopsy: a case report of implantation metastasis," *European Journal of Surgical Oncology* 1989; 15: 179–183.

Scheele, et al. "Tumor implantation from Needle Biopsy of Hepatic Metastasis," *Hepato–gastrenterol.* 1990; 37: 335–337.

Stockdale, et al. "Abdominal wall metastasis following laparoscopy: a case report," *European Journal of Surgical Oncology* 1985; 11: 373–375.

Terry, John D. "Percutaneous Core Biopsy of the Breast," *Radiology* Aug. 1994; 196: 581–582.

Akiyoshi, F. Koba, et al. "Impaired Production of Interlukin–2 after Surgery," *Clin. Exp. Immunology* 1985; 59: 45–49.

Lennard, T., et al. "The Influence of Surgical Operations on Components of the Human Immune System." *British J. of Surgery* 721985; 72: 771–776.

Neel, H., et al. "Requisites for Successful Cryogenic Surgery of Cancer." *Arch. Surg.* 1971; 102: 45–48.

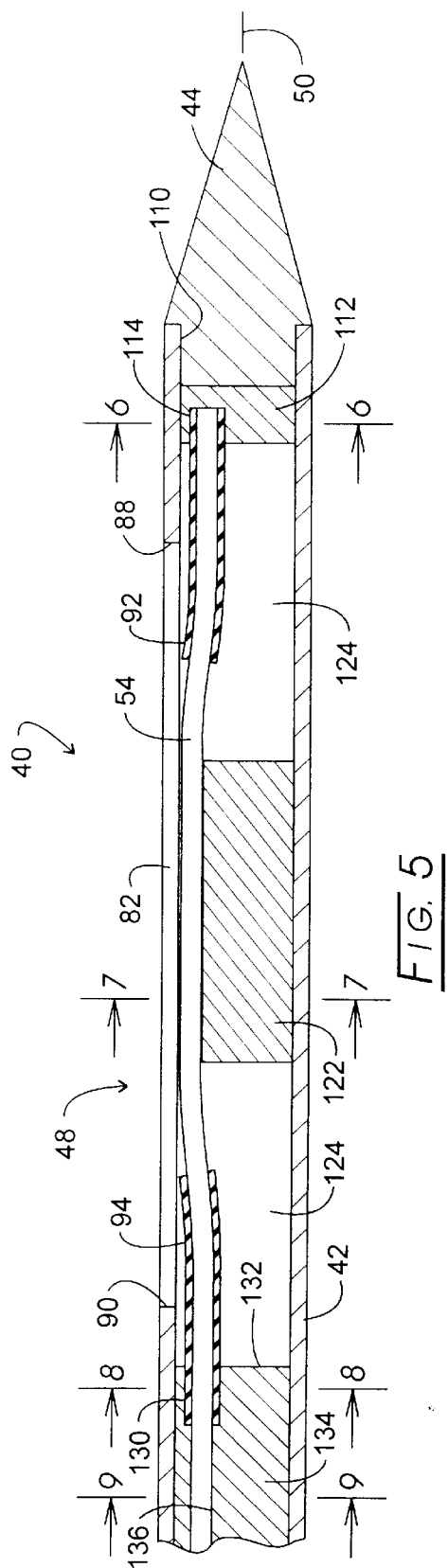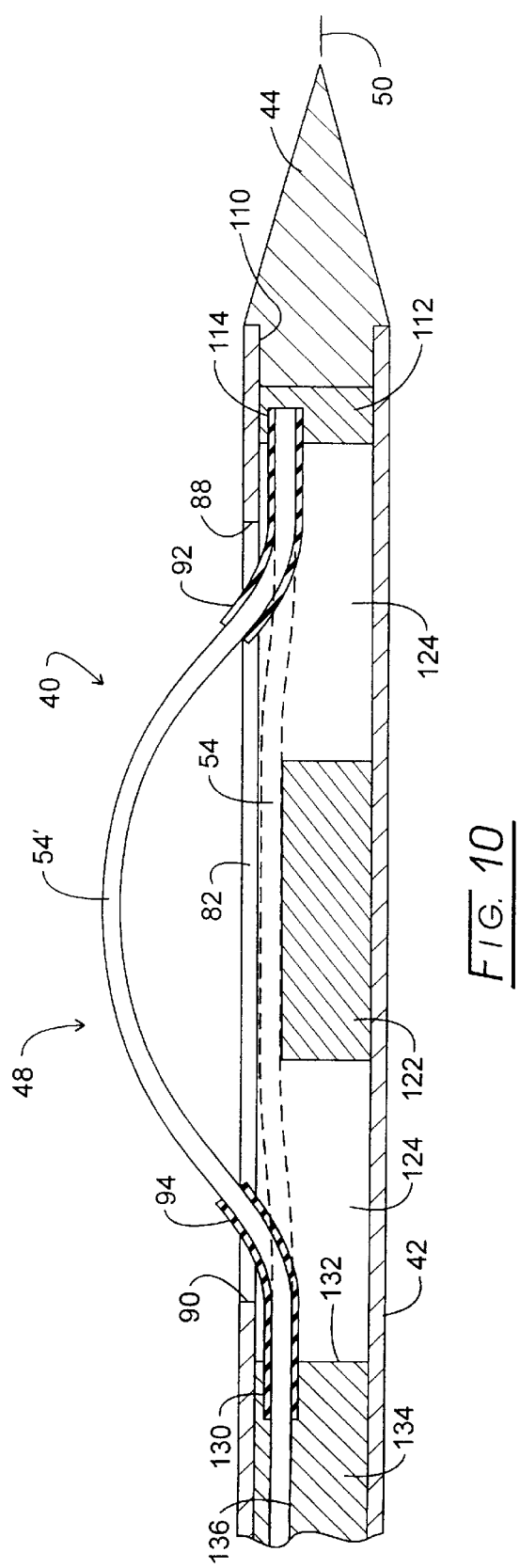

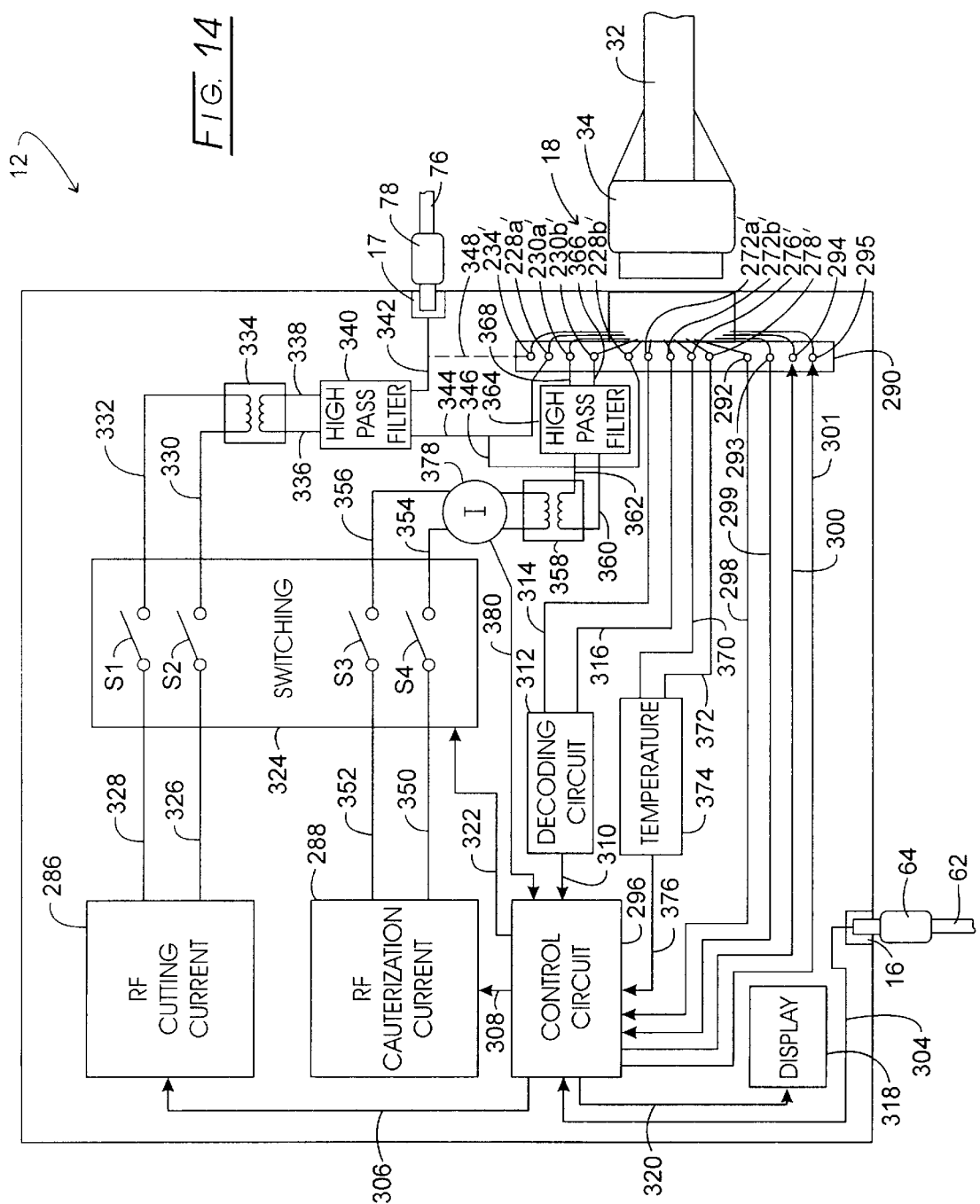

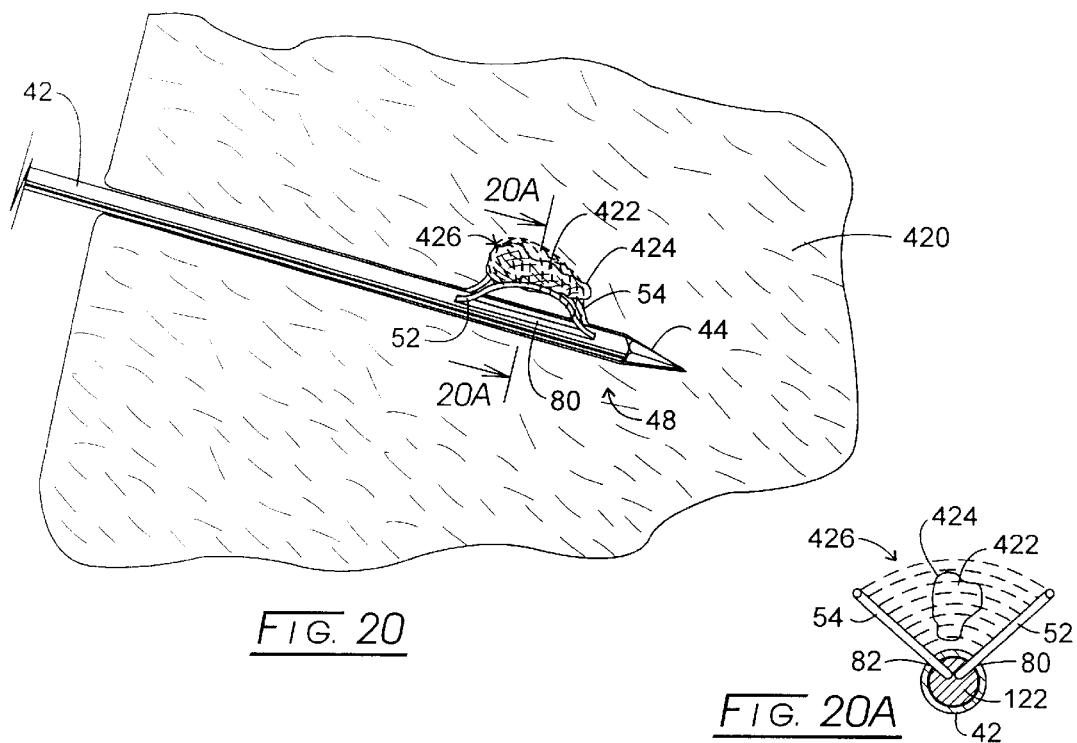
FIG. 20
FIG. 20A
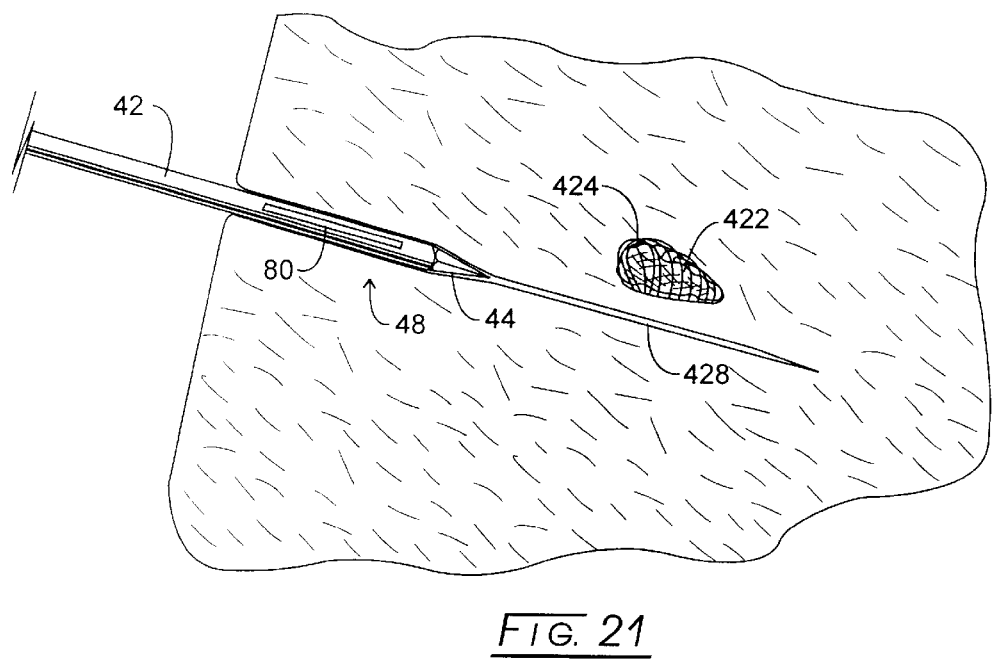
FIG. 21

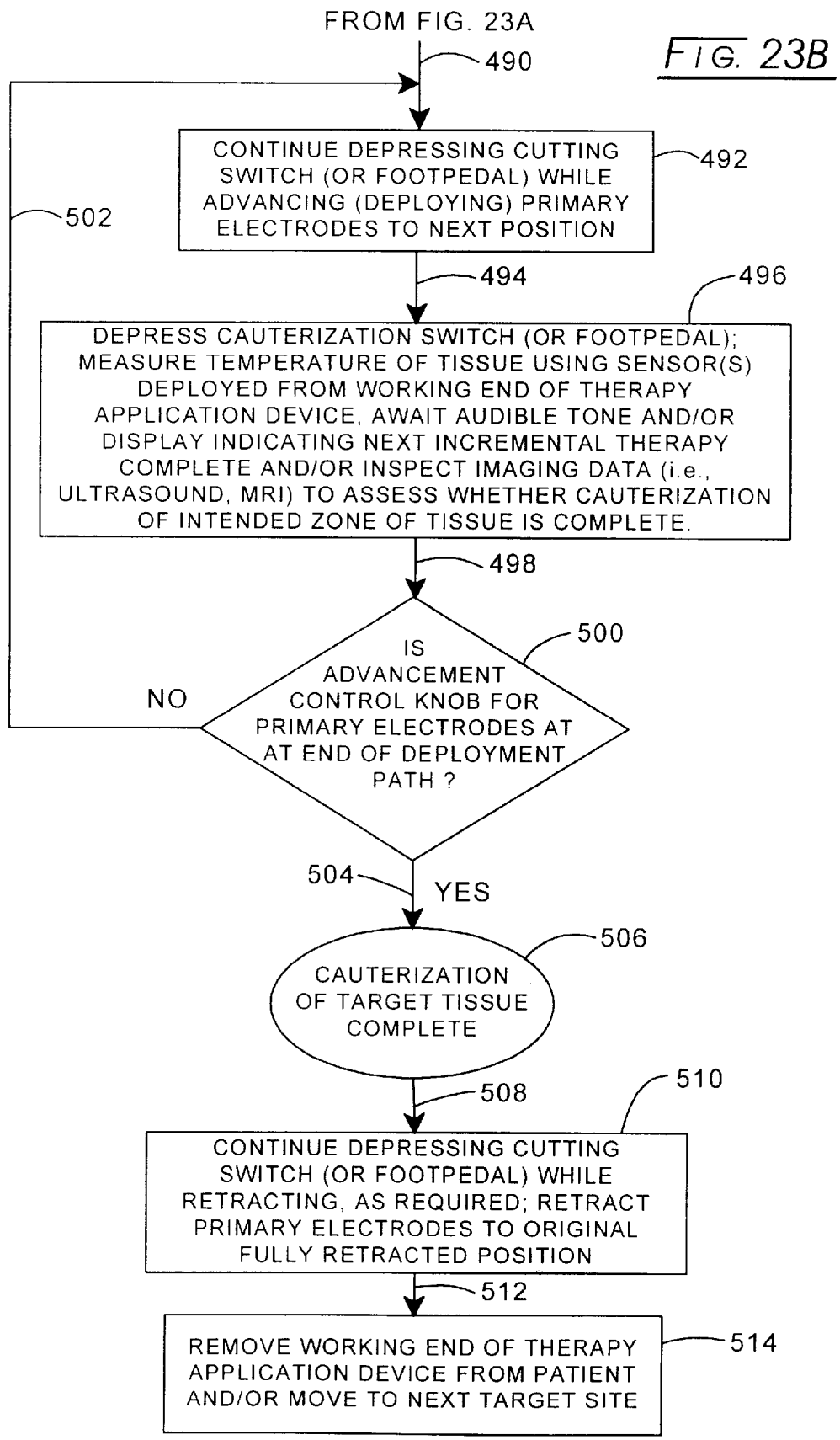

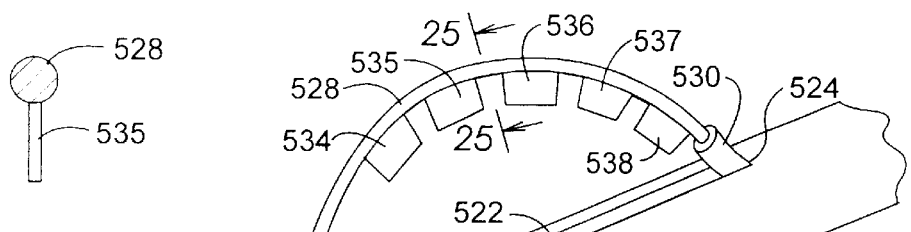
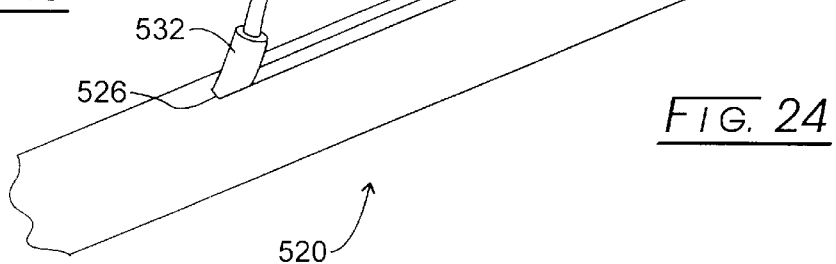
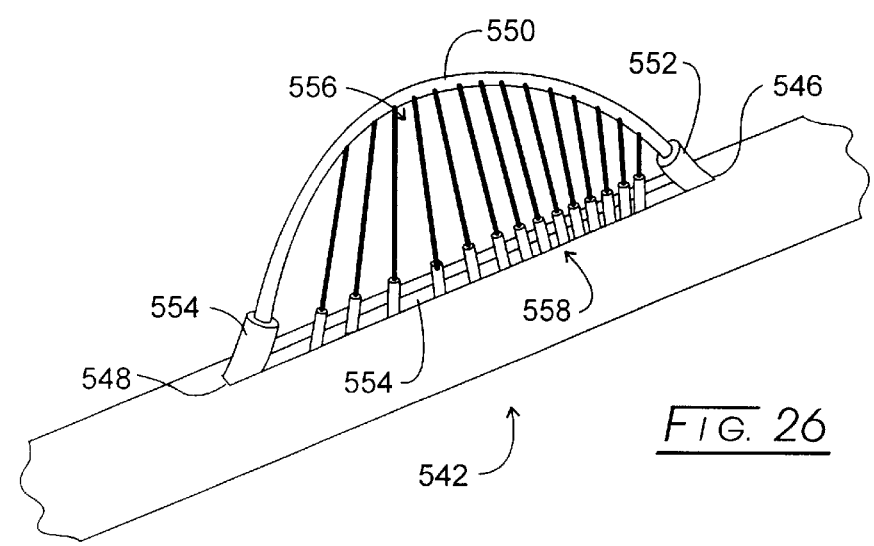
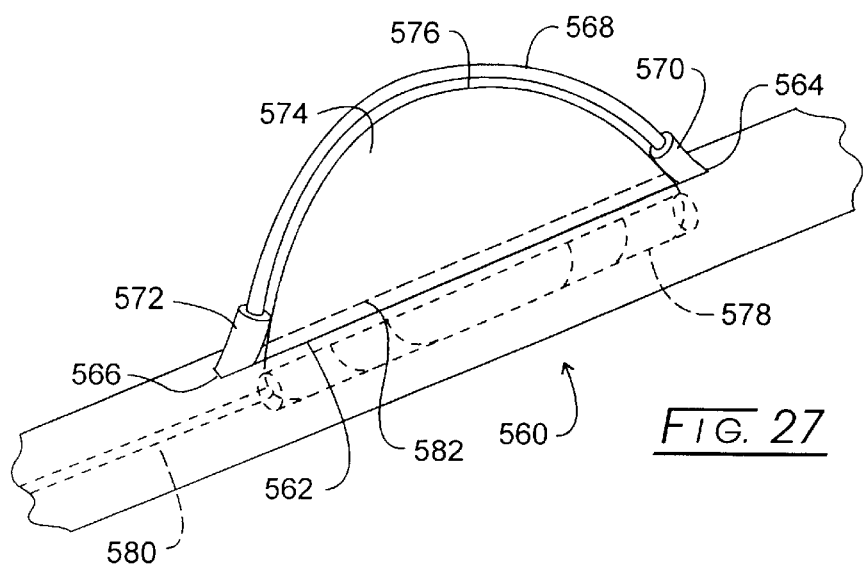

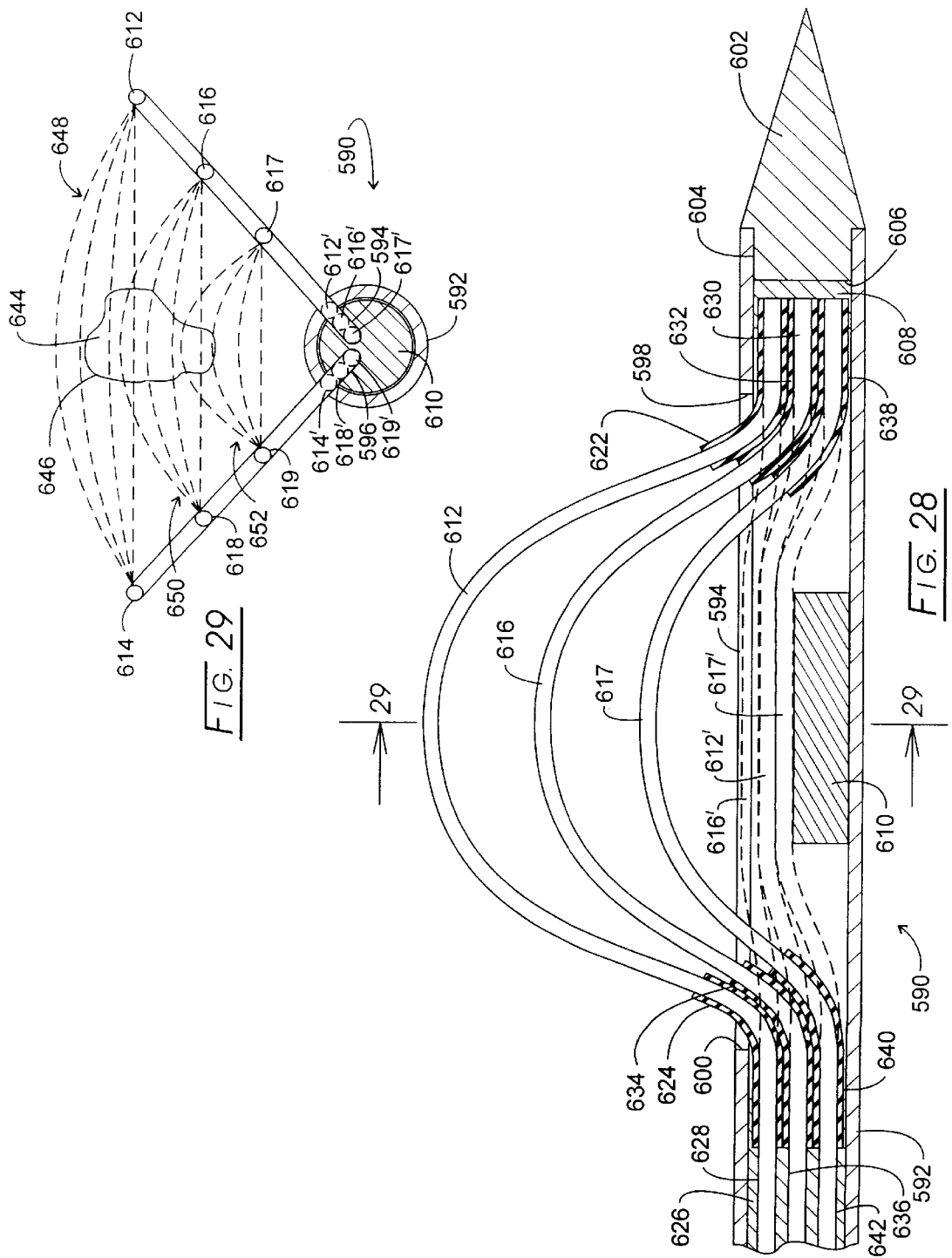

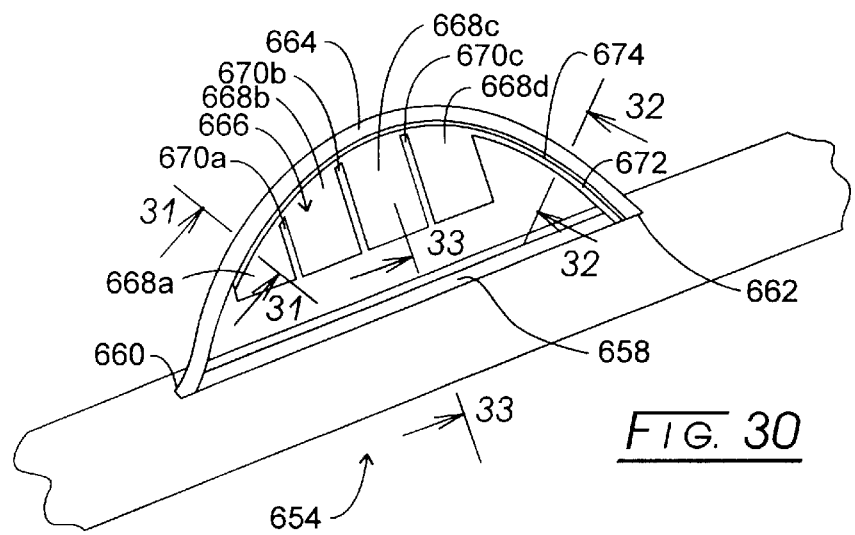
FIG. 30
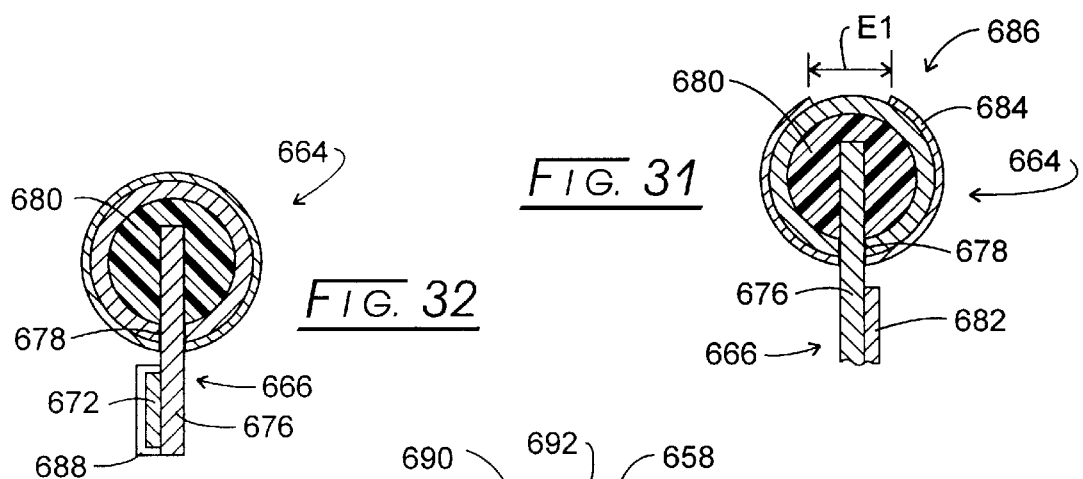
FIG. 32  FIG. 31
FIG. 33
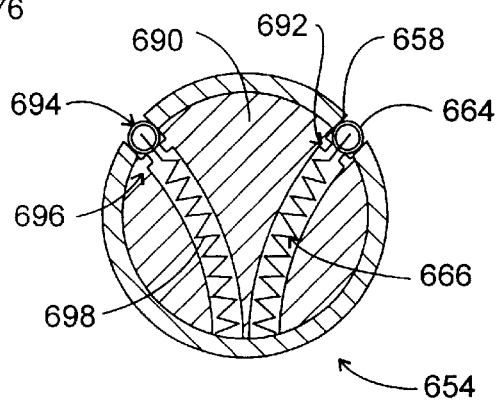
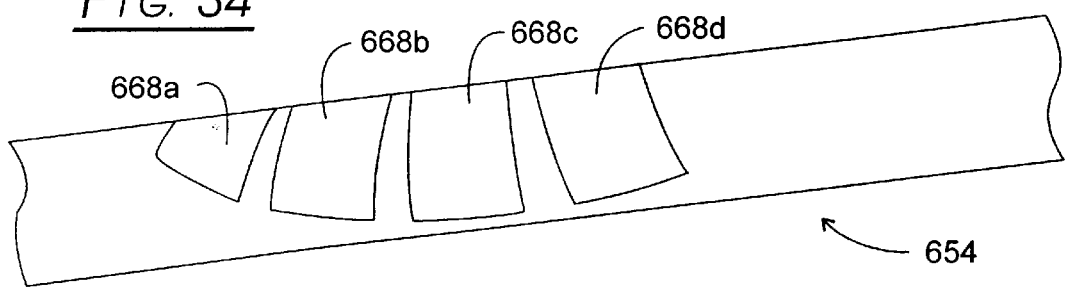
FIG. 34

INTERSTITIAL CAUTERIZATION OF TISSUE VOLUMES WITH ELECTROSURGICALLY DEPLOYED ELECTRODES

CROSS-REFERENCE TO RELATED APPLICATIONS

STATEMENT REGARDING FEDERALLY SPONSORED RESEARCH

Not applicable

BACKGROUND OF THE INVENTION

The excision of diseased or abnormal tissue from the body traditionally has been termed an "invasive" one. In carrying out invasive surgery, medical practitioners generally have resorted to the use of sharpened edge tools and, for about six decades, additionally, forms of electrosurgery. In the latter regard, a somewhat pioneer electrosurgical device was developed by William T. Bovie. This early device, described, for example, in U.S. Pat. No. 1,813,902 issued on Jul. 14, 1931 entitled "Electrosurgical Apparatus" and its successors have met with acceptance over the years within the surgical community to the extent that current versions are referred to as the "Bovie".

For both traditional excision approaches, injury generally occurs to surrounding or peripheral and healthy tissue. While certain of such injuries are apparent, others have been reported which are more subtle. Conventional removal of malignant tumor, as well as more simple biopsy procedures have been reported to generate "seeding", resulting in spreading or metastasizing cancer in the body. In addition to patient discomfort and longer recovery periods, more invasive surgical procedures are reported to be accompanied by a period of immunosuppression, a condition increasing the risk of disease spread. See the following publications in this regard:

"Impaired Production of Interlukin-2 after Surgery," T. Akiyoshi, et al., Clin. Exp. Immunology, Vol. 59, pp 45–49, 1985.

"The Influence of Surgical Operations on Components of the Human Immune System," T. Lennard, et al., British J. of Surgery, Vol. 72, pp 771–776, 1985.

Less invasive alternatives to conventional surgical procedures have been and continue to be investigated, particularly as the clinical detection of tumor or tissue abnormalities has become more refined. For example, current imaging systems (mammography, ultrasonographs, MRI) may detect and locate very small tumor or tissue abnormalities sized at the level of a millimeter. Where such tumor is detected, for example, in the breast, biopsy procedures employing fine needle aspiration techniques may be utilized. Retrospective investigation, however, has determined that about 80% of such biopsied tissue is benign. Where malignancy is determined, the biopsy procedure risks the above-noted seeding or metastasization opportunities. Excision of even the smaller aberrant tissue zones typically is both traumatic to the patient and relatively cost intensive. The latter cost aspect also is present with conventional needle biopsy procedures.

Particularly where small tumors or tissue abnormalities are encountered, investigators have looked to potentially less invasive and thus less costly and less traumatic procedures. For example, if a smaller tumor can be biologically destroyed in situ so as to become ischemic or necrotic, the resultant small zone of dead tissue eventually will be physiologically eliminated by resorption.

One approach to carrying out an in situ destruction of such smaller targeted tissue zones has been to thermally affect the volume of aberrant tissue. Such an approach may involve either cooling or heating the target tissue to the point of irreversible cell death or a necrosis. For the former, cooling approach, reference is made to following publication:

"Requisites for Successful Cryogenic Surgery of Cancer," H. Neel, et al., Arch. Surg., Vol. 102, pp 45–48, 1971.

The latter approach, that of inducing therapeutic hyperthermia, generally is a less invasive one. A rather broad variety of technical modalities have evolved to elevate the temperature of tissue. For example, biological tissue volumes may be heated by inductive, radiant, contact or joulean based techniques. While these hyperthermic approaches exhibit potential advantage over the highly invasive surgical modalities, limitations to their use have been identified. Inductively based systems, certain of which are described in U.S. Pat. Nos. 5,251,645 and 4,679,561 perform by passing high frequency electromagnetic radiation through tissue. This is achieved by passing the radiation between two external electrodes positioned adjacent the patient's skin. A drawback of such an approach to therapeutic hyperthermia resides in the heating of a relatively large volume of tissue at elevated temperatures for extended intervals of time. Typically with this practice, tissue is heated to temperatures of 6° C. to 10° C. above normal body temperature for periods of twenty minutes or more to achieve necrosis. The systems generally do not allow the volume of tissue to be well defined, resulting in either insufficient necrosis or excessive necrosis extending into surrounding healthy tissue. As a consequence, practitioners have looked to combining prolonged heating of tissue with chemotherapy or radiation therapy modalities.

Interstitial thermotherapy has become an important alternative to invasive surgical methods. In general, six thermotherapy modalities have been developed for heating or cooling tissue. They are identified as: (1) radiofrequency heating, (2) microwave heating, (3) laser heating, (4) ultrasound heating and (5) cryogenic cooling. Radiofrequency heating procedures are categorized as direct and indirect. The latter, indirect, approach involves the placement of metal wires or pellets (which may be autoregulated) in the target tissue and then externally applying an R.F. field.

The above six modalities involve either of two methods of temperature alteration in tissue, to wit, conduction and diffuse or distributed heating of targeted tissue. Conduction may be of heat from or to a device or instrument and is characterized as a slow process since thermal diffusion through tissue is a somewhat slow phenomenon. This can lead not only to longer treatment periods but uncertainty in the size and shape of the final lesion. Such conduction-imnited modalities include: indirect radiofrequency heating, laser heating, and cryogenic cooling. Conduction-liited therapeutic heating of tissue using radiant sources is described, for example, in U.S. Pat. Nos. 5,284,144; 4,872, 458; and 4,737,628. Radiant sources, such as lasers, produce localized heating of tissue, but do not permit the affected volume to be predetermined, a pinoni. Other conduction-limited contact heating approaches have been used for inducing therapeutic hyperthermia as are described in U.S. Pat. Nos. 4,979,518; 4,860,744; 4,658,836; and 4,520,249.

Diffuse or distributed heating of targeted tissue is distinctly different from the above-described conduction-limnited method. This approach has the potential advantage that the target tissue can be heated to a desired cauterization temperature within relatively shorter interval of time. Cauterization procedures involve bringing targeted tissue to a temperature within a predetermined temperature range for a duration resulting in irreversible cell death. However, while representing a procedure exhibiting much promise, investigators have encountered obstacles in its implementation. In this regard, the volume of tissue cauterized is generally more difficult to control for systems incorporating microwave or ultrasound procedures, inasmuch as these procedures depend upon the radiation of tissue-heating energy into a volume of tissue from an emitting transducer or antennae system. The precise size of any resulting lesion depends upon the duration of treatment as well as the microwave or ultrasound responsiveness of the targeted tissue. In this regard, investigators have looked to the placement of one or more temperature sensors within the treatment field or have looked to the measurement of electrical impedance to assess the extent of the volume of cauterized tissue to determine an end point termination of the therapy. See in this regard, U.S. Pat. Nos. 5,122,137; 4,776,334; and 4,016,866. A direct measurement of tissue impedance is described, for example, in U.S. Pat. Nos. 5,069,223 and 4,140,109. These procedures are complex and somewhat costly. Of the diffuse or distributed heating approaches, electrosurgical techniques hold promise for both precise and predictable cauterization of targeted tissue volume, as well as a rapidity of the treatment process. Devices and technology representing this category are described, for example, in U.S. Pat. Nos. 5,728,143; 5,683,384; 5,672,173; 5,672,174; 5,599,346; 5,599,345; 5,486,161; 5,472,441; 5,458,597; 5,536,267; 5,507,743; 4,486,196; 4,121,592; and 4,016,886. See also, PCT Application WO 96/29946.

Electrosurgical instruments generally perform in either of two operational modes, monopolar or bipolar. In the monopolar mode, electric current is conducted between a relatively small active electrode and a large return electrode located a distance from the active electrode. Because in the monopolar mode, current density in tissue decreases as the square of the distance from the active electrode, it is more difficult to treat more than very minimal volumes of targeted tissue, as well as to maintain the volumetric accuracy of such treatment. Notwithstanding such a surface related operational limitation, the monopolar devices are quite efficient as electrosurgical cutting tools and for the purpose of carrying out a coagulation at the surface of tissue being cut. Each approach involves a different waveform but both are surface related and involve a modicum of arcing between the instrument tip and the tissue being affected.

The bipolar mode of electrosurgical (Ooulean) heating involves passing current between tissue disposed between two electrodes of similar surface area. To effect cauterization of targeted tissue, this electrosurgical heating technique has been implemented with instruments which deploy pointed, flexible fine wire or needle-like electrode-functioning stylets directly into the targeted tissue. This calls for a mechanical system carrying out tissue penetration with these fine deployed stylets which necessarily will have a small surface area per unit length of the electrode. As a consequence, the permissible current flux flowing between the electrodes is significantly limited inasmuch as excessive current densities will cause desiccation of tissue immediately adjacent the electrodes which defeats the procedure. This follows, inasmuch as the desiccated tissue adjacent the electrode will then exhibit a very high electrical impedance which prevents further tissue heating and thus limits the volume of tissue which can be treated to the point of effective cauterization. For this reason, the fine needle or stylet techniques heretofore employed have been observed to require a treatment duration of ten to fifteen minutes for larger lesions. Further, a temperature monitoring of the fine electrode and even the infusion of conductive fluids is called for to reduce impedance between the electrodes and surrounding tissue. Additionally, practice with the needle extruding mechanisms have shown them to be difficult to deploy, the practitioner having less than desirable information as to the exact positioning of the fine electrode stylets. For example, these wires will deflect in the procedure of insertion into the targeted tissue in dependence upon their degree of flexibility as well as upon the varying density characteristics of abnormal tissue sought to be cauterized. Placement identification or observation procedures using conventional imagining systems is hindered because of the highly diminutive surface area of the electrodes themselves. In this regard, such imagining systems fail to "see" the electrodes. As a consequence, the targeted tissue is either under-treated or the treatment procedure extends cauterization excessively into adjacent healthy tissue, i.e., it encroaches excessively beyond the targeted tissue volume. Bipolar mode electrosurgical procedures are described, for example, in U.S. Pat. Nos. 5,720,744; 5,403,311; 5,122,137; 4,920,978; 4,919, 138; and 4,821,725, while fine needle electrode technologies are set forth, for example, in U.S. Pat. Nos. 5,470,309; 5,370,675; 5,421,819; 5,470,308; and 5,607,389.

BRIEF SUMMARY OF THE INVENTION

The present invention is addressed to system, method and apparatus for carrying out the interstitial cauterization of tissue. Selected in correspondence with the tissue volume subjected to such cauterization, the electrode assemblies employed with the electrosurgical instrumentation of the invention perform in a substantially noninvasive manner, being readily deployed at opposite sides of a targeted tissue volume. This deployment is carried out adjacent to aberrant tissue, such as tumor, thus there is no opportunity for "seeding" where malignancy is present. Deployment is carried out mechanically with primary electrode components using monopolar electrosurgical cutting procedures. Once so deployed the electrode assemblies carry out a biactive cauterization procedure using relatively lower current densities to elevate the temperature of the targeted tissue volume to a level evoking irreversible cell death. In general, the cauterization voltage and current parameters exhibit relatively low crest factor and voltage. To achieve efficient cauterization current densities, the electrode assemblies may utilize a primary electrosurgical component which deploys in an electrosurgical cutting mode with relatively high current density and voltage. Secondary electrodes may be included with the electrode assemblies which are configured with larger surface areas to achieve the lower current densities desired for the subsequent cauterization procedure.

Because the instruments of the invention are called upon to carry out the cauterization of a variation of targeted tissue or tumor sizes, the physical sizes of the electrode assemblies will vary correspondingly. This, in turn, calls for a modulation of the cutting and coagulation electrical parameters developed by an associated electrosurgical generator. In an embodiment of the invention, disposable electrode assemblies and instrument components are configured carrying electrical coding components which are interrogated by the generator at start-up. Such interrogation permits a form of automatic output adjustment on the part of the generator.

In a preferred embodiment, the instrumentation employs a support component with a rigid forward end region which is positioned adjacent the tissue volume to be cauterized. During this insertion mode of operation, two deployable electrode assembly primary components are retained in a non-obtrusive orientation nested within the noted forward end region. Each electrode then is electrosurgically excited in monopolar fashion in electrical association with a remotely disposed patient return electrode. Electrosurgical cutting occurs as the electrodes are deployed mutually angularly outwardly to their cauterization orientations. Such "cutting" of contacted normal peripheral tissue occurs as a consequence of the localized, current-induced vaporization of tissue cell fluids and resultant cell rupture. Each electrode assembly principal component may be fashioned as an elongate resilient structure having a distal end secured adjacent the tip of the instrument and extending along a slot-shaped deployment portion at the forward end region of the instrument. By actuating components within the instrument from a remote base location, each electrode is urged forwardly in compression to form a gradually enlarging arch-shaped structure as electrosurgical cutting ensues. When the cauterization orientation of each electrode assembly is reached, then the control system alters them to a biactive, bipolar form of performance with a cauterization specialized voltage and current. In general, that current will exhibit a low crest factor and will occur at voltages lower than those employed with electrosurgical cutting procedures. Secondary electrodes of relatively larger surface area preferably are deployed with the primary cutting electrode components and excited only with the cauterization specialized voltage and current.

For one technique particularly associated with larger tissue volumes, the deployment of the two electrode assemblies may be in increments from a first cauterization orientation to a last one. At each one of the incremental positions, the deployment is halted and cauterization activity of the electrodes ensues until a portion of the targeted tissue volume is cauterized. Then, the electrode assemblies again are deployed in an electrosurgical cutting mode to a next incremental cauterization orientation and subsequent cauterization takes place. This procedure is reiterated until the last cauterization orientation is reached for completing the cauterization of the entire targeted tissue volume.

Upon completion of the cauterization of the targeted tissue volume to evoke a zone of necrosis, the instrument again is actuated from its base region to withdraw the electrode primary components into their nested orientation within the instrument. This may optionally be carried out by electrosurgically operating the electrodes in a cutting mode during the procedure of their retraction to a nested orientation. Upon retrieval of the electrode assemblies to their non-obtrusive nesting orientation, the instrument may be removed for a next procedure.

In one embodiment of the invention, the forward end region of the instrument, which is in adjacency with the tissue volume cauterized, will contain one or more temperature sensors. Utilizing the temperature condition signal developed in adjacency with the volume of tissue being cauterized, modulation of the current and voltage applied for cauterization may be carried out utilizing temperature thresholding techniques. Additionally, the temperature feature may be employed to automatically determine when the cauterization activity is completed.

The deployed electrode assemblies and rigid forward end components of the instrumentation of the invention may be utilized in conjunction with endoscopic and other forms of delivery systems. In this regard, the instrument may be employed with a common cystoscope to form zones of necrosis within the swollen prostatic tissue encountered with benign prostatic hyperplasia (BPH). To facilitate access to the target tissue site, the support component may be flexible (e.g., constructed using a plastic or plastic/metal matrix such as wire reinforced plastic tubing) to allow bending. Within natural bodily passages (e.g., urethra or urethra to prostate transition, intestine, blood vessel, esophagus). Only the distal portion of the instrument may have a rigid forward end region to effect deployment of electrode assembly primary components and concurrent electrosurgical cutting and/or cauterization of tissue. In the interest of a rapidity of formation of zones of necrosis, the instrument for BPH treatment may be formed having more than two electrodes, for example, four such electrodes which, following their electrosurgical cutting form of deployment, are operated in biactive bipolar fashion to cauterize a zone having an ellipsoidal or spherical region of necrosis.

Other objects of the invention will, in part, be obvious and will, in part, appear hereinafter.

The invention, accordingly, comprises the method, system and apparatus possessing the steps, construction, combination of elements and arrangement of parts which are exemplified in the following detailed disclosure. For a fuller understanding of the nature and objects of the invention, reference should be had to the following detailed description taken in connection with the accompanying drawings.

BRIEF DESCRIMON OF THE DRAWINGS

FIG. 5 is a partial sectional view of the front end region of the cauterization instrument shown in FIG. 1;

FIG. 10 is a sectional view of the front end region shown in FIG. 5 illustrating the deployment of an electrode;

FIG. 14 is an electrical block diagram of a control assembly employed with the invention;

FIG. 20 is a perspective view similar to FIG. 19 but showing current flux density lines evoked during a cauterization procedure;

FIG. 20A is a sectional view taken through the plane 20A—20A shown in FIG. 20;

FIG. 21 is a perspective view showing the withdraw of an instrument according to the invention from tissue following cauterization procedures;

Figure 40:
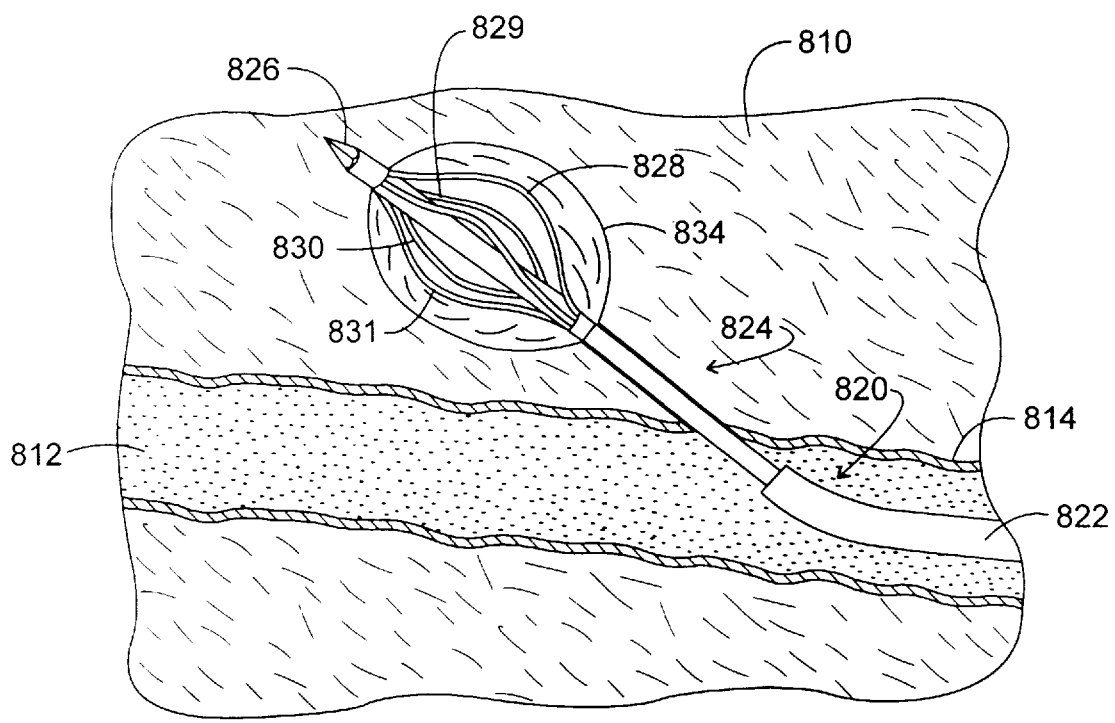
Figure 23A:
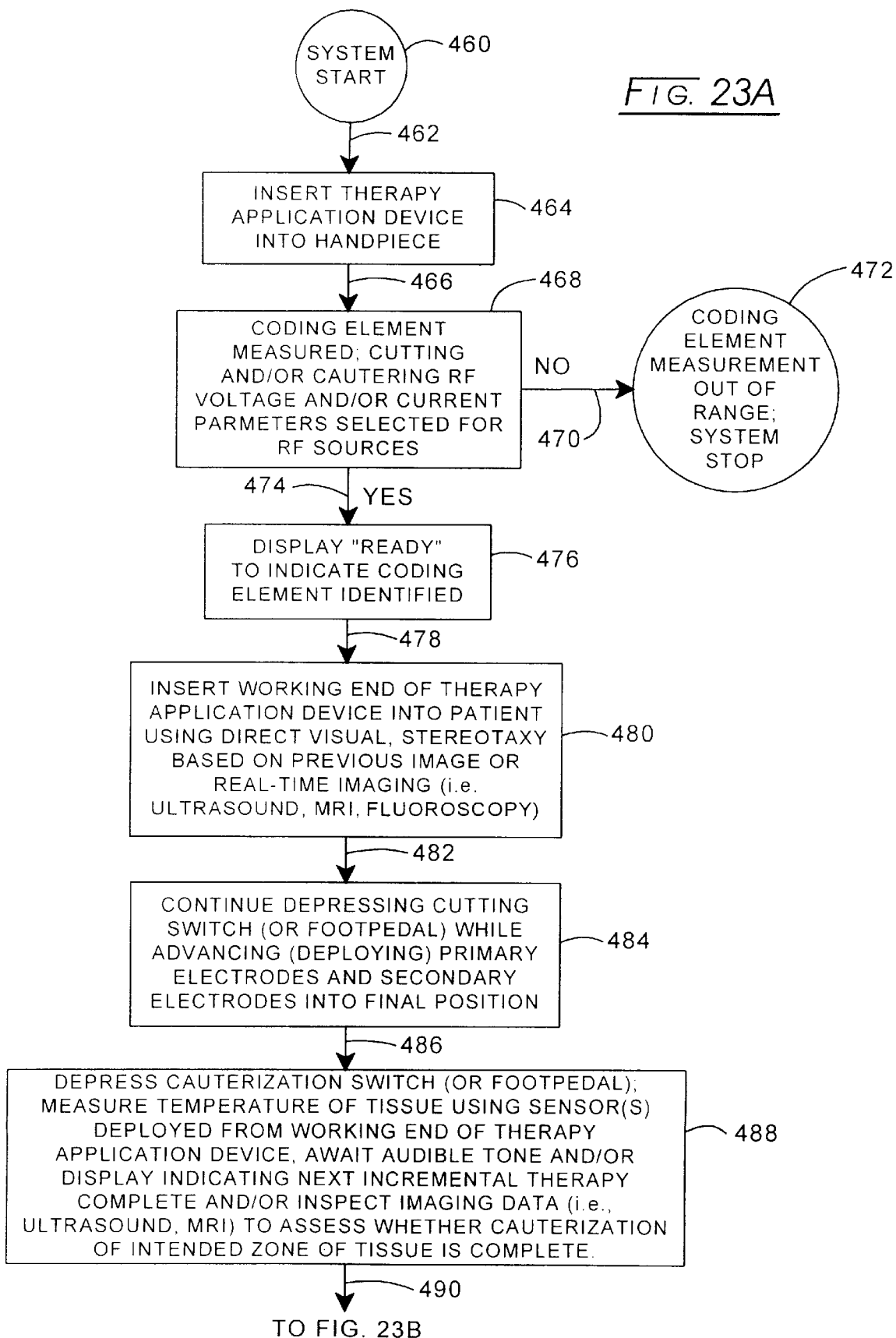
Figure 35:
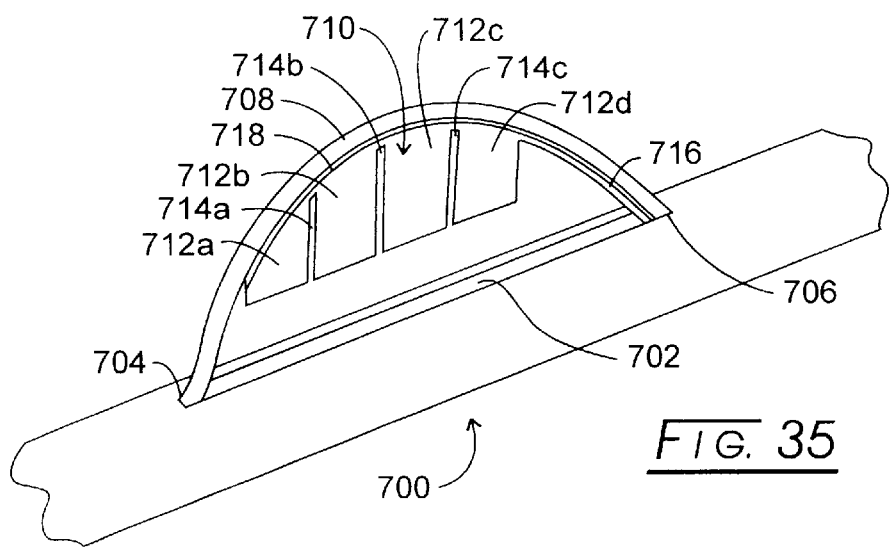
Figure 36:
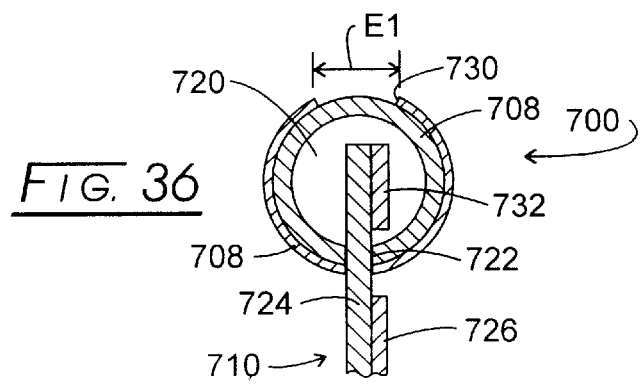
Figure 37:
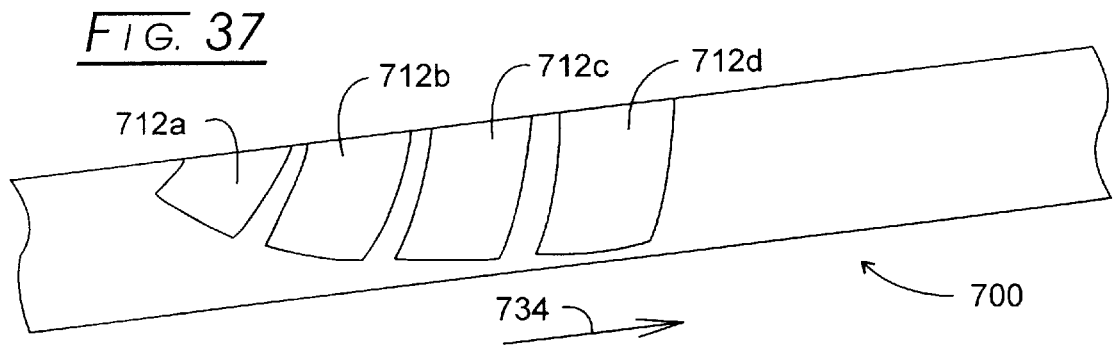
Figures 38, 39:
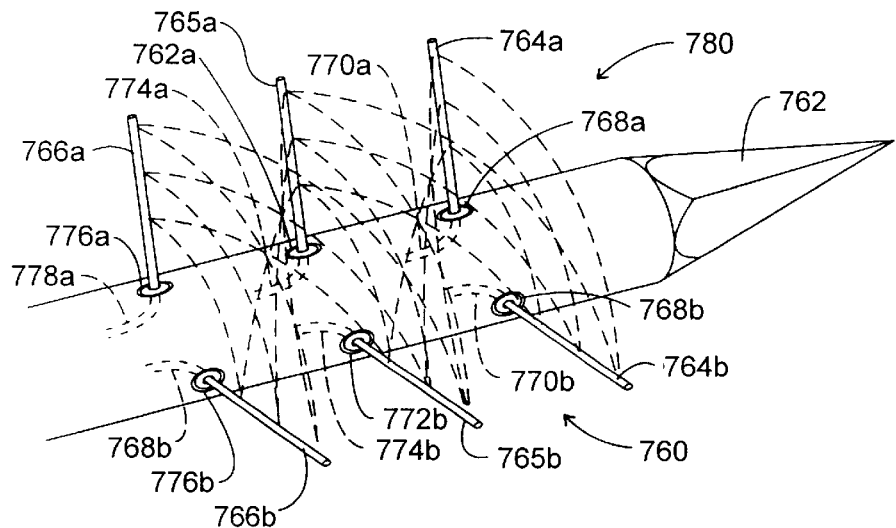
Figure 41:
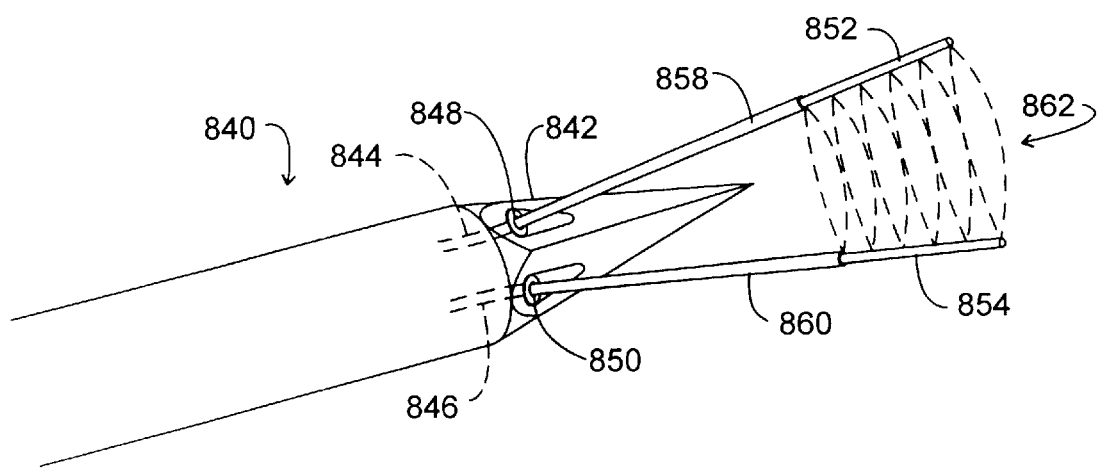
Figure 42:
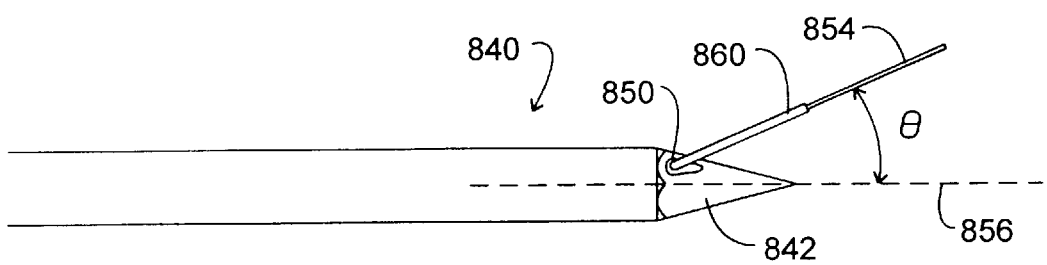

FIGS. 23A and 23B combine as labeled thereon to illustrate a flow chart showing the methodology of the invention;

FIG. 24 is a perspective view of the forward region of an instrument according to the invention wherein secondary electrodes are combined with primary electrode components;

FIG. 25 is a sectional view taken through the plane 25—25 in FIG. 24;

FIG. 26 is a perspective view of the forward end region of an instrument according to the invention showing a deployed arch-type primary electrode and thin elongate secondary electrodes;

FIG. 27 is a pictorial representation of the forward end region of an instrument according to the invention showing an arch form of primary electrode component in combination with a mandrel actuated sheet form of secondary electrode;

FIG. 28 is a partial sectional view of the front end region of an instrument according to the invention showing arch-type secondary electrodes deployed on conjunction with an arch-type primary electrode;

FIG. 29 is a sectional view taken through the plane 29—29 of FIG. 28 and showing current flux paths;

FIG. 30 is a partial perspective view of the forward end region of an instrument showing an electrode assembly with primary and secondary components;

FIG. 31 is a partial sectional view taken through the plane 31—31 in FIG. 30;

FIG. 32 is a partial sectional view taken through the plane 32—32 in FIG. 30;

FIG. 33 is a partial sectional view taken through the plane 33—33 in FIG. 30;

FIG. 34 is a partial pictorial view of a forward region of the instrument of FIG. 30 showing secondary electrode deployment during the removal of the instrument from tissue;

FIG. 35 is a partial pictorial representation of an instrument according to the invention with a primary and secondary electrode assembly;

FIG. 36 is a sectional view taken through the plane 36—36 in FIG. 35;

FIG. 37 is a partial pictorial view of the instrument in FIG. 35 showing the deployment of secondary electrode panels during the removal of the instrument from tissue;

FIG. 38 is a perspective view of the forward end region of an instrument according to the invention showing a multiplicity of substantially straight deployed electrodes;

FIG. 39 is a perspective view of the forward end region of an instrument according to the invention showing an arch form of deployed electrode in combination with a surface mounted electrode;

FIG. 40 is a pictorial illustration of an endoscopic application of an instrument according to the invention showing four deployed electrodes;

FIG. 41 is a partial top view of an instrument according to the invention employing angularity spaced straight electrodes deployed from guide ports and guide channels;

FIG. 42 is a side view of the instrument of FIG. 41.

DETAILED DESCRIPTON OF TBIE INVENTON

The thermotherapy approach of the present invention is one wherein current of a controlled density and waveform is caused to pass through tissue, for example, which may be abnormal such as being formed of malignant cells. Current passage occurs to the extent of necrosis, but without undue damage to healthy surrounding tissue. In this regard, the temperature to which the target tissue is raised will be about 65° C. Because of the interstitial confinement of this tissue volume, immediately adjacent healthy tissue will be heated, but such temperature elevation will be to a maximum temperature which will be in the range of about 41° C. to 45° C. Volume confinement of this thermotherapy is developed through the utilization of an electrosurgical generator which performs in two modes in conjunction with a specialized instrument. The initial one of these modes provides an electrosurgical cutting activity on the part of deploying electrode assemblies of the instrument and the subsequent mode is one carrying out cauterization of the volume of target tissue. In general, it is desirable that the applied voltage utilized for electrosurgical cutting be higher than that employed for the interstitial cauterization procedure. Crest factor, considered to be the peak voltage divided by the RMS voltage for each type of performance, will range from about 1 to 3. Because electrosurgical cutting is used to deploy the electrode assemblies of the instrumentation, the primary electrode components may be of a more robust structure having a larger principal cross-sectional dimension. This enhanced electrode size also contributes to achieving more desired uniform current densities extending into the aberrant or interstitial tissue during the cauterization phase. In a preferred arrangement of the invention, electrosurgical cutting is carried out utilizing a monopolar operation of the electrosurgical generator, while cauterization is carried out in connection with a bipolar mode of performance.

Figure 1:
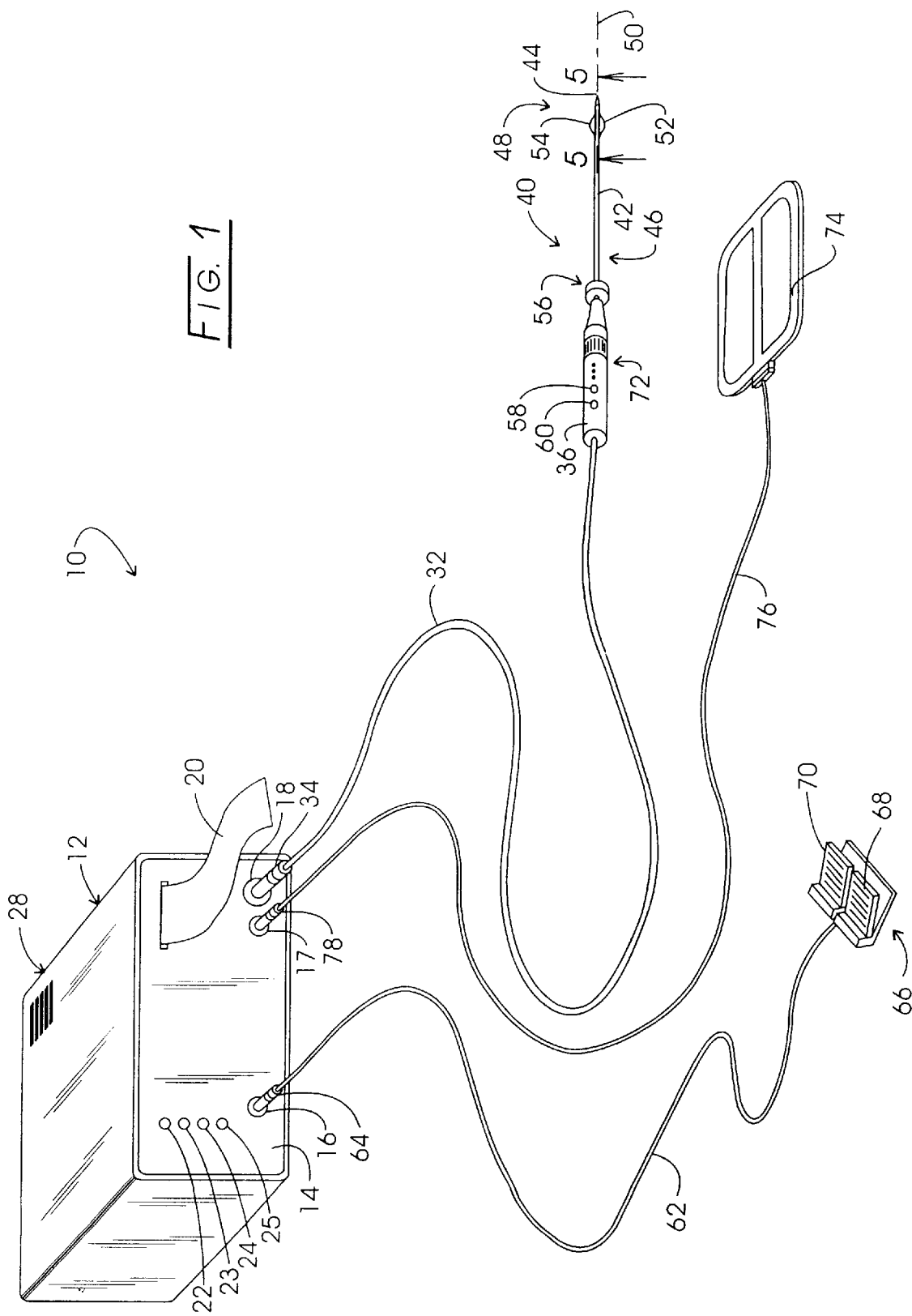
FIG. 1 is a perspective view of one embodiment of the system of the invention.

Referring to FIG. 1, one embodiment of the thermotherapy system of the invention is represented generally at 10. System 10 includes a customized electrosurgical generator and control arrangement 12, having a forward panel portion 14, at the lower level of which are provided three connector receiving receptacles, 16–18. Above the latter two receptacles is a paper strip 20, extending outwardly through a slot behind which is positioned a printer assembly (not shown). Visual cuing through the media of selectively energized light emitting diodes LED) is provided at the panel 14 as represented at 22–25. Finally, rearwardly upon generator assembly 12 is an audio grill 28 through which aural cuing signals are broadcast.

A control assembly cable 32, having a connector 34, is shown extending from an electrical connection with receptacle 18 to the instrument or cutting and cauterization apparatus of the invention as represented generally at 40. Instrument 40 is seen to include an elongate support member represented generally at 42 which extends between a tip 44 and a base or rear region 46. Base region 46 for the instant embodiment is configured to attach to a removable handle 36 for manual positioning of the instrument 40. Extending inwardly from the tip 44 is a forward end region 48 which extends along a longitudinal axis 50 from the tip 44 and, during an insertion mode of operation, the forward end region 48 of instrument 40 is positioned in adjacency with the tissue volume to be cauterized. In this regard, in a principal embodiment, the tip 44 and the support member 42 are not inserted into the target tissue but into normal or healthy tissue immediately next to the volume of targeted abnormal tissue.

Seen extending outwardly from a deployment portion of the forward end region 48, are two electrode assemblies, 52 and 54. Electrode assemblies 52 and 54 are shown in a v-shaped deployed orientation which is developed following positioning forward end region 48 into adjacency with a volume of targeted tissue. During the positioning into or removal of instrument 40 from tissue, the primary components of the electrode assemblies are retracted into a nested orientation within the forward end region 48. Actuation of electrode primary components 52 and 54, for the instant embodiment is by an actuator assembly represented generally at 56. Handle 36 is seen to support control button-type switches 58 and 60. Such switches are utilized to activate the electrodes 52 and 54 initially with surgical cutting current and subsequently with cauterization current. As an alternate or supplementary arrangement, more remote switching may be provided. In this regard, a connector assembly cable 62 is shown having a connector 64 inserted in electrical communication with the receptacle 16 of generator assembly 12. Cable 62 extends to a foot pedal-type dual switch represented generally at 66 and having foot actuated switches 68 and 70 which may be used to activate electrodes 52 and 54 with surgical cutting current and cauterization current, respectively.

Returning to the handle component 36, visual cueing devices such as light emitting diodes (LED) also may be provided as represented in general at 72. Electrode assemblies 52 and 54 are operated in a monopolar fashion during their electrosurgical cutting performance. To provide a return for this form of cutting, a conventional patient return electrode is provided as shown at 74. Electrode 74, having an extended surface area, is applied to a surface of the patient's body and is seen connected to electrosurgical generator 12 by a cable 76 extending to a connector 78, which in turn is operatively inserted within the receptacle 17.

Upon power up of the assembly 12, a component of the control features thereof carries out a form of electrical interrogation of the instrument 40. In this regard, the electrosurgical cutting current waveform will vary in terms of peak-to-peak voltages within a range of about 500 to 3500 volts. This variance will depend upon the principal cross-sectional dimension or shape of the primary, wire-shaped components of the assemblies 52 and 54. In effect, the electrosurgical cutting involves a highly concentrated or localized energy deposition and associated heating of tissue to sufficient level to effect vaporization of cellular fluid. This causes the rupture of cell walls to carry out a "cut". By contrast, again depending upon electrode size, the cauterizing current will be generally of a continuous waveform having a peak-to-peak voltage in the range from about 20 to 1000 volts and exhibiting relatively lower current density. In several embodiments of the invention, the electrode assemblies will include a primary component functioning to carry out an electrosurgical cutting assisted deployment and a secondary electrode of much larger surface area functioning to apply relatively lower density cauterization currents. Thus, a desirable aspect of the invention is to provide an electrical parameter code component within the instrument 40 which is interrogated by the control system associated with the generator 12. Upon the interrogation of that code component, for example, LED 22 is energized to represent that the system is ready. Then the forward end region 48 of the instrument 40 is positioned within the patient adjacent the peripheral extent or boundary of the volume of targeted tissue. By depressing foot pedal 68 of switch 66, or actuating switch 58 on handle 36, the electrosurgical cutting procedure is initiated. As this occurs, the control within generator 12 energizes LED 23 to indicate an "energization" status and a distinct audible tone of an initial first frequency, for example, in the range from 800 to 1000 Hz, is generated and broadcast through the grill 28. The practitioner then actuates the instrument 40 at actuator assembly 56 to cause a gradual deployment of electrodes 52 and 54 from their nested original orientation.

Figure 2:
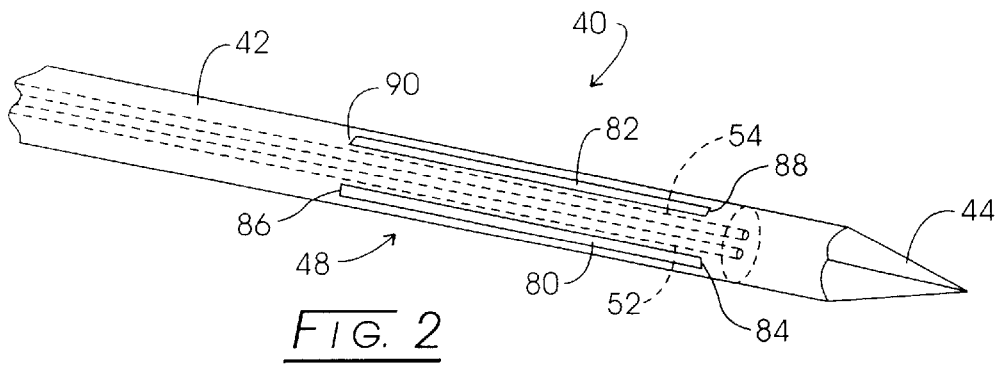
FIG. 2 is a perspective view of the cauterization instrument shown in FIG. 1 with portions shown in phantom to reveal internal structure.
Figure 3:
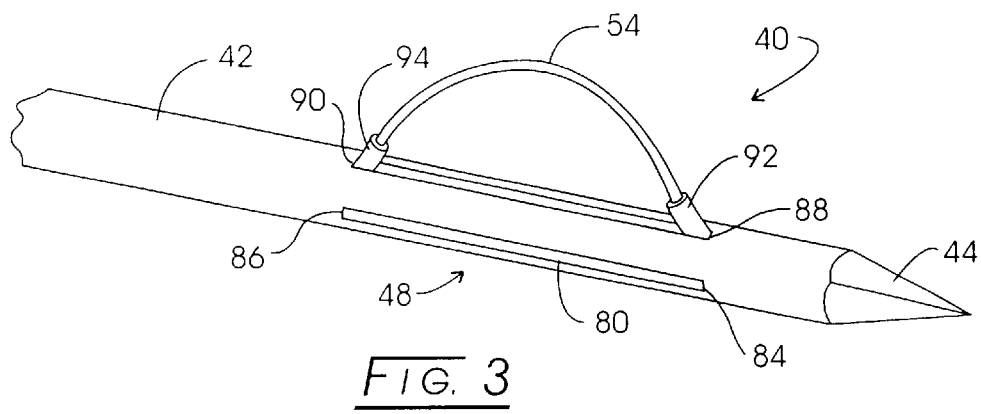
FIG. 3 is a perspective view of the front end region of the instrument of FIG. 2 showing one electrode assembly primary component deployed in a manner defining an arch.

Looking momentarily to FIGS. 2 and 3, the forward end region 48 of instrument 40 is shown at a higher level of detail. In FIG. 2, electrode assemblies 52 and 54 are seen in phantom as they are nested beneath the respective deployment portion assemblies 80 and 82 within forward region 48. The deployment assemblies 80 and 82 comprise outwardly open slots, slot 80 extending between forward location 84 adjacent tip 44 and a rearward location 86. Similarly, deployment slot 82 is seen to extend from a forward location 88 to a rearward location 90. FIG. 2 reveals that the distal ends of electrode assemblies 52 and 54 extend forwardly of the respective deployment slots 80 and 82 to an abutting form of connection with the support structure just rearwardly of the tip 44. The primary components or electrodes additionally extend at least an arch defining distance beyond the rearward locations as at 86 and 90. FIG. 3 reveals the arch structure which is developed when component 54 is urged forwardly in compression upon actuation from actuator assembly 56. Note in the figure that the forward and rearward regions of the component 54 are positioned within respective flexible insulative tubes or sleeves 92 and 94. Electrode component 54 is sidably positioned within sleeve 94 and fixed within sleeve 92. The sleeves 92 and 94 function to avoid short circuiting of the electrode with the support member 42.

Returning to FIG. 1, following deployment of the electrode assemblies 52 and 54 in an electrosurgery cutting mode, the control assembly at system 10 may provide an optional diagnostic function. For example, at this juncture in the procedure the system 10 may carry out an electrically derived evaluation of the targeted tumor. The electrode assemblies 52 and 54 may be employed under a multiplicity of frequencies ranging, for example from 20 kHz to 100 MFz at very low current levels to measure the electrical characteristics of the target tissue. In this regard, such measurement can determine malignancy or non-malignancy, as well as assess the degree of malignancy. See in this regard, application for U.S. Pat. No. 5,928,159 entitled "Apparatus and Method for Characterization and Treatment of Tumors", issued Jul. 27, 1999 by Eggers, et al., as well as U.S. Pat. No. 5,630,426, the entirety of which are incorporated herein by reference. The results of such diagnostic measurement may be recorded on the paper strip 20 by the control assembly of the generator apparatus 12.

For carrying out the cauterization mode or operation of the system 10, the practitioner actuates another switch such as that at foot pedal 70 or switch 60, at handle 36. As this occurs, RF cauterizing current is passed between the electrodes 52 and 54, preferably in a bipolar arrangement. Accordingly, the control assembly of the generator 12 will apply RF cauterizing current at one high potential to one such electrode and at neutral or lower potential to the other. During this RF cauterization current flow, a distinct audible tone of second frequency, for example in a range from 400 to 600 Hz is broadcast through the grill 28 and the "energized" LED 23 once again is illuminated at forward panel 14 or an LED within the array 72 of instrument 40 is energized. Once a predetermined change (i.e., decrease) in normalized current flow has occurred, the radiofrequency generator/control assembly 12 energizes light emitting diode 24 at front panel 14 or an LED within the array 72 upon handle 36. Generally, those LEDs are positioned adjacent a "therapy completed" label. Light emitting diode 25 at front panel 14 is a conventional "power-on" indicator. Following completion of the cauterization procedure, electrode assemblies 52 and 54 are moved in tension by the actuator assembly 56 to their nested orientation described in connection with FIG. 2. During return, if necessary, the electrosurgical cutting modality may be re-energized to facilitate this return maneuver.

Figure 4:
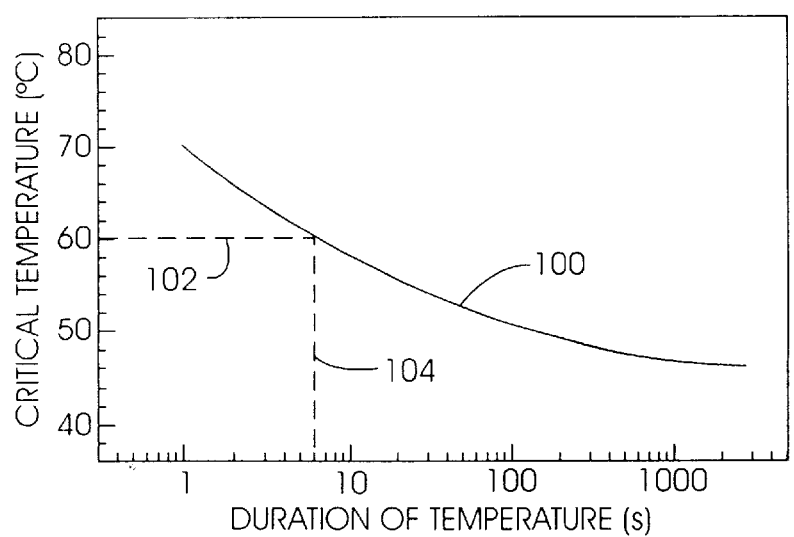
FIG. 4 is a chart showing critical temperatures for the occurrence of cell necrosis.

The issue of "thermotolerance," the ability of a subpopulation of cells (normal or malignant cells) which survive an initial subcritical thermal dose, to subsequently withstand exposure to the same temperature for typical treatment, does not present itself with system 10. The present thermotherapy will expose the entire target tissue volume which includes the known tumor or tissue mass plus a margin of surrounding tissue to temperatures in excess of 65° C. to 75° C. for periods of thirty seconds or more. Looking to FIG. 4, a curve 100 plotting temperature duration versus the critical temperature for evoking irreversible cell death is shown. The type of cauterization carried out with system 10, will result in irreversible cell death with a safety factor of 15× to 30×. Dashed lines 102 and 104 show that at 60° C. critical temperature, irreversible tissue effects will occur at six seconds. Moving up to the lower threshold of the instant system 10 at 65°, one may observe that the irreversible tissue effects occur with a duration of about two seconds. At 70° C. critical temperature, irreversible cell death occurs following an interval of about one second. See generally the following publication in this regard:

"Laser-Tissue Interactions, Fundamentals and Applications" by M. H. Neimz, 1996 Springer-Verlag, N.Y., Chapt. 3 pp 77, 78.

Referring to FIG. 5, a sectional view of the forward end region 48 of instrument 40 is revealed. In the figure, the tip 44 is shown to be configured having an annular shoulder 110 which is inserted within the forward end of the tubular support member 42. Tip 44 is seen to be configured as a trocar for purposes of penetration (percutaneous) through the patients' skin. Positioned immediately rearwardly of the tip 44 is a cylindrical, electrically insulative electrode engagement block 112 having a rearwardly facing cylindrical opening therein at 114 which adhesively receives both the component or electrode 54 and associated electrically insulative tube or sleeve 92.

Figure 6:
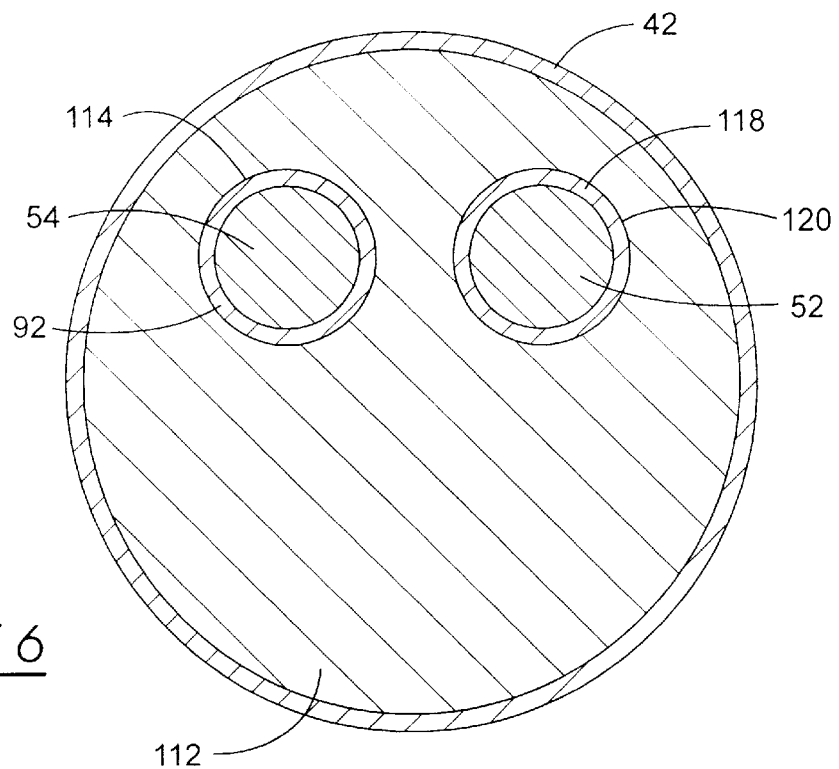
FIG. 6 is a sectional view taken through the plane 6—6 in FIG. 5.

Referring additionally to FIG. 6, a sectional view reveals the profile of the above-noted electrode engagement block 112 along with the opening 114 formed therein. Additionally a sectional view of component 54 and insulative tube or sleeve 92. Adjacent to component 54 is component or electrode 52 and its associated insulative tube or sleeve 118. The combination of component 52 and sleeve 118 is fixed within a cylindrical opening 120 within block 112.

In FIG. 5, the electrode or component 54 is depicted in its retracted or nested orientation as is utilized during an insertion mode wherein the instrument 40 is moved into adjacency with the volume of targeted tissue, as well as a removal mode wherein the instrument 40 is removed following a cauterization procedure. To support the electrode components, as well as to provide an outward bias at the commencement of their deployment, an electrically insulative cylindrical deflector guide component 122 is mounted within the interior 124 of the support member 42.

Figure 7:
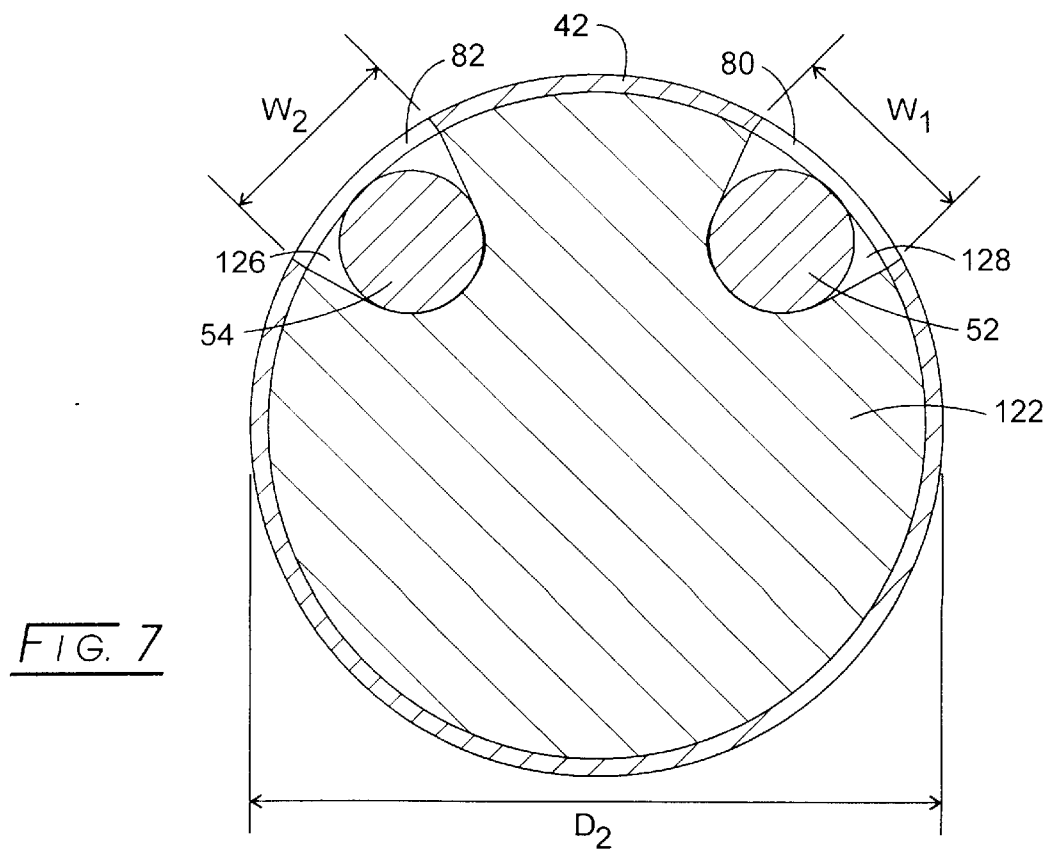
FIG. 7 is a sectional view taken through the plane 7—7 in FIG. 5.

Looking additionally to FIG. 7, a sectional view of the support member 42 at the position of deflector guide component 122 is revealed. It may be observed that an inwardly rounded truncated trapezoidal elongate notch 126 is formed in the guide component 122 to support the electrode component 54 at the appropriately outwardly biased orientation shown in FIG. 5. The outward width of the deployment portion or slot 82 is also represented in the drawing as $W_2$. FIG. 7 also reveals a similar elongate notch 128 for outwardly biasing the electrode component 52 in association with the deployment portion or slot 80. Slot 80 is shown in the drawing as having an outward width, $W_1$. Additionally, the support member 42 is shown having an outer diameter, $D_2$.

Returning to FIG. 5, electrode 54 is seen to extend rearwardly, whereupon it is slidably engaged by electrically insulative tube or sleeve 94 which, in turn, is fixed within a cylindrical cavity 130. Cavity 130 extends rearwardly from the outer face 132 of a cylindrical, electrically insulative electrode guide 134. Guide 134 is configured having a channel or lumen 136 through which the electrode component 54 may slide. Additionally, the guide 134 is fixed within the interior 124 of support member 42.

Figure 8:
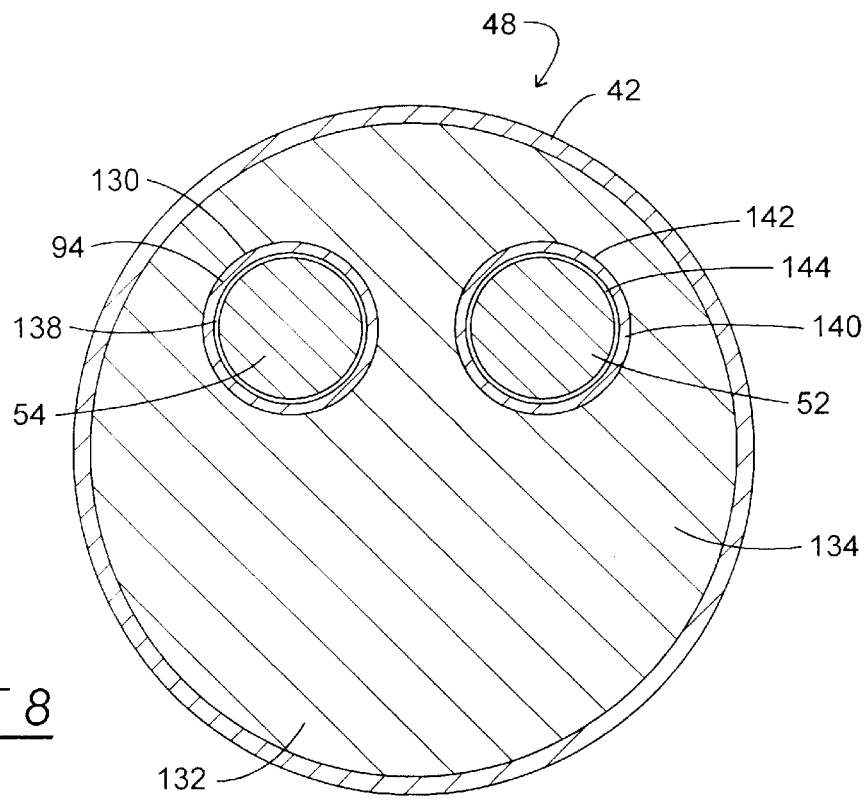
FIG. 8 is a sectional view taken through the plane 8—8 in FIG. 5.

Looking momentarily to FIG. 8, a sectional view of these features adjacent the face 132 of electrode guide 134 is provided. In the figure, it may be seen that the flexible insulative sleeve 94 is fixed within the cylindrical cavity 130 and that electrode component 54 is slidable within flexible, electrically insulative tubing 94, as is evidenced by the annular gap 138 located between the interior of tube 94 and the exterior surface of component 54. In similar fashion, electrode component 52 is mounted within a flexible electrically insulative guide tube or sleeve 140. Tube 140 in turn, is fixed within a cylindrical cavity 142 extending rearwardly from the face 132 of electrode guide 134. As before, component 52 is slidable within sleeve 140 as evidenced by the annular gap 144.

Figure 9:
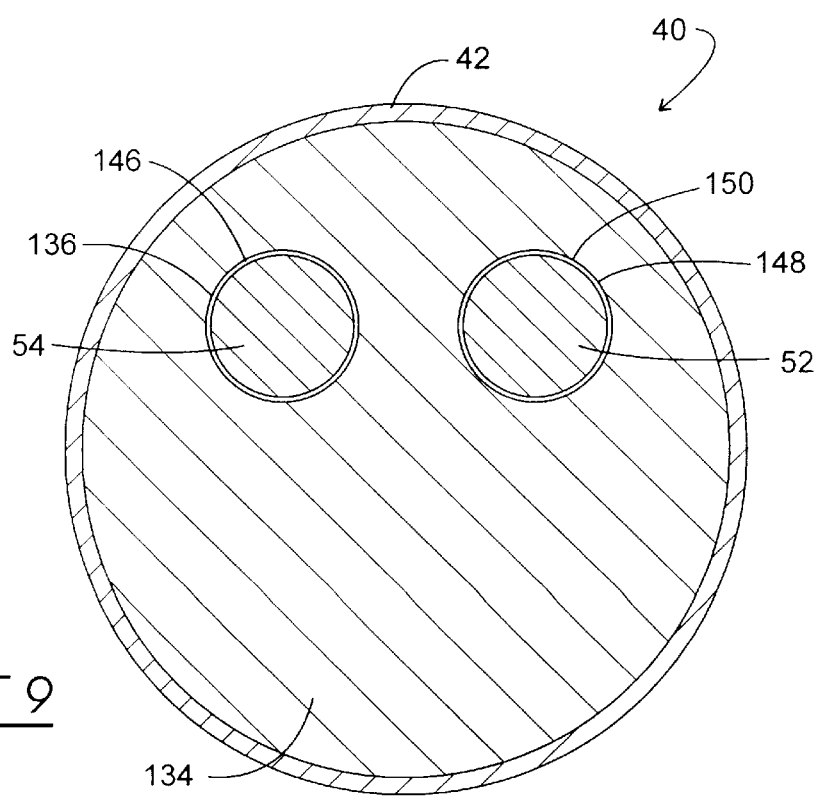
FIG. 9 is a sectional view taken through the plane 9—9 in FIG. 5.

Looking to FIG. 9, a sectional view taken just rearwardly of the section represented at FIG. 8 is portrayed. In this figure, the channel or lumen 136 extending through electrode guide 134 is revealed. Slidability of electrode component 54 through the channel 136 is evidenced by the annular gap 146 extending therebetween. In similar fashion, a channel or lumen 148 is configured within the electrically insulative electrode guide 134 for the slidable support of electrode component 52. Slidability is evidenced by the annular gap 150 extending therebetween.

Looking to FIGS. 5 and 10, the operation of this electrode deployment system is illustrated. In general, these primary electrodes may be constructed of an electrically conductive material such as tungsten, molybdenum, niobium, columbium, tantalum, vanadium, titanium, nickel, cobalt, iron, platinum, zirconium, copper, alloys containing one or more of the above-listed metals, stainless steel, or electrically conductive polymers or plastics. The electrode components as at 52 and 54 are deployed by utilizing an actuator assembly to mechanically urge them forwardly in compression against their forward connection, for example, electrode engagement block 112. As this compressive movement occurs, the electrode components are constrained from transverse movement at all locations except at the electrode deployment portion as at 82. Thus, the electrode components will tend to distort outwardly to form an arch-like structure, in effect moving outwardly transversely to the longitudinal axis 50. To assure that the transverse movement is outwardly, for the instant embodiment, the deflector guide component 122 provides a preliminary outward deflection or bias upon the electrode components. Looking to FIG. 10, electrode component 54 is shown in phantom at its insertion and removal mode nested orientation, and having been moved to an initial outward arch defining positioning as represented at 54'. The insulating function of insulative sleeves 92 and 94 becomes apparent from the figure. The extent of outward deployment is dependent upon the corresponding extent of forward movement of the electrode component 54. In this regard, it is actuated to move forwardly an "arch defining distance". Looking to FIG. 11, three positions of deployment of electrode component 54 are illustrated in conjunction with dimensional symbolism. In the figure, component 54 is shown in phantom at its nested or insertion and removal mode orientations. Next, the electrode is shown in its arch form deployment position 54' as discussed in connection with FIG. 10. Further actuation of the instrument 40 moves the electrode component 54 more forwardly to establish a higher intermediate arch position represented in phantom at 54". Finally, as represented at 54'", the component is shown at a maximum deployment height, $L_3$, extending outwardly from the deployment portion 82. Also shown in the figure is the designation for the length, $L_1$, of the deployment portion and the designation, $L_2$, for the distance from the forward end of the deployment portion to the forward end of tip 44. Shown additionally on the drawing is a principal dimension, $D_1$, for electrodes deployed with the instrument. Finally, the length, $L_4$, of the support member 42 from the forward end of tip 44 to the forward end of its base portion is represented in the instant figure in conjunction with FIG. 12.

The above dimension, $D_1$, as well as the cross-sectional configuration of the electrode may vary considerably depending upon the application at hand. In this regard, for smaller abnormal tissues or benign tissue cauterization procedures, smaller instruments are called for with correspondingly smaller principal dimensions, $D_1$. On the other hand, for purposes of carrying out cauterization with controlled current densities, the cross-sectional dimension is selected with an aspect of distributed current densities such that either a largest practical dimension is called for or secondary electrodes are deployed with a primary electrode component as at 54. Correspondingly, it is preferred that the power supplied from the electrosurgical generator function 12 to the electrode function, be customized to correspond with these electrode dimensions. This can be carried out by manual adjustment at the generator apparatus or by an instrument-borne coding approach.

Figure 12:
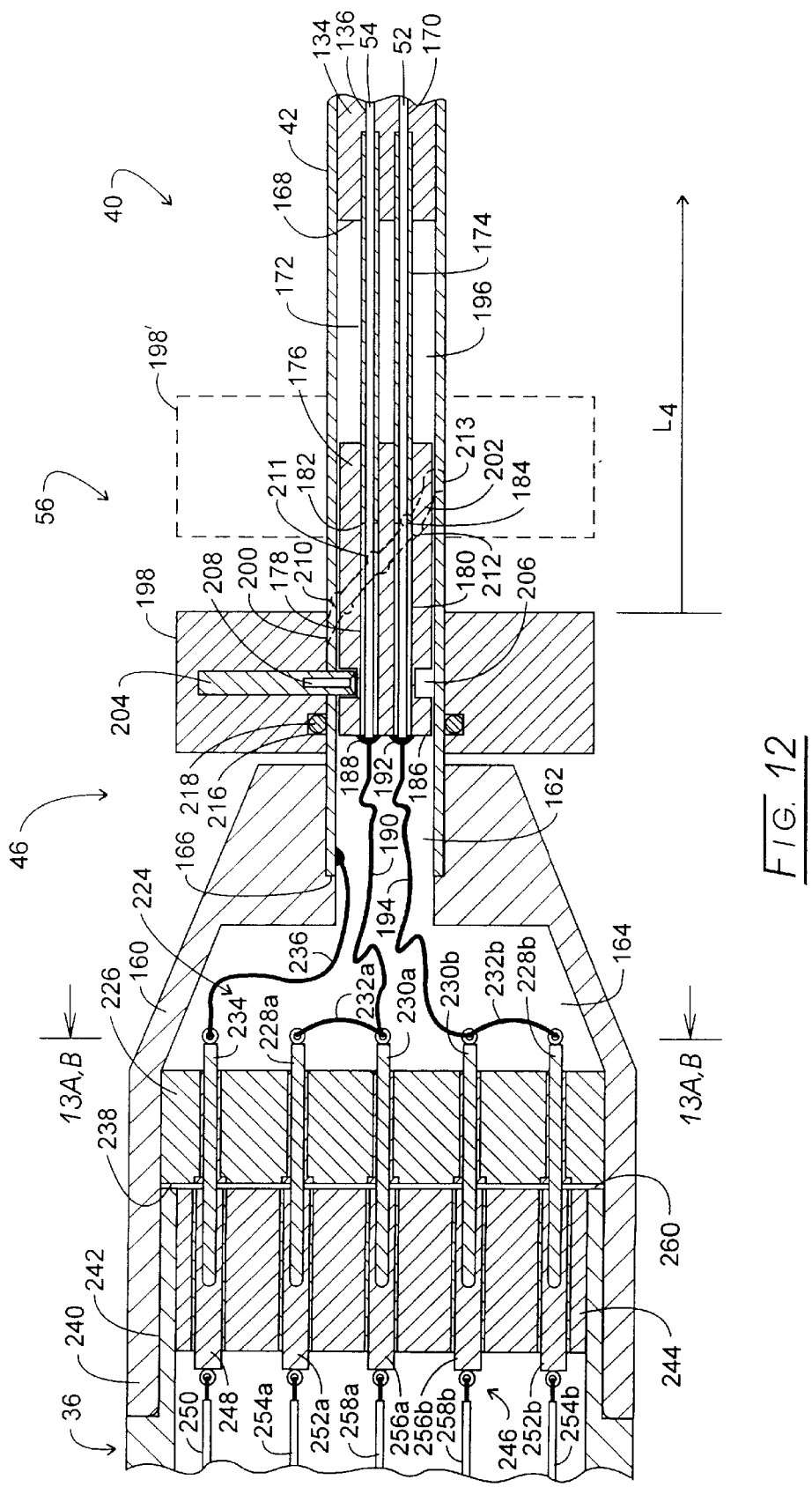
FIG. 12 is a partial sectional view of the base region of the instrument shown in FIG. 1.

The deployment of electrode assemblies 52 and 54 during the electrosurgical cutting mode may be simultaneous or in a manner wherein one is deployed and then the other. A variety of such actuation techniques are available. For the instant embodiment, simultaneous actuation is carried out from the actuator assembly 56 at base region 46. Referring to FIG. 12, base or rear region 46 is revealed in sectional detail as it is coupled with the support member 42. Looking to the figure, support member 42 is connected with the cylindrical forward base housing 160 of handle component 36 at a central cylindrical opening 162 extending therethrough to an interior cavity 164. The end of support member 42 is seen to abut against a shoulder 166 formed within the opening 162. Stationary electrode guide 134 is seen to extend to the base region 46, having a rearward face 168. Shown extending through the electrode guide 134 is the earlier described channel or lumen 136 within which is disposed electrode 54. Additionally, a channel or lumen 170 is located within the electrode guide 134 to slidably retain the electrode component 52 and restrain it for longitudinal movement only.

Mounted into the rearward face 168 of electrode guide 134 are two tubular, rigid insulative support sleeves 172 and 174. Slidably retaining respective electrodes 54 and 52, the sleeves 172 and 174 extend in cantilever fashion rearwardly into slidable insertion within an electrode drive block 176. In this regard, a channel or lumen 178 within the block 176 sidably receives sleeve 172. Similarly, a channel or lumen 180 within drive block 176 slidably receives rigid support sleeve 174. Note that sleeve 172 is seen to end or terminate at 182, while, correspondingly, sleeve 174 terminates at 184. However, electrode component 54 extends beyond termination point 182 within channel 178 to the rear face 186 of block 176. Block 176 is formed of an insulative material and electrode component 54 is seen to be attached to the block at its rear face 186 as seen at bond 188. Attachment may be by an adhesive. Also electrically coupled to the terminus of electrode component 54 is a flexible electrical lead 190. Lead 190 is configured in a loosely extended fashion to provide "slack" to permit its forward translation upon the actuation of the electrode system.

In similar fashion, electrode component 52 extends slidably through the sleeve 174, thence through the channel or lumen 180 within block 176 to block rearward face 186. At that position, it is adhered to the face 186 of block 176 with an adhesive bond represented at 192. Additionally connected to the terminus of electrode component 52 is an electrical lead 194 extending within the cavity 164. As in the case of lead 190, lead 194 is provided having sufficient "play" or length to accommodate forward moving actuation of the electrode system. Electrode drive block 176 is slidably mounted within the rearward cavity 196 of support member 42 and its position is controlled by the practitioner.

Advancement or retraction of the drive block 176 is carried out by the practitioner by rotating a cylindrical control knob 198 in a designated direction. In this regard, knob 198 is formed having a cylindrical bearing surface 200 which is slidably positioned over the outer surface of support member 42. At the location of this mounting, a helical slot 202 extends through and winds about support member 42. Extending through this slot 202 is a slot tracking pin 204 which is mounted radially within the knob 198. The inward end of tracking pin 204 slidably engages a rectangular annular groove 206 formed rearwardly within the electrode drive block 176. Spring mounted for outward bias within the slot tracking pin 204 is an expansion or detent member 208. With the arrangement shown, practitioner rotation of knob 198 will cause translational movement to occur with respect to both knob 198 and the block 176 either in a forwardly actuating direction or retraction direction. This occurs as the pin 204 tracks within helical slot 202. The resultant movement of block 176 drives electrode assemblies 52 and 54 forwardly or rearwardly. A maximum forward movement of knob 198 is represented in phantom at 198'. In effect, this translational movement amounts to the earlier described "arch defining distance".

To facilitate the positioning of knob 198 at intermediate or incremental locations along the track of the helical slot 202, grooves as at 210–213 are formed within the slot 202 which are releasably engageable by the detent member 208. Further stability of positioning may be provided by locating an annular slot as at 216 within the knob 198 extending outwardly from the cylindrical bearing surface 200. Within that slot, there is positioned an O-ring 218. The frictional engagement of the O-ring 218 with the outer surface of support member 42 will enhance the stability of positioning of knob 198 and, in consequence, the positioning of electrode assemblies 52 and 54.

During the deployment of electrode assemblies 52 and 54, an electrosurgical cutting defined current and voltage is applied to each of the electrodes from electrical leads 190 and 194. This procedure is carried out in monopolar fashion and, preferably, in conjunction with use of a remote return electrode as described at 74 in FIG. 1. When the electrodes have been deployed to an appropriate position or position within a sequence of positions, the mode of operation changes and cauterization of the abnormal or interstitial tissue is carried out. In a preferred arrangement, this is done by applying a cauterization defining lower density current and associated voltage across leads 194 leading to electrode assembly 52 and lead 190 to electrode assembly 54.

The leads within cavity 164 extend to an array 224 of connector pins which extend from their mounting within a connector mounting block 226 into cavity 164. Five of these connector pins of the array 224 are seen in FIG. 12. In this regard, pins 228a and 228b supply electrosurgically cutting defined current and voltage. Correspondingly, connector pins 230a and 230b are configured for bipolar cauterization performance. Note that connector 228a is connected via a jumper 232a to connector pin 230a and that monopolar operating pin 228b is connected to pin 230b via jumper 232b. Pins 230a and 230b, in turn, are coupled via respective leads 190 and 194 to electrodes 54 and 52. Thus, with appropriate control logic evoked from the control features of electrosurgical generator 12, connector pins 230a and 230b are open circuited during the electrosurgical cutting performance with current delivery emanating from connector pins 228a and 228b. Conversely, connector pins 228a and 228b are electrically open circuited during such time as cauterization procedures take place with the active employment of connector pins 230a and 230b. An optional connector pin within the array 224 is shown at 234. As shown by flexible lead 236 which is electrically connected to the support member 42, this connection may be used to apply electrosurgical return to the support member 42 either at the location shown or more forwardly, for example, at a discrete return or additional electrode within the forward end region 48 (FIG. 2).

Handle 36 is removably coupled to the assembly including housing 160 and block 226 and extends rearwardly from the rearward face 238 of block 226. With the opposite sides of the connector pin array 224 extending through face 238, and with housing 160 extending as an open right cylinder at wall 240, male socket arrangement is evoked. Thus, the instrument 40 can be plugged into the mating female socket of handle 36 for connection to the generator and control assembly 12 via cable 32 (FIG. 1). Accordingly, the hand manipulable handle 36 may be provided for use with any of a variety of instruments 40. The handle component 36 is necked down at 242 to be insertable within the cylindrical receptacle cavity defined by wall component 240. Necked down portion 242 is connected with a cylindrical receptacle support block 244 which contains an array of electrical pin receptors shown at 246. These receptors correspond with the connector pins of array 224. Of the pin receptors shown, pin receptor 248 provides connection with pin 234 and functions to couple electrical return from lead 250. Pin receptors 252a and 252b function to provide monopolar electrosurgical cutting current and voltage and are seen connected with respective input leads 254a and 254b. Pin receptors 256a and 256b provide for bipolar electrical communication with respective pins 230a and 230b and are coupled ultimately to the electrosurgical generator via respective leads 258a and 258b. Pin receptors of the array 246 extend forwardly to the forward face 260 of pin receptacle support block 244 to provide for connection with the corresponding connector pins of array 224.

Figure 13A:
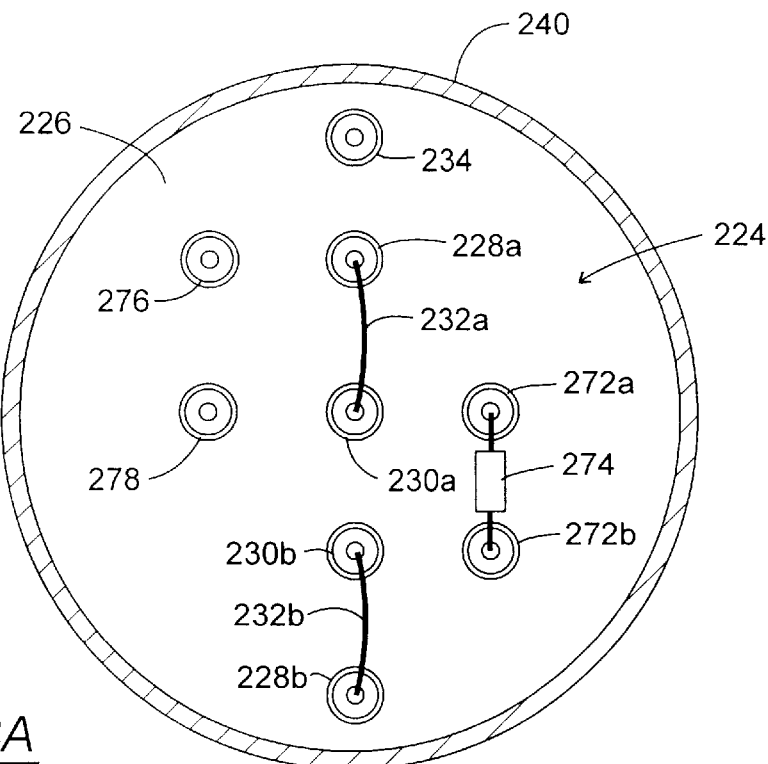
FIG. 13A is a sectional view taken through the plane 13A—13A shown in FIG. 12.

To provide a form of automatic adjustment of the electrosurgical generator control with respect to the type of the electrodes deployed and electrical parameters desired, the connector pins at array 224 may be employed for coding purposes. Additionally, certain of the connector pins may be utilized to, convey supporting technical information such as the temperature of tissue in the vicinity of the forward end region 48 of instrument 40. Such additional control functions are shown in FIG. 13A in conjunction with the earlier described pin connectors of array 224. In that figure, connector pins 272a and 272b are provided in circuit connection with an electrical coding element 274. Element 274 may be, for example, a resistor, capacitor or inductor which is interrogated from the control system at generator and control arrangement 12 to identify voltage and/or current settings and limits for tissue cauterization procedures, particularly corresponding with the functional physical characteristics of the electrodes involved as at 52 and 54. Where a temperature sensor is incorporated at the tip region of the instrument, then the temperature output condition of the sensor may be provided at connector pins 276 and 268. Looking to FIG. 13B, an additional arrangement is provided wherein a pin connector 272c is incorporated which is cooperative with connector 272b to provide access to a coding element 280. As before, the coding element 280 may be a resistor, capacitor or inductive component which functions to identify the voltage setting to be used for the electrosurgical cutting mode carried out during the deployment of electrodes 52 and 54.

Referring to FIG. 14, a block schematic representation of the surgical generator and associated control assembly of the system 10 is portrayed. In general, this latter feature of the system functions to decode the code carrying electrical parameters within the instrument 40. Then, responding to switch actuation from the practitioner, the generator function supplies a monopolar RF electrosurgical cutting current to the electrodes of instrument 40 as the practitioner actuates those electrodes into an operative position or positions for cauterization. For some embodiments, the electrodes 52 and 54 are deemed "primary" or "cutting" electrodes and are used in conjunction with high density current and cutting voltage inputs. The cauterization current, however, may be applied to "secondary" electrodes which preferably are electrically isolated from the primary electrodes and which exhibit relatively high surface areas as compared to the primary electrodes. This evokes a low current density input to the targeted tissue from advantageously larger electrode surface areas. When desired deployment of the primary electrodes has been accomplished, then the practitioner will switch the system to a cauterization mode wherein, RF cauterization current and voltage is applied across the deployed electrode assemblies which may be secondary electrodes. Where one current generator is employed with the system, then switching to provide this alteration of electrode tasks is called for. However, in the instant system, two generators are provided, one to supply the cutting current and the other is to supply the cauterization current. This selection stems for example, from the fact that a much higher voltage is required for the cutting function than for cauterization and the electrical impedance during tissue cutting is greater than during non-arcing cauterization mode. It may be recalled that for the latter function, a lower voltage but higher current, may be employed for cauterization. It is beneficial that during the cauterization procedure, no desiccation of the tissue occur, inasmuch as that phenomenon will raise the impedance exhibited by the tissue immediately adjacent the operating electrodes thus, lower current densities are called for.

Looking to the figure, the radiofrequency (RF) cutting current electrosurgical generator is represented at block 286, while the radiofrequency (RF) cauterization current electrosurgical generator is represented at block 288. Earlier described connector receiving receptacle 16 reappears schematically in conjunction with cable 62 and connector 64 extending from the foot pedal switch 66. Similarly, connector receiving receptacle 17 reappears in connection with connector 78 and cable 76 which extends to the remote patient return 74 (FIG. 1). Cable 32 extending from the handle portion 36, as coupled with the instrument 40, reappears in connection with multi-pin connector 34 and multi-pin connector receiving receptacle 18.

Inputs and outputs associated with the connector 34 are shown in connection with a terminal block 290. The inputs and outputs at terminal block 290 are those associated with the connector pins described in connection with FIG. 13A. Accordingly, each of the connector locations at terminal block 290 is identified by the numerical identification of the connector pins set forth in FIG. 13A but in primed fashion. Additionally, the connector block 290 includes generalized representations for interface functions contained on the handle component 36 itself. In this regard, terminal 292 is electrically associated with switch 58 shown in FIG. 1, which signals the control system to commence electrosurgical cutting operation in similar fashion as switch 68 of foot pedal switch 66. Terminal 293 is operationally designated with respect to switch 60 at handle 36 and provides for the generation of a cauterization current defined output. Terminal 294 is designated for the purpose of energizing one LED at array 72 upon handle 36 which corresponds with the "energized" output at LED 23 shown in FIG. 1. Finally, terminal 295 is electrically associated with the illumination of an LED at array 72 on handle 36 which corresponds with the energization of LED 24 at the generator in control 12, representing a therapy completed visual cue. The terminals 292–295 are seen to be associated with a control logic circuit 296 via respective arrows 298–301. In similar fashion, the outputs of switches 68 and 70 of the foot pedal switch assembly 66 are introduced to the control logic circuit 296 via arrow 304.

Upon being powered up via a power-on switch (not shown), control logic circuit 296 carries out a sequence of procedures in anticipation of the switch actuations to be carried out by the practitioner. As represented by respective arrows 306 and 308, the control logic circuit, inter alic, carries out control over the activation of the RF electrosurgical cutting generator 286 and the RF electrosurgical cauterization generator 288. However, as a condition precedent to the outputting of the initially utilized electrosurgical cutting current from generator 286, the control logic circuit 296 responds to the selection signal input of a decoding circuit as represented at arrow 310 and block 312. Decoding circuit 312, in turn, is seen responding via leads 314 and 316 to the decoding electrical parameter condition developed via terminals 272a' and 272b'. This represents an interrogation of coding element 274 as described in connection with FIG. 13A. Following carrying out of a performance configuration of the cutting electrosurgical generator 286 with respect to the input from decoding circuit 312, control logic circuit 296 activates the display function represented at block 318, as represented by arrow 320. Display 318 provides an aural output as described earlier, as wel as an activation of the LED at 22 representing a "system ready" condition. Control logic circuit 296 then, as represented at arrow 322, applies a control signal to a solid state switching network represented at block 324. This provides for the closure of switch functions symbolically represented at S1 and S2 which couple output and return lines 326 and 328 with respective lines 330 and 332 extending to the primary input of an isolation transformer 334. Transformer 334 is employed to isolate the patient from the radiofrequency generator and control system 12, as well as to isolate the RF cutting source 286 from the cauterization source 288. The output from the secondary winding of transformer 334 is provided at lines 336 and 338 and is directed to the input of a high pass filter represented at block 340. Filter 340 further reduces the amplitude of lower frequency signals, for example, frequencies below about 20 kHz which can otherwise lead to unwanted stimulation of nerves and/or muscle tissues within the patients' body. For example, interference is possible with natural or imposed pacing signals within the heart. The return component of the circuit upon exiting high pass filter 340, is coupled, as represented at line 342, with the remote patient return via receptacle 17. Correspondingly, the output from high pass filter 340 is directed, as represented at line 344, to terminal 228a' and thence via cable 32 to connector pin 228a for conduction via jumper 232a and lead 190 to electrode 54. Simultaneously, as represented at line 346 extending to terminal 228b', the monopolar type output is directed via cable 32 to connector pin 228b, jumper 232b and lead 194 to electrode 52 (FIG. 12). As this current is applied, the practitioner will turn the control knob 198 and provide for the simultaneous deployment of electrodes 52 and 54 into cutting activity at tissue locations, for example, adjacent targeted abnormal tissue. As discussed in FIG. 12 in connection with connector pin 234 and lead 236, as an alternative, the return may be developed from a return electrode supported at support member 42. This electrical association is represented at dashed line 348. Where the earlier noted "secondary" electrodes are deployed behind the primary electrodes 52 and 54, it is preferred that the output high pass filter 340, for example, at line 344 be isolated from those secondary electrodes. This assures the development of sufficiently high current densities at electrodes 52 and 54 to carryout an efficient cutting function.

Upon deployment of the electrode assemblies 52 and 54, the practitioner then releases the switch 58 or 68 which had been depressed to carry out this function. Then, either of switches 60 or 70 are closed to commence the cauterization mode of operation. With such closure, control logic circuit 296 responds by activating the display function 318 to provide an aural cue as earlier described, as well as to again illuminate the "energized" LED 23 as seen in FIG. 1, and an appropriate LED at the handle 36. RF cauterization electrosurgical generator 288 then is activated with the generation of a signal, as represented at arrow 322 and block 324, closing switches symbolically represented as S3 and S4. Such closure couples lines 350 and 352 with corresponding lines 354 and 356 which are directed to the primary winding of an isolation transformer 358. Transformer 358 provides the isolation features earlier described in connection with transformer 334. The secondary winding of isolation transformer 358 is directed via lines 360 and 362 to a high pass filter 364 which serves the same function as filter 340. From the filtering function 364, voltage and current are provided across lines 366 and 368 to corresponding terminals 230b' and 230a'. As illustrated in connection with FIG. 12, terminal 230a' is electrically associated via cable 32 with connector pin 230a, lead 190 and electrode 54, and terminal 230b' is associated via cable 32 with connector pin 230b, lead 194 and electrode 52 to evolve a bipolar form of current delivery through targeted abnormal or interstitial tissue. Where the earlier noted secondary electrodes are employed having enhanced surface areas, then the bipolar outputs from the filter 364 are directed to them, preferably by a separate electrical lead arrangement isolated from the electrical inputs to electrodes 52 and 54.

Particularly during this mode of operation of the system 10, the temperature from a temperature sensing element may be sensed by a sensing device provided upon support member 42, as above described, and the condition thereof is interrogated via cable 32 and presented at terminals 276' and 278'. These terminals respectively are connected with lines 370 and 372 to a temperature logic function represented at block 374. A resulting temperature signal is submitted, as represented at arrow 376, to the control logic function 296. The signal at line 376 can be employed by the logic circuit 296 to modulate the applied power developed at cauterization source generator 288 or, the cutting source at generator 286. Inasmuch as the temperature at the target tissue will respond with elevated impedance when necrosis of that tissue occurs, the resulting input to the control logic circuit 296 can be employed not only to terminate generation of an output from generator 288, but to provide a corresponding visual and/or aural output at the display 318.

A current monitoring function also is provided in connection with the cauterization output of the electrosurgical generator 288. This current monitoring is represented at symbol 378 within lines 354 and 356 at the output of switching function 324. The current levels monitored at function 378 are conveyed to the control logic circuit 296, as represented by arrow 380. Resultant current information may be employed to indicate the status of the ongoing therapy or to provide a feedback form of control over the radiofrequency source represented at the electrosurgical generator 288 to ensure that a pre-selected current limit for a particular therapy application by instrument 40 is not exceeded.

Figure 11:
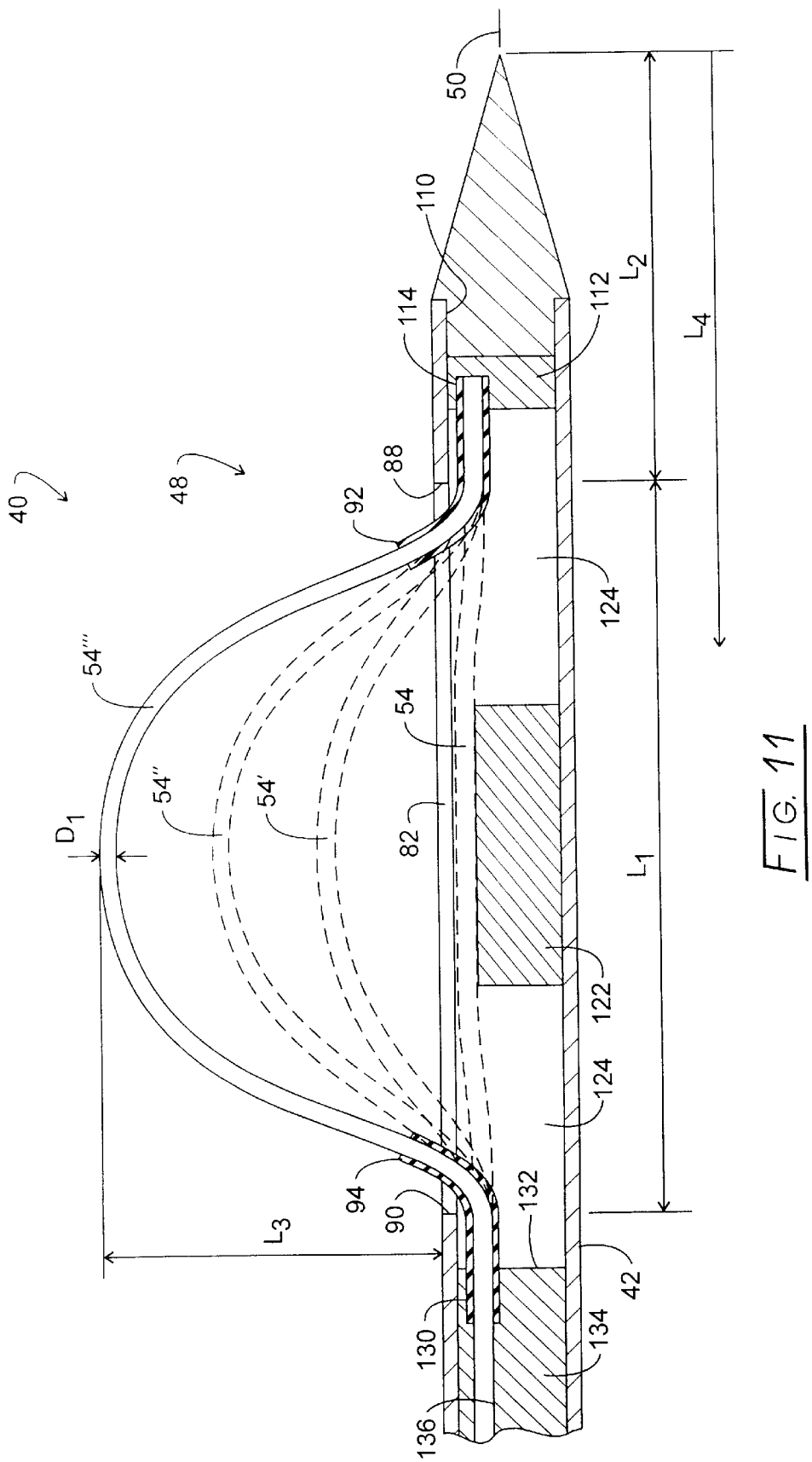
FIG. 11 is a sectional view of the front end region shown in FIG. 5 illustrating incrementally deployed orientations of an electrode primary component.
Figure 15:
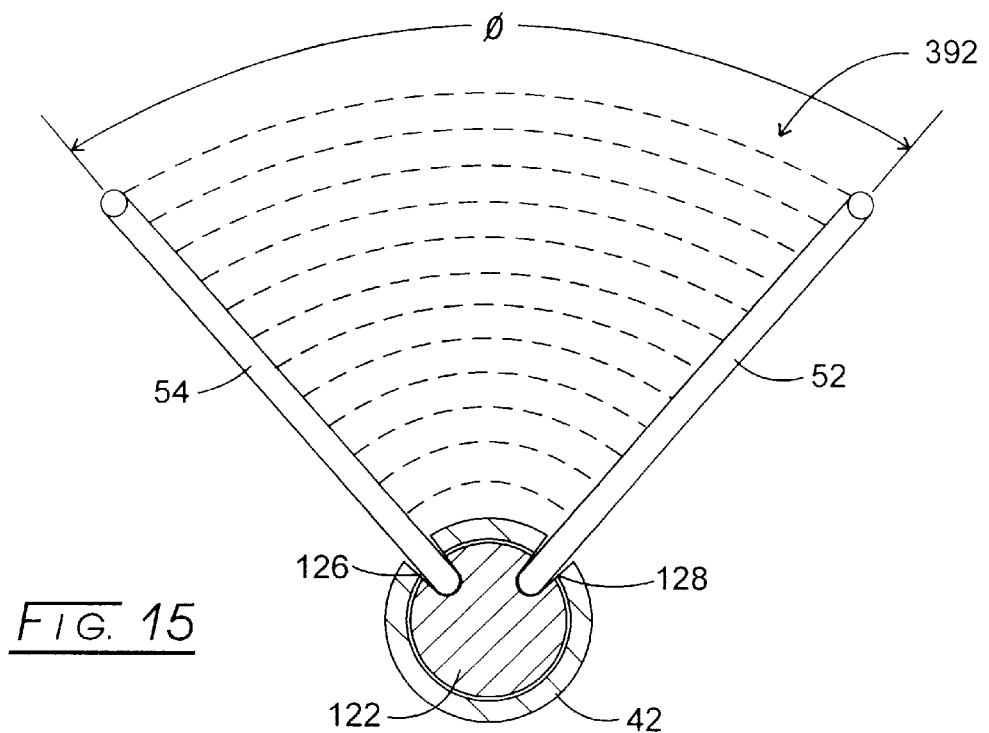
FIG. 15 is a sectional view illustrating deployment of two electrode assemblies and current flow between biactive electrodes.

Support member 42 may be formed from a variety of materials, for example, metals such as stainless steel, elastomeric materials, plastic materials or inorganic materials such as ceramic, glass/ceramic or glass. For purposes of accurately positioning it with respect to targeted tissue volume, the forward end region or working end 48 may incorporate a coating, covering or component which enhances its image contrast. For example, coverings or components may be used as radiography markers, in which case, a platinum band may be positioned about the surface of the component. Additionally, an ultrasound contrast agent such as a coating of hollow microspheres may be positioned at that region. Because the size of targeted tissue may vary substantially, the dimension of certain components of the instrument 40 may fall within a range of values. In the forgoing figures, these variable dimensions have been graphically identified as $L_1$–$L_4$, $D_1$, as shown in FIGS. 11 and 12, where $L_x$ refers to length and $D_x$ refers to principal dimension, or if a circular dimension, refers to diameter. The geometric aspects $D_2$, $W_1$, $W_2$ have been illustrated in connection with FIG. 7, wherein $D_2$ represents diameter, $W_x$ refers to width. As shown in FIG. 15, $\phi$ represents the included angle between the deployed electrodes as at 52 and 54. While the principal dimension, $D_1$, of the electrodes 52 and 54 generally will be the same, as is apparent, they may be varied to suit the needs of the user, for example, in achieving a nesting relationship. However, the overriding requirement of current density control for cauterization purposes remains. The ranges for the above geometric parameters are set forth in the following tabulation:

| | |
|---|---|
| $L_1 =$ | 0.5 to 20 cm |
| $L_2 =$ | 0.1 to 20 cm |
| $L_3 =$ | 0.1 to 20 cm |
| $L_4 =$ | 3 to 150 cm |
| $D_1 =$ | 0.05 to 4 mm |
| $D_2 =$ | 0.3 to 10 mm |
| $W_1, W_2 =$ | 0.07 to 5 mm |
| $\Phi =$ | 10° to 180° C. |

Referring to FIG. 15, electrode assemblies 52 and 54 are depicted in their deployed orientation and are illustrated in connection with dashed current flux lines represented 35 generally at 392. This is a bipolar implementation of the instrument 40. So deployed, the electrode assemblies 52 and 54 are on generally opposed sides of the target tissue volume peripheral extent such that the current flux 392 will carry out a cauterization. Included angle, $\phi$, between electrodes 52 and 54, may have the earlier noted maximum range, but more preferably will be in the range of about 30° to 120°. The time during which this cauterization current is applied may range, for example, between 1 to 2000 seconds.

Figure 16:
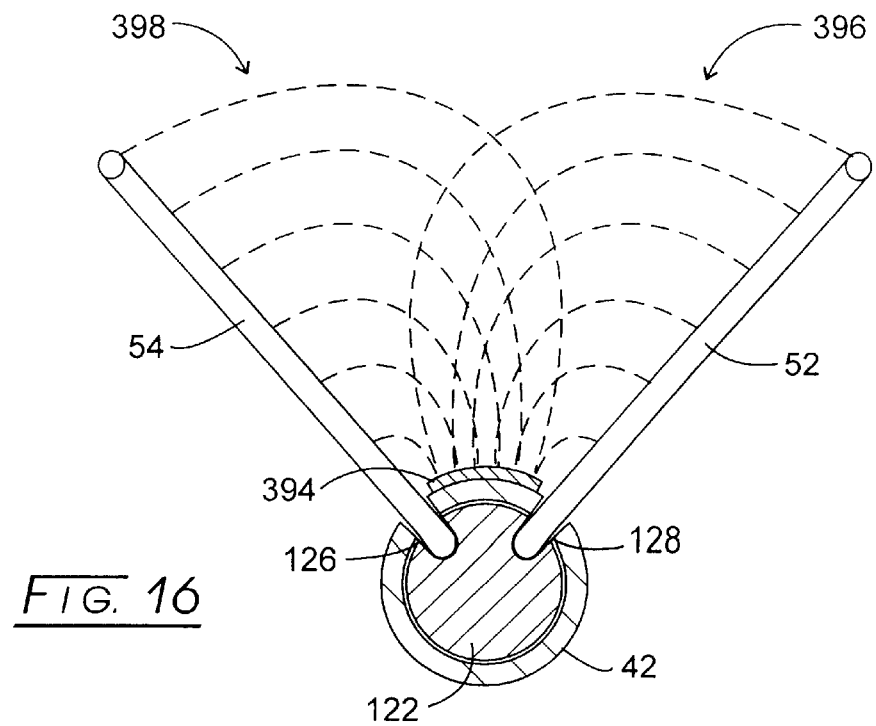
FIG. 16 is a sectional view of an instrument according to the invention showing a surface mounted electrode performing in conjunction with deployed electrode assemblies.

Looking to FIG. 16, an alternate, somewhat quasi-bipolar electrode configuration is depicted. For this embodiment, a third surface mounted electrode 394 is located upon support member 42 at the forward region at a location intermediate electrodes 52 and 54. The electrode 394 is shown in exaggerated dimension and, where employed with an electrically conductive support member 42, must be mounted in an insulative fashion. Cauterizing current and voltage is applied across combined electrodes 52 and 54 and electrode 394. A resultant current flux configuration then is evoked as represented by the dashed line array representation of current flux lines at 396 and 398. For the arrangement of FIG. 16, current flow may be caused to occur from one primary electrode as at 52 for a time duration within a range of 1–1000 seconds followed by or concurrent with current flow from the opposite electrode 54 for a time interval within the same range. With additional switching logic, a third increment of energization can occur with the embodiment of FIG. 16 wherein the electrode 394 is open circuited and electrodes 52 and 54 are energized in common bipolar fashion. Time increments of energization are adjusted accordingly for such an implementation.

Figure 17A:
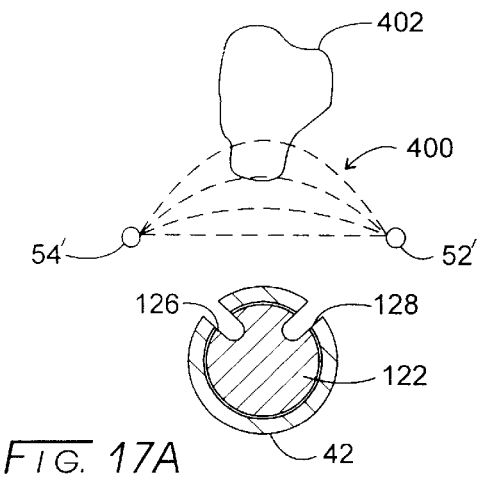
FIGS. 17A–17D are sectional views illustrating the incremental deployment and cauterization activity carried out with an instrument of the invention.
Figure 17B:
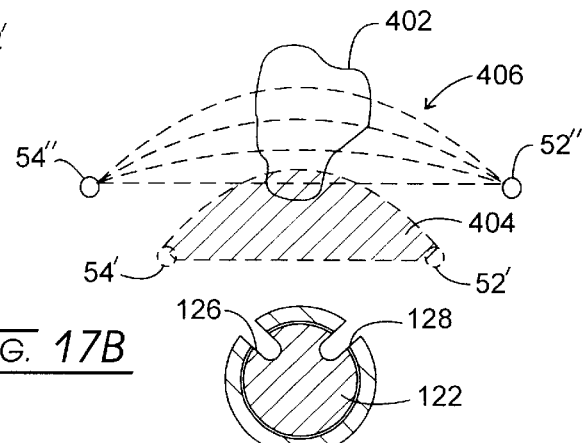
Figure 17C:
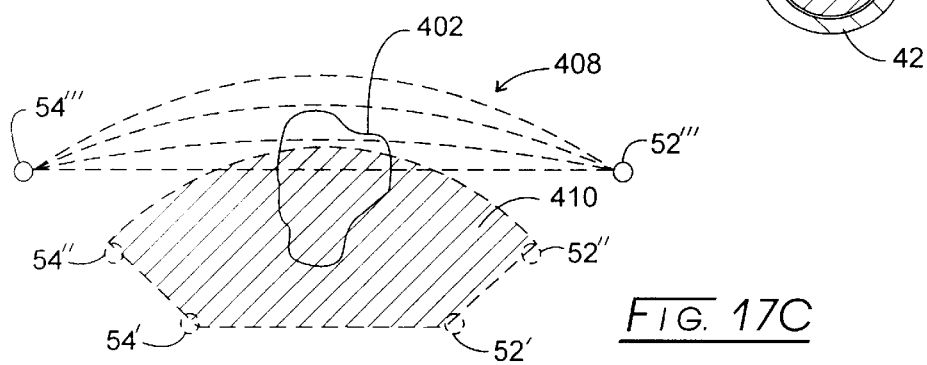

The deployment of electrode assemblies 52 and 54 preferably is carried out, as described in conjunction with FIG. 11 and electrode component 54, in an incremental fashion. In this regard, each electrode is deployed in an electrosurgical cutting mode to a first incremental position, whereupon the practitioner switches to a cauterization mode. In FIG. 17A, electrode assemblies 52 and 54 are shown at a first incremental deployment and operating in a bipolar cauterization mode. In this orientation, voltage applied across the electrodes creates a current flow represented by array of dashed current flux line 400. The array of current flux lines 400 is seen to be cauterizing an initial portion of a targeted or abnormal tissue 402. Following this relatively shorter cauterization procedure, then as represented at FIG. 17B, the instrument 40 is switched to an electrosurgical cutting mode which, again is a monopolar form of energization of electrode assemblies 52 and 54 in conjunction with a remote patient return. Upon reaching a second incremental deployment orientation as represented at 52" and 54", the electrode assemblies 52 and 54 again, are switched to a bipolar cauterization mode. As represented by the dashed current flux line array 406, cauterizing current now is caused to flow at optimized density through a next portion of targeted or abnormal tissue 402. Meanwhile, a zone of cauterized tissue has been evoked as at 404 in consequence of the initial cauterization procedure of FIG. 17A.

Figure 17D:
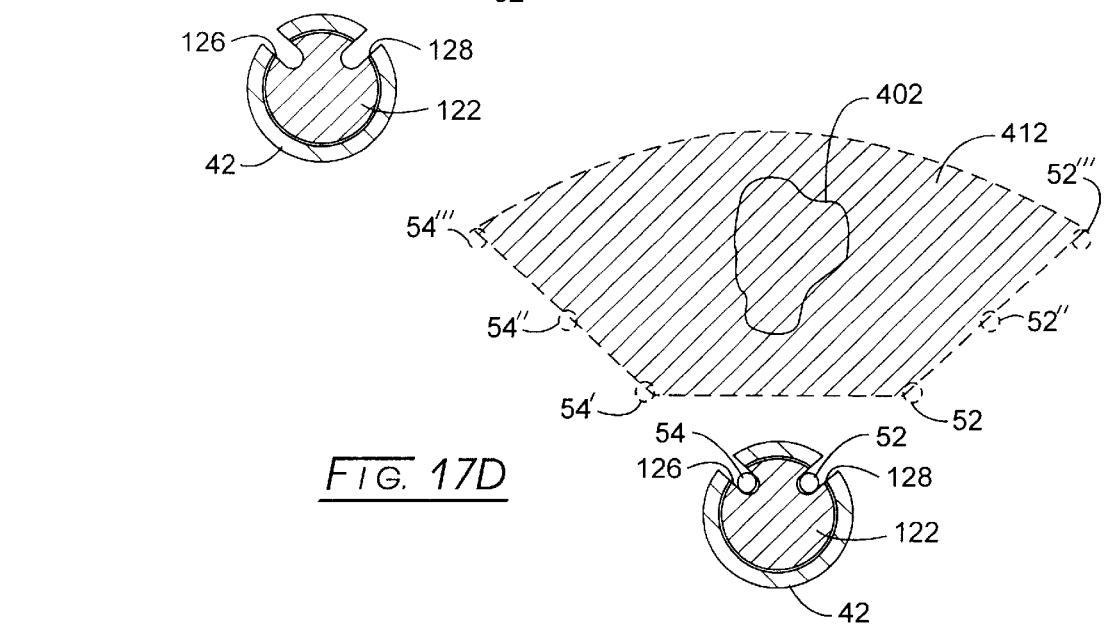
Figure 18:
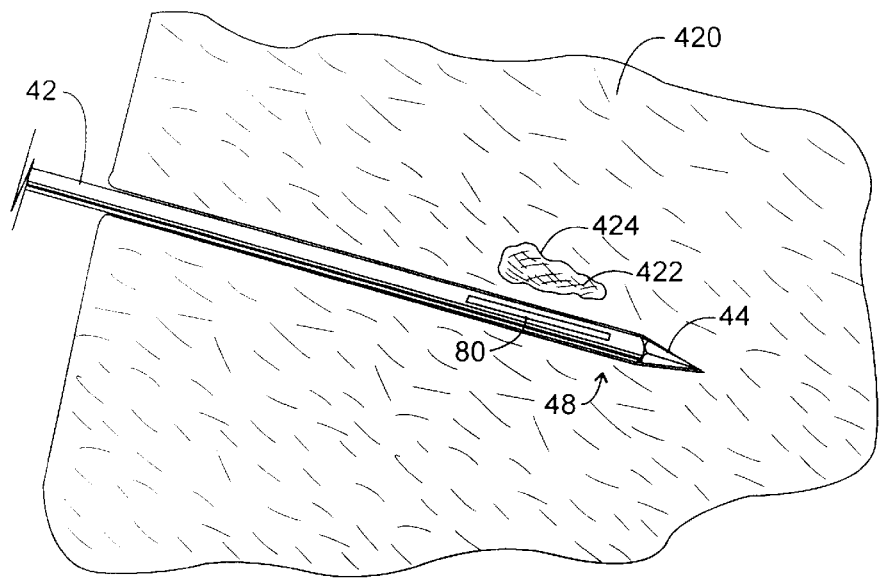
FIG. 18 is a perspective view showing the positioning of the front end region of an instrument according to the invention with respect to a targeted tissue volume.

At the termination of the cauterization interval with respect to electrode positions 52" and 54", then, the practitioner again switches the instrument to an electrosurgical cutting mode, which preferably will be monopolar, and deploys electrode assemblies 52 and 54 to the incremental deployment orientation shown in FIG. 7C at 52''', 54'''. Another zone of cauterized tissue will have been produced as at 410 in consequence of the second cauterization procedure described in connection with FIG. 17B. Upon electrosurgically reaching this position, then the instrumentation control assembly again is switched to a bipolar cauterization mode of operation to create the current flow between electrode assemblies 52 and 54 represented by the dashed current flux line array 408. Note that this array 408 encompasses the final portion of the targeted or abnormal tissue 402. At the termination of the cauterization interval, then as represented in FIG. 17D, the electrode assemblies 52 and 54 are retracted into respective deployment portions 80 and 82 (FIG. 2). In the instant figure, the electrodes are seen retracted into the respective notches 126 and 128 of the deflector guide component 122. The region of cauterization upon completion of the therapy, is seen in FIG. 17D at cross hatched area 412.

In the course of carrying out the procedure represented in FIGS. 17A–17D, during the deployment mode, the temperature imposed at the tissue confronting the electrode assemblies 52 and 54 will be well above 100° C. and the cutting effect, as noted above, causes a destruction of cells, inasmuch as water molecules contained within most tissues commence to vaporize at that temperature. Due to the large increase in volume during this phase transition, gas bubbles are formed inducing mechanical ruptures and thermal decomposition of tissue fragments. Gratuitously, this cutting action is quite local, thus, the term "cutting" is appropriate to describe it. The large vaporization heat of water (2253 kJ/kg) is advantageous, since the vapor generated carries away excess heat and helps prevent any further increase in the temperature of the adjacent tissue. Fluids in the thus formed "cuts" generated by the electrode assemblies 52 and 54 will enhance the electrical connection between the electrodes and the targeted tissue subject to subsequent cauterization. Preferably, cauterization procedures are carried out in the range of about 60° C. to 70° C. Within this range, the sticking of tissue or debris upon electrodes 52 and 54 generally will not occur. In this regard, sticking phenomena generally occurs, at temperatures above about 75° C. to 80° C.

The monopolar cuffing activity carried out by the electrode assemblies 52 and 54 during their deployment is one wherein the large surface return electrode is describable as "passive." In this regard, high current densities are present in the inmmediate vicinity of the electrode but not elsewhere, the cutting being quite local. On the other hand, during a cauterization procedure wherein electrode assemblies 52 and 54 perform in bipolar fashion, each is an active component in the production of current of lower density flowing from the electrode at higher potential to the electrode at lower potential. Electrodes performing in this joint participatory fashion are sometimes referred to as "biactive".

Temperature monitoring at the tip region of the support member 42 may be beneficial for the above procedure. In this regard, as temperatures at the targeted tissue approach excessive levels, controls can be provided, as described above, to modulate current development. As the electrode assemblies 52 and 54 are retracted to the orientation of FIG. 17D, they may again be energized with an electrosurgical cutting current to facilitate this maneuver. As noted above, temperature values also will correspond with the cauterization induced necrosis of the targeted tissue, and temperature threshold logic techniques can be employed to terminate a cauterization procedure.

Figure 19:
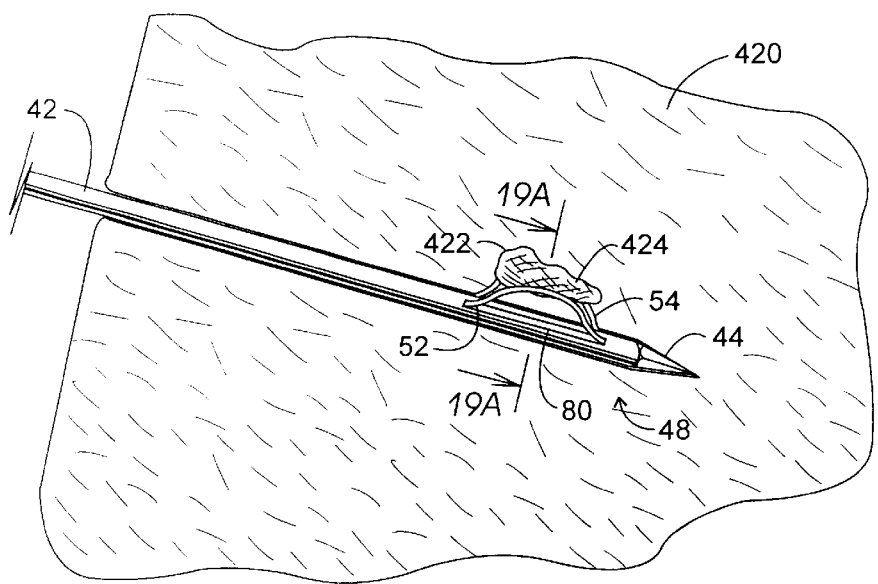
FIG. 19 is a perspective view showing the positioning of deployed electrode assemblies with respect to a targeted tissue volume.
Figure 19A:
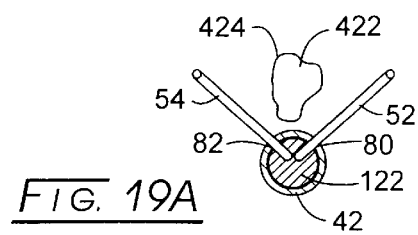
FIG. 19A is a sectional view taken through the plane 19A—19A in FIG. 19.

FIGS. 18 through 21 illustrate the instant interstitial cauterization procedure from a perspective viewpoint. Looking to FIG. 18, the insertion mode for instrument 40 is represented. In the figure, normal tissue is represented at 420. Within this normal tissue 420 there is portrayed a volume of targeted tissue 422 having a peripheral extent represented by the outline 424. The forward end region 48 of support member 42 of the instrument 40 is shown at the completion of an insertion mode. In this regard, the region 48 is positioned in adjacency with a peripheral extent 424 of targeted tissue 422. Note that the region 48 is not in contact with targeted tissue 422. Deployment portion 80 is shown with its associated electrode in retracted or nested orientation. In FIG. 19, instrument 40 is seen to have been actuated to deploy electrode assemblies 52 and 54 into effective adjacency with the peripheral extent 424 of targeted tissue 422 as seen additionally in connection with FIG. 19A. This deployment will have taken place in conjunction with the monopolar electrosurgical cutting, each of the electrodes 52 and 54 performing in conjunction with a remote patient electrode such as that described at 74 in FIG. 1.

Looking to FIGS. 20 and 20A, upon deployment of the electrode assemblies 52 and 54, cauterizing current is applied across them. A resultant current flux, as represented by dashed line array 426, carries out cauterization of the targeted tissue 422. Following this cauterization procedure, as represented in FIG. 21, the electrode assemblies 52 and 54 are retracted by actuation of instrument 40 and the instrument is withdrawn from the vicinity of the targeted tissue 422. The procedure will leave a relatively minor post penetration region 428 upon removal of instrument 40 caused by the separation of tissue during the insertion of the instrument 40.

Figure 22:
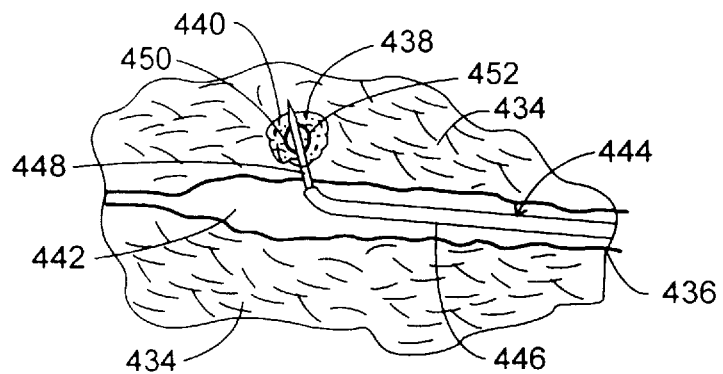
FIG. 22 is a pictorial representation of an endoscopically mounted instrument according to the invention.

The cauterization approach of the invention utilizing electrosurgically cutting deployed electrodes may be employed with a broad variety of delivery vehicles. Looking to FIG. 22, an endoscopic approach is revealed. In the figure, prostatic tissue is shown at 434 on either side of the urethral lining 436. Within this tissue mass, there is a volume of tumor 438 having a peripheral extent 440. Shown extending into the urethra 442 is a cystoscope illustrated generally at 444 having a guidable and flexible portion 446 outwardly from which a rigid end region 448 is seen penetrating through the urethral lining 436 into adjacency with the peripheral extent of tumorous volume 438. Electrode assemblies 450 and 452 are seen having been deployed by electrosurgical cutting and are oriented for carrying out bipolar cauterization.

Figure 13B:
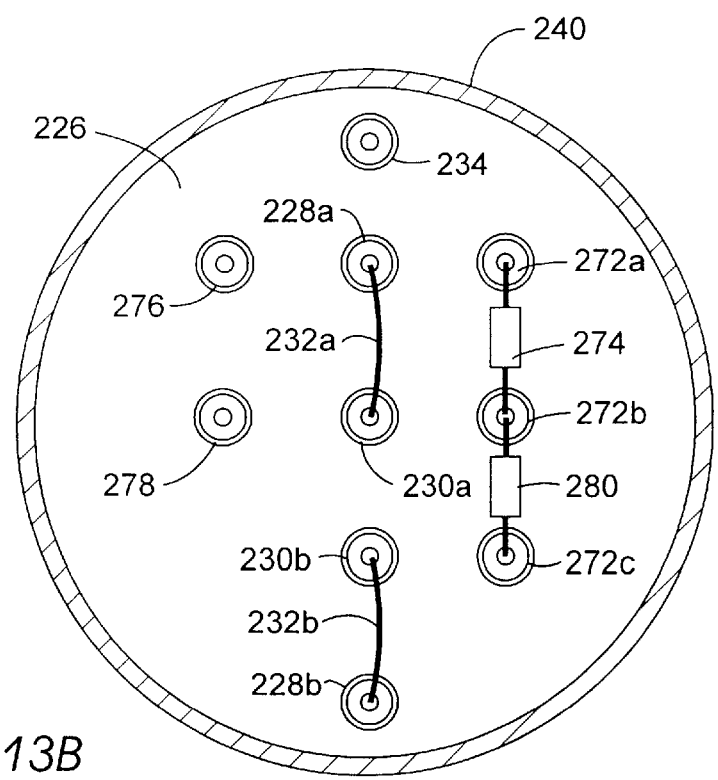
FIG. 13B is a sectional view taken through the plane 13B—13B shown in FIG. 12 and illustrating an alternate circuit configuration.

Referring to FIGS. 23A–23B, the method for utilizing instruments as at 40 is described in flow chart fashion. The method commences with a system start, as represented at node 460 and then continues as represented at arrow 462 and the instructions set forth at block 464. In the latter regard, the therapy application device is selected with respect to the volumetric extent of tissue to be cauterized. As described in connection with FIGS. 1–14, where a dual component handle and instrument combination is employed, the therapy application device is inserted into a hand piece or handle as at 36. Then, as represented at arrow 466 and block 468, one or more coding elements as described in connection with FIGS. 13A and 13B is interrogated or measured. This coding also provides for electing an appropriate cauterization RF voltage andlor current value. In the event that this interrogation indicates that the coding element electrical parameter is out of an appropriate range, then as is represented at arrow 470 and node 472, the system stops and the "ready" LED 22 is not energized.

When the electrical parameters for the instrument at hand are appropriate, as is represented at arrow 474 and block 476, "ready" LED) 22 is illuminated. Alternatively, an appropriate LED upon the handle 36 as at 72 may be illuminated. The program then proceeds as represented at arrow 478 and block 480 wherein the forward region 48 of instrument 40 is inserted within the patient. Insertion may be, for example, a direct visual placement, positioning through the use of stereotaxy, positioning based on previous imaging or upon real-time imaging. In the latter regard, ultrasound, magnetic resonance imagining (MRI) or fluoroscopy may be employed. Then, as represented at arrow 482 and block 484, the electrosurgical cutting switch 68 of foot pedal 66 is actuated or, alternatively, the switch 58 on handle 36 is actuated. This will cause the electrode assemblies 52 and 54 to carry out monopolar electrosurgical cutting as they are deployed with the actuation of knob 198 of the actuator assembly 56. For some instrument designs, secondary electrodes will be incorporated in conjunction with the primary electrodes as described at 52 and 54 above. The secondary electrodes function to provide the distribution of lower density cauterizing current at positions intermediate a fully deployed electrode and the forward end region of the instrument. Following the full or partial deployment of the electrodes, then, as represented at arrow 486 and block 488, cauterization switch 70 of foot pedal 66 is depressed or alternatively, the switch 60 on handle 36 is closed. For this purpose, the electrodes 52 and 54 may be incrementally deployed to, for example, an initial position as described in conjunction with FIG. 17A. Through, for example, temperature monitoring of the cauterized tissue region, an audible tone may be broadcast from the console 12 indicating cauterization completion and/or a display, for example, as at LED 24 may be illuminated to indicate incremental completion of therapy. The procedure then continues as represented at arrow 490. Arrow 490 reappears in FIG. 23B extending to block 492 wherein monopolar electrosurgical cutting switch 68 of the foot pedal 66 or switch 58 on handle 36 is depressed while knob 198 again is actuated to deploy the electrode components 52 and 54 to a next incremental outwardly disposed position. Then, as represented at arrow 494 and block 496, cauterization switch 70 of foot pedal 66 is depressed or, alternatively, switch 60 on handle 36 is actuated. Where a temperature sensor is incorporated with the instrument, then, additionally, the temperature of tissue adjacent the temperature sensing components of the instrument is measured and that information is decoded as represented at block 374 in FIG. 14 and submitted to control circuit 296. The practitioner awaits an audible tone and/or illumination of a display as at LED 24 to indicate that this next incremental component of therapy is complete. For determining the completeness of the therapy, alternatively, the practitioner may inspect imagining data, for example, ultrasound, MRI or the like to access whether cauterization of the intended zone of the tissue is complete. The procedure then continues as represented at arrow 498 and block 500 wherein a query is made as to whether the electrodes as at 52 and 54 have been deployed to their fullest extent or to the fullest extent desired, for example, as described in connection with FIG. 17C. Where such deployment has not been reached, then the procedure returns, as represented at loop arrow 502 to arrow 490 for carrying out a next incremental deployment. Where the query posed at block 500 results in an affirmative determination, then as represented at arrow 504 and node 506, the cauterization of the targeted tissue is completed. The procedure then continues as represented at arrow 508 and block 510, the electrodes being retracted to their nested orientation. As an alternative in this procedure, the electrosugical cutting switch 68 of foot pedal 66 may be actuated or the corresponding switch 58 on handle 36 may be depressed to facilitate this retraction procedure. Upon completion of this retraction procedure, then as represented at arrow 512 and block 514 the working end or forward end region 48 of the instrument is removed from the thus completed targeted tissue site. Complete removal of the instrument from the patient may be appropriate at this juncture or the device may be reinserted at another site for tissue cauterization.

Where sufficiently low density cauterization currents are not readily achievable with primary electrodes as at 52 and 54, the utilization of secondary electrodes in combination with such primary electrodes may be beneficial. With such an arrangement, the secondary electrodes, preferably in electrical isolation from the primary electrodes develop an electrode surface area which will be substantially greater than that of the primary electrodes. As a consequence, current density or current flux from the secondary electrodes is substantially lower so as to prevent unwanted desiccation of tissue while maximizing the rate of tissue cauterization. It is preferred that the larger surface area secondary electrodes be electrically isolated from the electrosurgically cutting primary electrodes, particularly during the deployment electrosurgical cutting operation of the latter. This follows inasmuch as a high current density is required to be developed in order to achieve efficient electrosurgical cutting on the part of the primary electrodes. For many applications, such high current densities may not be available where the larger surface area secondary electrodes are electrically associated with the primary electrodes. For some applications involving very small tumor or targeted region, the secondary electrodes may be combined electrically with the primary electrodes but only to an extent not evoking a performance lost with respect to the cutting function. Referring to FIG. 24, a primary/secondary electrode configuration is depicted for the latter, very small tumor application. In the figure, the forward end region 520 of a cauterization instrument is shown having an elongate slot or deployment portion 522. Deployment portion 522 is shown having a forward location 524 and a rearward location 526. Extending in arch-like fashion in deployed orientation outwardly from the deployment portion 522 is a wire-shaped resilient primary electrode 528. As in the earlier embodiment, electrode 528 is inserted into an electrically insulative flexible sleeve 530 extending outwardly from forward location 524 and is slidably mounted in a corresponding electrically insulative flexible sleeve 532 adjacent rearward location 526. Looking additionally to FIG. 25, fixed in an electrically conductive association to the underside of the wire-like electrode 528 are a sequence of quite thin electrically conductive flexible panels 534–538. Panels 534–538 may be constructed of the same material as utilized in forming electrode 535 and may be attached to the latter electrode by welding, braising, soldering, crimping or the like. When deployed as shown, the secondary electrode panels substantially enhance the amount of surface area available for low density current electrode performance in cauterization procedures. When the electrode 528 is in its nested or retracted orientation, the panels 534–538 are nested with it. In the latter regard, during insertion of the instrument, the panels 534–538 are stored within the instrument forward region. Note, in this regard, the panel 534 is faced further from the rearward location 526 than panel 538 is correspondingly spaced from the forward location 524. This arrangement is provided inasmuch as it is more practical to assure that the end panel 534 is stored within the deployment portion 522. Otherwise, the panel 534 would be, by necessity, located rearwardly of point 526. When the primary electrode 528 is retracted following a procedure, in general, the panels 534–538 are so diminutive in size and so flexible, that their reinsertion within the deployment portion or slot 522 is not necessitated. Because of their substantial flexibility, the panels 534–538 will simply fold about the electrode 528 for removal of the instrument.

FIG. 26 reveals another primary/secondary electrode configuration for the instruments of the invention. The forward end region for such an instrument embodiment is represented in general at 542. Positioned within that region 542 is a slot-shaped deployment portion 544 having a forward location 546 and a rearward location 548. Shown in its outwardly deployed orientation is a wire-shaped primary electrode 550 which extends into an electrically insulative sleeve 552 adjacent forward location 546 and which is slidably mounted within an electrically insulative sleeve 554 adjacent rearward location 548. Attached to the primary electrode 550 is an array of thin flexible secondary electrodes 556. Each of the electrodes of the array 556 extends within an electrically insulative sleeve of an array thereof 558. Each of the sleeves within array 558 is seen to extend outwardly from the slot-shaped deployment portion 544. This arrangement accommodates for the presence of an electrically conductive forward region 542. Alternatively, the portion of forward end region 542 adjacent the deployment portion 544 may be formed of an electrically insulative material. To provide a preferred electrical insulation for isolation of each electrode of the array 556 from the primary electrode 550, the electrode 556 may, for example, be formed of a flexible electrically insulative material which is coated with metal only to an extent in spaced adjacency with the contact or connection made with primary electrode 550. Such an arrangement avoids the compromising of desired high current densities at cutting electrode 550 during the electrosurgically cutting deployment operation of the instrument. Note, as before, that the secondary electrode of the array 556 closest to rearward location 548 is spaced further therefrom than is the corresponding electrode at the opposite end of the array 556 closest to forward location 546. This improves the storage of the secondary electrodes more adjacent rearward location 548 before their deployment.

Upon retraction of primary electrode 550 and the instrument from tissue, the inflexible electrodes of the array 556 are simply permitted to drape over the instrument. As before, when primary electrode 550 is in its retracted or nested orientation within deployment portion 544, the arrayed secondary electrodes 556 are nestably located with it within the forward region 542. When the array of secondary electrodes 556 is deployed as shown, a substantial increase in the amount of electrode surface area is developed to lower current density or current flux from the composite arrangement to avoid desiccation of tissue while maximizing the rate of tissue cauterization.

Referring to FIG. 27, another primary/secondary electrode configuration is revealed. In this figure, the forward end region of an instrument is represented in general at 560. Region 560 incorporates a slot-shaped deployment portion 562 having a forward location 564 and a rearward location 566. Extending in an outwardly deployed arch configuration is a wire-shaped primary electrode 568. Electrode 568 extends within an electrically insulated sleeve 570 positioned at forward location 564. The opposite end of the electrode 568 is seen to slidably extend from another electrically insulative sleeve 572 positioned outwardly at the rearward location 566. The secondary electrode of this embodiment is comprised of a thin, resilient sheet 574 having an arcuate edge 576 extending in spaced relationship from and within the arch defined by electrode 568. The opposite portion of the sheet 574 is wound about a driven mandrel shown in phantom at 578 and seen fixed to a flexible rotatable drive rod shown in phantom at 580. For this application, the lower surface portion having a boundary 582 of the secondary electrode 574 is coated with an electrically insulative material. In operation, as the primary electrode 568 is deployed in an electrosurgical cutting mode, the secondary electrode 574 is drivably unwound from the mandrel 578 and follows the deploying electrode 568 in the "cut" electrosurgically created. By so spacing the outer edge arcuate edge 576 of the secondary electrode from primary electrode 568, no electrical interference is evoked during the deploying electrosurgically cutting mode of operation of primary electrode 568. Citation of the secondary electrode 574 during a coagulation mode is by a separate lead input (not shown). Retraction of both electrodes can be carried out simultaneously.

Referring to FIGS. 28 and 29, another primary/secondary electrode arrangement for the instruments of the invention is illustrated. In FIG. 28, the forward end region of the support member of the instrument is represented generally at 590. The forward end region represents a continuation of a tubular structure having a tubular wall 592 with two slot-like electrode deployment portions, one of which is shown at 594 in FIG. 28 and each of which is shown at 594 and 596 in FIG. 29. FIG. 28 shows that the deployment portion 594 includes a forward location 598 and a rearward location 600. A trocar type of tip 602 is attached to the support member wall 592 at an annular shoulder portion 604 thereof. Fixed against the rearward face 606 of tip 602 is an electrically insulative electrode engagement block 608, having slots or cylindrical openings formed therein (not shown) for purposes of receiving both the primary and secondary electrodes. Positioned at the center of the deployment portion 594, is a cylindrical deflector guide 610, as seen additionally in FIG. 29. Looking to the latter figure, each of the deployment portions 594 and 596 contains an outermost primary wire-shaped electrode 612 and 614. Electrodes 612 and 614 are arch shaped when fully deployed as seen in FIG. 28. In addition to the primary electrodes 612 and 614, deployment portion 594 further retains wire-shaped secondary electrodes 616 and 617, while deployment portion 596 provides guidance and retention for arch-shaped wire-shaped secondary electrodes 618 and 619. FIG. 29 shows the nested or retracted orientation of electrodes 612, 616 and 617 in primed fashion and, correspondingly, electrode 614, 618 and 619 are shown in their retracted orientations within deployment portion 596 in primed fashion. FIG. 28 also reveals the retracted or nested orientations of electrodes 612, 616 and 617 in primed fashion. In the figure, primary electrode 612 is seen to be fixed within an electrically insulative sleeve 622 which extends into and is retained at the electrode engagement block 608. The opposite side of the extended arch-shaped electrode 612 is slidably mounted within a flexible electrically insulative sleeve 624 and slidably extends through an electrically insulative electrode guide 626 which is formed having a cylindrical channel 628 therein. As in the earlier embodiment, the electrode 612 is deployed to the orientation shown by urging it forwardly or actuating it an arch-defining distance. It is provided with a preliminary outward bias to assure appropriate deployment by the deflector guide 610. Secondary electrode 616 is similarly mounted within the instrument. In this regard, its distal end 630 is sidably fixed within an electrically insulative flexible sleeve 632 which is fixed, in turn, with the secondary electrode into the electrode engagement block 608, but at a location immediately adjacent and below the position of electrode 612 at its associated sleeve 622. Electrode 616, as well as electrode 618 extend rearwardly a secondary arch defining distance less than the arch defining distance associated with primary electrode 612. In similar fashion however, the electrode 616 is sidably positioned within an electrically insulative flexible sleeve 634 which is fixed to and extends from a cylindrical channel 636 formed within the electrode guide 626. This channel is located beneath and immediately adjacent to channel 628.

The distal end of the third secondary electrod 617 is seen to be fixed within an electrically insulative flexible sleeve 638 and it and the sleeve 638 are connected to the electrode engagement block 608. Electrode 617 extends rearwardly a secondary arch distance less than the secondary arch distance of secondary electrode 616 and is slidably inserted within an electrically insulative flexible sleeve 640. Sleeve 640, in turn, is connected to and is in alignment with a third cylindrical channel 642 formed within the electrode guide 626.

Electrodes 614, 618 and 619 are mounted in the same fashion with respect to the deployment portion 596 as seen in FIG. 29. As the primary electrodes 612 and 614 are deployed under an electrosurgical cutting mode of operation, preferably, secondary electrodes 616–619 are open circuited and actuated simultaneously with electrodes 612 and 614 to follow in the "cut" fashioned by the primary electrodes which are positioned in adjacency with the peripheral extent of targeted tissue volume. FIG. 29 shows such a tissue volume at 644 having peripheral extent at boundary 646. When all of the electrodes are fully deployed, then cauterizing current is caused to flow through all of them as represented by the now biactive electrodes 612 and 614 at dashed current flux lines 648. In similar fashion, cauterizing current is caused to flow between biactive secondary electrodes 616 and 618 as represented by the dashed current flux lines represented generally at 650. Finally, cauterization current is caused to flow between biactive secondary electrodes 617 and 619 as represented by the dashed current flux lines represented generally at 652. Retraction is carried out by actuating both the secondary and the primary electrode in tension either sequentially commencing with the innermost secondary electrode or simultaneously.

Referring to FIG. 30, a more detailed portrayal of an electrode assembly incorporating both a primary component and a secondary electrode assembly is revealed. In the figure, the forward region of an instrument is represented in general at 654. Region 654, as before, incorporates two electrode deployment portions, one of which is revealed as a slot structure at 658. This slot-shaped electrode deployment portion 658 extends from a forward location 660 to a rearward location 662. Shown deployed in arch-like fashion from the deployment portion 658 is a primary component or electrode 664. Supported from and deployed downwardly or unfurled from the primary component or electrode 664 is a sheet-form membranous electrode represented generally at 666. Electrode 666 is configured as a flexible circuit fashioned of a sequence of flexible panels 668a–668d. These slots, here shown to be three in number, are represented at 670a–670c. Note that the slots 670a–670c do not extend all the way to the union of the secondary electrode 666 with the primary component 664. This permits a metallic coating defining the electrode surface to electrically communicate amongst all of the panels 668a–668d. Electrical communication between this electrode surface coating and the electrical surgical generator is through a small thin portion of the membranous electrode shown at 672 and extending from the panel 668d. The metallic or metal surface coating, while extending above and across the slots 670a–670c, terminates at a border 674 spaced from the primary electrode component 664. This assures that the secondary electrode 666 is electrically isolated from the primary electrode component 664. Were there electrical connection between these two components, then the current densities for electrosurgical cutting by the primary component 664 would be insufficient. Note, additionally, that no panel exists in immediate adjacency with the rearward location 662. This eliminates interference of such a component during the deployment of the electrode assembly. In effect, the secondary electrode panels extend along the primary component or electrode 664 substantially from the forward location 660 to the rearward location 662 when the primary electrode 664 is within the deployment portion 658 during the insertion mode.

Looking additionally to FIG. 31, the connection between the secondary electrode at 666 and the primary component 664 is revealed. In the figure, the secondary electrode is seen to be formed upon a thin, membranous polymeric support 676. Support 676 may be formed, for example, of polytetrafluoroethylene, marketed under the trademark "Teflon" or an aromatic polyimide marketed under the trademark "Kapton". It will have a thickness of between about one-half to two mils and its upper edge region is seen to extend through an elongate slot 678 formed within the primary component or electrode 664. The slot 678 has a width corresponding with the widthwise dimension of the support 676. Note in the figure, that the primary electrode component 664 is tubular. For example, being formed of a type 304 or type 316 stainless steel having an outer diameter ranging from about fifteen to twenty-five mils, a wall thickness of about three to five mils to thus provide an elongate cylindrical internal cavity 680. Support 676 is retained within the cavity 680 with an adhesive such as an epoxy adhesive. FIG. 31 further reveals the flexible circuit coating or layer 682 supported by support 676. Finally, it may be observed that the primary component or electrode 664 is coated or surmounted by a thin polymeric electrically insulative layer 684 which extends to an elongate outwardly directed opening 686. Opening 686 extends substantially across the active region of the electrode 664 and provides for a current density concentration to enhance cutting action during electrosurgical assisted deployment. The opening 686 is seen having a width, E1. E1 may have a value of from about 0.5 mils to 10 mils. Flexible circuitry or coating 682 may be provided for example, as a gold plated copper coating.

Looking to FIG. 33, the stowed or undeployed orientation of the electrode assembly is revealed. In the figure, forward portion 654 is seen having a cylindrically-shaped deflector guide component 690 both sides of which incorporates the slot-shaped deployment portion 658. Primary electrode component 664 is seen nested within the deployment slot component 658 and is positioned upon oppositely disposed shelves or guides at 692. Secondary electrode 666 is seen to be folded and stowed or stored in nesting fashion within an extension of the slot or deployment portion 658. An oppositely disposed electrode assembly is represented generally at 694 in conjunction with the guide 696 correspondingly with guide 692. As before, the secondary electrode component is shown at 698, in folded or stowed orientation appropriate for the insertion mode.

Looking to FIG. 34, following a surgical procedure, the primary component or electrode 664 and 694 are retracted to the position shown in FIG. 33. However, the secondary electrodes 666 and 698 are not repositioned within the deployment portions. As shown in FIG. 34, the panels as at 668a–668d are permitted to drape over a portion of the forward region 654 for instrument removal purposes (e.g., by rotating the instrument as it is removed to facilitate wrapping of panels 668a-668d on forward portion 654).

Referring to FIG. 35, another but similar electrode assembly structure is revealed. In the figure, the forward region of an instrument according to the invention is represented generally at 700. Within the region 700, an elongate, slot-shaped electrode deployment portion is shown in general at 702 extending from a forward location 704 to a rearward location 706. A tubular primary component or electrode is shown at 708 in an arch-defining fully deployed orientation. As before, component 708 functions to unfurl or deploy and support a thin membranous flexible secondary electrode presented generally at 710. Electrode 710 is formed having thin, flexible panels 712a–712d which are defined by slots 714a–714c. Note, however, that the slots 714a–714c slope toward the rearward portion of the instrument to give the panel 712a–712d asymmetric configuration. As before, no panel is located in adjacency with the rearward location 706, in particular, an open region is established having a lengthwise extent commensurate with the earlier discussed arch-defining distance. However, a membranous conduit is provided as at 716 which is identical to that described at 672 in FIG. 32 and, as before, the secondary electrodes formed as a composite polymeric thin membranous material which is coated with a flexible circuit up to a border represented at 718. Looking additionally to FIG. 36, as before, the primary component or electrode is formed as a tube having an inner elongate cavity 720 and an elongate slot 722. As before, the secondary electrode 710 is formed as a composite with a thin membranous polymeric support 724 formed of the earlier described materials upon which is plated or coated a flexible circuit conductive layer as represented at 726. As before, the primary component or electrode as 708 is coated with an electrically insulative polymeric material 728 which, as described in connection with coating 684 in FIG. 31 extends to an elongate opening 730 defining the active surface of the electrosurgically cutting electrode component 708. The connection between support 724 and the interior cavity 720 of the electrode component 708 is not an adhesive one as described in the earlier embodiment. For the instant embodiment, the upper edge region of the support 722 may be coated, for example, with a layer of the same material forming the flex circuit 726 as shown at 732. However, the layer at 732 is electrically mutant, having no electrical association with circuit 726 and functioning simply to retain the port 724 in slidable connection with the primary electrode component 708. The secondary electrode arrangement as shown at 710 may be slidably inserted through the forward end of the primary electrode component 708 during the assembly of the instrument.

The slanted slot arrangement described in connection with FIG. 35 at 714a–714c develops a secondary electrode panel configuration, which, upon retraction of the primary electrode component 708 provides a rearwardly oriented edge which is slanted forwardly such that upon withdraw of the forward region 700, for example, in the direction of arrow 734, the panels 712a–712d are urged by their frictional engagement with surrounding tissue into the wrap-around and angularily oriented configuration shown in FIG. 37. This enhances the removal procedure.

Referring to FIG. 38, a multi-electrode instrumentation approach is depicted wherein the deployed arch-shape of electrodes is replaced with essentially straight and resilient elongate structures. As before, the structures are deployed by movement outwardly in conjunction with the electrosurgical cutting as in the earlier-described monopolar electrosurgical mode. The forward end region for such an instrument is represented in general at 760 extending to a trocar form of tip 762. In the embodiment, the region 760 is configured with three electrode pairs 764a, 764b; 765a, 765b; and 766a, 766b. Electrodes 764a and 764b are deployed from respective guidance ports 768a and 768b which, in turn, communicate with guidance channels shown in phantom respectively at 770a and 770b. Electrodes 765a and 765b are deployed from respective guidance ports 772a and 772b which are in electrical communication with respective guidance channels 774a shown in phantom at 774a and 774b. In similar fashion, electrodes 766a and 766b extend from respective guidance ports 776a and 776b which, in turn, communicate with guidance channels shown in phantom at 778a and 778b. Following their electrosurgical cutting form of deployment, the now biactive electrodes 764a, b–766a, b are energized in bipolar fashion to create the current flux densities represented by the array of dashed lines shown generally at 780. Because of the proximity of adjacent biactive electrodes, this dashed array is seen to demonstrate a form of "cross talk" wherein, for example, current flow will be witnessed between mutually longitudinally disposed electrodes such as between electrodes 764a and 765b and between electrode 765b and electrode 766a. The active length of the electrodes 764a, b–766a, b will be in a range from about 0.2 to 20 cm and preferably in a range of about 0.3 cm to 10 cm.

The instrument of the invention can be implemented with a single deployed electrode performing in conjunction with an electrode positioned in adjacency with the deployed electrode at the surface of the forward end region. Looking to FIG. 39, such a forward end region is represented generally at 786 extending to a trocar form of tip 788. A slot-shaped deployment portion 790 is located in region 786 between a forward location 792 and a rearward location 794. Shown deployed in arch-like fashion from the deployment portion 790 is a wire-shaped electrode 796. The resilient electrode 796 is fixed, as before, within an electrically insulative flexible sleeve 798 extending from the forward location 792. The opposite portion of the deployed electrode 796 slidably extends within a flexible sleeve 800 protruding from the rearward location 794 and in communication, as before, with an electrode guide as described at 134 in connection with FIGS. 11 and 12. Positioned rearwardly and in adjacency with the deployed electrode 796 is a surface mounted electrode 802. With the arrangement shown, during electrosurgical cutting and deployment of electrode 796, that electrode is operated in monopolar fashion, for example, with a remotely positioned electrode such as described at 74, FIG. 1. Preferably, however this monopolar-based deployment is carried out with electrode 802 connected as an electrosurgical return. During cauterization procedures, the volume of tissue to be cauterized will be located within a current flux path represented by the dashed line array 804.

The electrosurgically deployed electrodes of the instruments of the invention have applications in a variety of therapies wherein a diminutive size is called for. Additionally, the instruments may be called upon to carry out cauterization in tissue regions which are benign, i.e., regions which do not constitute a neoplasm. In this regard, the devices may be utilized to cauterize volumes of prostatic tissue as a treatment for urethral blockage encountered with benign prostatic hyperplasia (BPH). Referring to FIG. 40 (which is located below FIG. 22) benign prostatic tissue is represented at 810. The lumen or canal of the urethra is represented at 812 having a boundary or lining 814. An instrument represented generally at 820 is shown extending within the urethral canal 812. The instrument 820 may be a steerable endoscopic delivery system such as common cystoscope which is fiber optically guided. Instrument 820 is shown as having a flexible portion 822 from which extends a more resilient, forward end region 824. Region 824 which is rigid only adjacent the outer end of the instrument has been inserted through the urethral lining 814 and into the tissue 810. A trocar tip 826 is located at the forward end of the region 824 and behind that tip are four electrosurgically deployed electrodes 828–831. For electrosurgical deployment, electrodes 828–831 perform in monopolar fashion in conjunction with a remote large surface patient return electrode such as described at 74 in FIG. 1. Upon full deployment, then adjacently disposed or paired electrodes perform in bipolar biactive fashion, one being at a higher potential than the other. In this regard, electrode 828 may perform in conjunction with electrode 829 and electrode 830 may perform in conjunction with electrode 831. The result is a spherical or ellipsoidal zone of cauterization the boundary of which is represented at 834. Inasmuch as no malignancy is involved in this procedure, the electrodes need not be positioned in some form of adjacency with the tissue volume to be cauterized. By utilizing a multiplicity of electrodes as at 828–831, the procedure can be carried out advantageously faster. Typically, such zones of necrosis will number from four to eight and are found effective in reducing the progress of swelling of tissue 810 and may beneficially effect some minor shrinkage. Following cauterization procedures, the electrodes 828–831 are retracted to their nested orientation as described in conjunction with FIG. 5 and the instrument 820 is then removed or repositioned for a repeat of the procedure.

Referring to FIGS. 41 and 42, another embodiment of the instrument of the invention, particularly suited for the cauterization of diminutive tissue volumes is revealed. The forward end region of the instrument is shown in the figures in general at 840, extending to a trocar type tip 842. Similar to the arrangement of FIG. 38, the forward region 840 incorporates a deployment portion having two guidance channels shown in phantom at 844 and 846 extending to respective guidance ports 848 and 850. Within the channels 844 and 846 are two resilient wire electrodes shown respectively at 852 and 854. The guidance channels and guidance ports are configured such that the outward deployment of electrodes 852 and 854 is generally forwardly of the tip 842 and angularity translatively outwardly to generate a form of "v". Additionally, as seen in FIG. 42, the electrodes extend upwardly at an angle θ respect to the longitudinal axis 856 of the forward region 840. Electrodes 852 and 854 are configured for electrosurgical cutting activity during their employment and further, it may be noted that the electrodes are insulated with an electrically insulative sleeve portion 858 surmounting electrode 852 and a sleeve 860 surmounting electrode 854. Angle, θ may fall within a range from about 5° to 90° and preferably from about 10° to 60°. The electrically insulative sleeves 858 and 860 serve to localize the active surfaces of the biactive electrode 852 and 854 during cauterization. In general, as shown at the array of dashed current flux lines identified generally at 852 in FIG. 33, the zone of cauterization is developed as a thin ellipsoid.

Since certain changes may be made in the above-described apparatus, method and system without departing from the scope of the invention herein involved, it is intended that all matter contained in the description thereof or shown in the accompanying drawings shall be interpreted as illustrative and not in a limiting sense.

What is claimed is:

1. Apparatus for carrying out the cauterization of a volume of abnormal tissue of given peripheral extent utilizing the applied electrical outputs, including a return, of an electrosurgical generator, comprising:

a support member extending between a tip and a base region, having a forward end region extending along a longitudinal axis from said tip and positionable in an insertion mode into adjacency with said tissue volume peripheral extent, said forward end region having an electrode deployment portion;

a first electrode assembly, having a primary component of predetermined longitudinal dimension extending within said deployment portion in said insertion mode, deployable, in an electrosurgical cutting deployment mode, outwardly from said electrode deployment portion to a first cauterization orientation adjacent said tissue peripheral extent; and an actuator and electrical circuit assembly extending along said support member from said base region, mechanically connected with said first electrode primary component for effecting said deployment thereof, and having a terminal assembly electrically connectable with said generator for coupling a first said applied output to said first electrode primary component providing, in operative association with a said return, electrosurgical cutting of tissue adjacent said peripheral extent during said electrosurgical cutting deployment mode, said terminal assembly conveying a second said applied output from said generator as a cauterization current to said first electrode assembly when said first electrode primary component is at said first cauterization orientation.

2. The apparatus of claim 1 including:

a second electrode assembly having a primary component of predetermined longitudinal dimension extending within said electrode deployment portion in said insertion mode, deployable in an electrosurgical cutting deployment mode, outwardly from said electrode deployment portion to a second cauterization orientation adjacent said tissue peripheral extent and spaced a cauterization distance from said first electrode assembly when at said first cauterization orientation; and said actuator and electrical circuit assembly is mechanically connected with said second electrode assembly for effecting said deployment thereof, and said terminal assembly is configured for coupling said first applied output to said second electrode primary component during an electrosurgical cutting deployment mode.

3. The apparatus of claim 2 in which:

said actuator and electrical circuit assembly is configured for coupling said second applied output across said first and second electrode assemblies when said second electrode assembly is at said second cauterization orientation and said first electrode assembly is at said first cauterization orientation to effect passage of said cauterization current between said first and said second electrode assemblies.

4. The apparatus of claim 1 including:

a return electrode mounted upon said support member at a location for electrical coupling association with said tissue; and said actuator and electrical circuit assembly terminal assembly is configured for coupling said return to said return electrode during said electrosurgical cutting deployment mode.

5. The apparatus of claim 4 in which said actuator and electrical circuit assembly terminal assembly is configured for coupling said second applied output across said first electrode assembly and said return electrode when said first electrode assembly is in said first cauterization orientation.

6. The apparatus of claim 5 in which said return electrode is positioned at said forward end region.

7. The apparatus of claim 1 in which:

said first electrode assembly includes a secondary electrode electrically insulated from and deployable with said first electrode assembly primary component to said first cauterization orientation and exhibiting an electrically conductive surface of area extent substantially greater than the corresponding electrically conductive surface area extent of said first electrode assembly primary component; and said actuator and electrical circuit assembly effects deployment of said secondary electrode with said first electrode assembly primary component and said terminal assembly conveys said second applied output to said secondary electrode.

8. The apparatus of claim 1 in which:

said forward end region electrode deployment portion is outwardly open, extending along said forward end region between a forward location adjacent to said tip and a rearward location;

a first electrode primary component is thin and elongate, having a distal end connected with said support member at a connection location adjacent said forward location and extending an arch defining distance beyond said rearward location; and said actuator and electrical circuit assembly is configured to mechanically deploy said first electrode primary component by urging it forwardly in compression to effect movement generally transversely to said longitudinal axis to an extent curving it into an outwardly depending arch formation extending between said forward location and said rearward location.

9. The apparatus of claim 8 in which said first electrode assembly comprises:

a thin membranous flexible secondary electrode support, suspended from said first electrode primary component substantially between said forward location and said rearward location and having panels defined by spaced apart slots;

a first secondary electrode provided as an electrically conductive surface supported upon said support panels and coupled with said terminal assembly for receiving said second applied output; and said secondary electrode being foldably nested within said electrode deployment portion during said insertion mode; and depending from said primary component toward said deployment portion when said primary component is in said first cauterization orientation.

10. The apparatus of claim 9 in which:

said secondary electrode support includes an edge region and exhibits a predetermined thickness;

said first electrode assembly primary component is provided as a tube with an internal cavity of given principal dimension and having an elongate slot therein of width corresponding with said predetermined thickness; and said secondary electrode support edge region extends through said slot and is retained within said internal cavity.

11. The apparatus of claim 10 in which:

said secondary electrode support edge region is of border dimension less than said given principal dimension, has an edge region thickness greater than said slot width, and is slideably retained within said tube internal cavity.

12. The apparatus of claim 9 in which said secondary electrode support panels are configured with edges defined by said slots which slope toward said rearward location an amount effective to induce a wrapping thereof about said forward end region when said support member is withdrawn from adjacency with said tissue volume.

13. The apparatus of claim 8 in which said first electrode assembly is electrically insulated from said support member adjacent said forward location and adjacent said rearward location.

14. The apparatus of claim 8 in which:

said support member includes a deflector guide component located within said electrode deployment portion intermediate said forward location and said rearward location; and said first electrode primary component is positioned in freely abutting outwardly biased relationship with said deflector guide component during said insertion mode.

15. The apparatus of claim 1 in which:

said support member electrode deployment portion comprises a guidance port defining a guidance channel having a guidance translation extending generally transversely outwardly from said longitudinal axis; and said first electrode assembly primary component comprises a resilient wire extending within said electrode deployment portion, having a distal end aligned during said insertion mode for deployment through said guidance port, and actuable for deployment through said guidance port during said electrosurgical cutting deployment mode.

16. The apparatus of claim 1 in which:

said support member electrode deployment portion comprises a guidance port in communication with a guidance channel with a guidance translation extending generally forwardly from said tip; and said first electrode assembly primary component comprises a resilient wire extending within said electrode deployment portion, having a distal end aligned during said insertion mode for deployment through said guidance port, and deployable generally forwardly from said tip through said guidance port to said first cauterization position.

17. The apparatus of claim 16 in which said first electrode assembly primary component, when deployed to said first cauterization position, is upwardly angularly oriented an angle, θ, with respect to said longitudinal axis; and said angle, θ, is within a range of about 5° to 90°.

18. A system for carrying out the cauterization of a volume of abnormal tissue, said abnormal tissue exhibiting a given peripheral extent, comprising:

an electrosurgical generator assembly having an electrosurgical return, responsive to a first control input to generate a first current defined output for carrying out electrosurgical cutting, responsive to a second control input to generate a second current defined output for carrying out cauterization and having an electrosurgical return;

a support member extending between a tip and a base region, having a forward end region extending along a longitudinal axis from said tip and positionable in an insertion mode into adjacency with said tissue volume peripheral extent, and having an electrode deployment portion adjacent said tip, a first electrode assembly having a first primary component of predetermined longitudinal dimension, extending within said support member deployment portion during said insertion mode, deployable to move outwardly from said electrode deployment portion to a first cauterization orientation adjacent said tissue peripheral extent;

an actuator assembly extending along said support member from said base region, mechanically connected with said first electrode assembly and actuable for effecting the said deployment thereof; and a control assembly in electrical communication with said electrosurgical generator assembly and said first electrode assembly, actuable in correspondence with said first electrode assembly deployment to effect derivation of said first control input and the application of said first current defined output to said first electrode assembly first primary component in electrical association with said electrosurgical return in correspondence with said first electrode assembly deployment toward said first cauterization orientation, subsequently actuable to effect derivation of said second control input and the application of said second current defined output to said first electrode assembly when said first electrode assembly is in said cauterization orientation.

19. The system of claim 18 including:

a second electrode assembly having a second primary component of predetermined longitudinal dimension extending within said electrode deployment portion during said insertion mode, deployable to move outwardly from said electrode deployment portion to a second cauterization orientation adjacent said tissue peripheral extent and spaced from said first electrode assembly when said first electrode assembly is at said first cauterization orientation;

said actuator assembly is mechanically connected with said second electrode assembly and actuable for effecting the said deployment thereof; and said control assembly is in electrical communication with said second electrode assembly, actuable in the presence of said first control input to effect application of said first current defined output to said second electrode assembly second primary component in electrical association with said electrosurgical return in correspondence with said second electrode assembly deployment toward said second cauterization orientation.

20. The system of claim 19 in which:

said control assembly, in correspondence with said subsequent actuation, is configured for coupling said second current defined output across said first and second electrode assemblies to carry out cauterization of said abnormal tissue.

21. The system of claim 19 in which:

said first electrode assembly includes a first secondary electrode electrically isolated from and deployable with said first electrode assembly first primary component to said first cauterization orientation and exhibiting an electrically conductive surface of surface area extent substantially greater than the corresponding surface area extent of said first primary component;

said second electrode assembly includes a second secondary electrode electrically isolated from and deployable with said second electrode assembly second primary component to said second cauterization orientation and exhibiting an electrically conductive surface of surface area extent substantially greater than the corresponding surface area extent of said second primary component;

said actuator assembly actuator effects said first and second secondary electrode deployment; and said control assembly, in correspondence with said subsequent actuation, is configured for coupling said second current defined output across said first and second secondary electrodes to carry out cauterization of said abnonnal tissue.

22. The system of claim 18 including:

a return electrode mounted upon said support member at a location in electrical coupling association with said tissue when said first electrode assembly is deployed toward said first cauterization orientation; and said control assembly is responsive to apply said electrosurgical return to said return electrode when said first electrode assembly is deployed toward said first cauterization orientation.

23. The system of claim 22 in which said control assembly is responsive to apply said second current defined output across said first electrode assemblies and said return electrode.

24. The system of claim 23 in which said return electrode is located in proximity to said forward end region.

25. The system of claim 18 in which:

said first electrode assembly includes a first secondary electrode electrically isolated from and deployable with said first electrode assembly first primary component to said cauterization orientation and exhibiting an electrically conductive surface of surface area extent substantially greater than the corresponding surface area extent of said first primary component;

said actuator assembly actuation effects said first secondary electrode deployment; and said control assembly subsequent actuation effects application of said second current defined output to said first secondary electrode.

26. The system of claim 18 in which:
said support member electrode deployment portion is outwardly open, extending along said forward end region between a forward location adjacent to said tip and a rearward location;
said first electrode assembly first primary component is thin, elongate and resilient, having a distal end connected with said support member at a connection location adjacent said forward location and extending an arch defining distance beyond said rearward location; and
said actuator assembly is configured to deploy said first electrode first primary component by urging it forwardly in compression to effect movement thereof generally transversely to said longitudinal axis to an extent curving it into an outwardly depending arch formation extending between said forward location and said rearward location.

27. The system of claim 26 in which said first electrode assembly first primary component is electrically insulated from said support member adjacent said forward location and adjacent said rearward location.

28. The system of claim 26 in which:
said support member includes a deflector guide component located within said electrode deployment portion intermediate said forward location and said rearward location; and
said first electrode assembly first primary component is positioned in freely abutting outwardly biased relationship with said deflector guide component during said insertion mode.

29. The system of claim 26 in which:
said first electrode assembly includes an array of electrically conductive flat panel shaped first secondary electrodes, each having an outwardly disposed edge connected in electrically isolative association with said first electrode first primary component, said first secondary electrodes depending from said first electrode first primary component toward said deployment portion when said first electrode first primary component is in said first cauterization orientation, and being nestably retained within said support member electrode deployment portion during said insertion mode.

30. The system of claim 26 in which:
said first electrode assembly comprises:
a thin membranous flexible polymeric first secondary electrode support, suspended from said first primary component substantially between said forward location and said rearward location and having slot defined panels;
a first secondary electrode provided as an electrically conductive surface supported upon said first secondary electrode support panels; and
said first secondary electrode being foldably nested with said first secondary electrode support within said electrode deployment portion during said insertion mode, and depending from said first primary component toward said deployment portion when said first primary component is in said first cauterization orientation.

31. The system of claim 30 in which:
said first secondary electrode support includes an edge region and exhibits a predetermined thickness;
said first primary component is provided as a tube with an internal cavity of given principal dimension, and having an elongate slot therein of width corresponding with said predetermined thickness; and
said secondary electrode support edge region extends through said slot and is retained within said internal cavity.

32. The system of claim 31 in which:
said first secondary electrode support edge region is of border dimension less than said given principal dimension, has an edge region thickness greater than said slot width, and is slidably retained within said tube internal cavity.

33. The system of claim 30 in which said first secondary electrode support panels extend along said first primary component substantially from said forward location to said rearward location when said first primary component is within said deployment portion in said insertion mode.

34. The system of claim 30 in which said slot defined panels are configured with slot defined edges sloping toward said rearward location an amount effective to induce a wrapping thereof about said forward end region when said support member is withdrawn from adjacency with said tissue volume peripheral extent.

35. The system of claim 26 in which:
said first electrode assembly includes an array of thin, flexible electrically conductive first secondary electrodes each having an outer end connected in electrically isolative association with the first electrode first primary component and having an inner end connected within said deployment portion, said first secondary electrodes extending from said first electrode first primary component into said deployment portion when said first electrode first primary component is in said first cauterization orientation, and being retained within said support member electrode deployment portion during said insertion mode.

36. The system of claim 26 in which:
said support member includes an elongate mandrel mounted for rotation within said electrode deployment portion;
said first electrode assembly including a thin sheet-form electrically conductive secondary electrode having an arcuately shaped outer edge and inward edge connected with said mandrel, said secondary electrode being wound about said mandrel and retained within said electrode deployment portion during said insertion mode; and
said actuator assembly is mechanically connected with said mandrel and is actuable to rotate said mandrel to deploy said secondary electrode from said deployment portion.

37. The system of claim 26 in which:
said first electrode assembly includes a thin, elongate secondary electrode having a distal end connected with said support member at a connection location adjacent said forward location and extending a secondary arch defining distance less than said first electrode arch defining distance beyond said rearward location;
said actuation assembly is configured to deploy said secondary electrode by urging it forwardly in compression to effect movement thereof generally transversely to said longitudinal axis to an extent curving it into an outwardly depending arch formation extending substantially between said forward location and said rearward location; and
said control assembly is electrically coupled with said secondary electrode and is responsive to effect application of said second current defined output thereto.

38. The system of claim 18 in which:

said support member electrode deployment portion comprises a guidance port and a guidance channel having a guidance translation extending generally transversely outwardly from said longitudinal axis; and said first electrode assembly first primary component comprises a resilient wire extending within said electrode deployment portion, having a distal end aligned during said insertion mode for deployment through said guidance port, and deployable through said guidance port to said first cauterization orientation adjacent said tissue peripheral extent.

39. The apparatus of claim 18 in which:

said support member electrode deployment portion comprises a guidance port in communication with a guidance channel with a guidance translation extending generally forwardly from said tip; and said first electrode assembly first primary component comprises a resilient wire extending within said electrode deployment portion, having a distal end aligned during said insertion mode for deployment through said guidance port, and deployable generally forwardly from said tip through said guidance port to said first cauterization position.

40. The apparatus of claim 39 in which said first electrode assembly, when deployed to said first cauterization position, is upwardly angularly oriented an angle, θ, with respect to said longitudinal axis; and said angle, θ, is within a range of about 5° to 90°.

41. The system of claim 18 in which:

said first electrode assembly first primary component is configured having predetermined length and principal cross sectional dimension;

said control assembly includes an electrical coding component mounted with said support member and exhibiting an electrical parameter corresponding with said predetermined dimension;

said electrosurgical generator includes a decoding circuit electrically coupled with said control assembly, responsive to electrically interrogate said electrical coding component to derive a corresponding selection signal, and is responsive to said selection signal to generate predetermined said first current defined output and second current defined output corresponding with said predetermined dimensions.

42. The system of claim 18 in which:

said control assembly includes a temperature sensor mounted upon said support member at said forward end region and having a temperature output condition corresponding with the temperature of tissue in adjacency with it; and said electrosurgical generator includes a temperature logic circuit responsive to said temperature output condition and a predetermined first temperature value condition to derive a first control condition, said electrosurgical generator further including a control logic circuit responsive to said first control condition to modulate said first current defined output in correspondence therewith.

43. The system of claim 18 in which:

said control assembly includes a temperature sensor mounted upon said support member at said forward end region and having a temperature output condition corresponding with the temperature of tissue in adjacency with it; and said electrosurgical generator includes a temperature logic circuit responsive to said temperature output condition and a predetermined second temperature value condition to derive a second control condition, to modulate said second current defined output in correspondence therewith.

44. The system of claim 18 in which:

said control assembly includes a temperature sensor mounted upon said support member at said forward end region and having a temperature output condition corresponding with the temperature of tissue in adjacency with it; and said electrosurgical generator includes a temperature logic circuit responsive to said temperature output condition and a predetermined third temperature value condition corresponding with the necrosis of said abnormal tissue to derive a third control condition, said generator including a control logic circuit responsive to said third control condition to terminate generation of said second current defined output.

45. The system of claim 18 in which:

said control assembly includes a temperature sensor mounted upon said support member at said forward end region and having a temperature output condition corresponding with the temperature of tissue in adjacency with it;

said electrosurgical generator includes:

a display assembly responsive to a display input signal to provide a perceptible output cueing a procedure termination, a temperature logic circuit responsive to said temperature output condition and a predetermined third temperature value condition corresponding with the necrosis of said abnormal tissue to derive a third control condition, and a control logic circuit responsive to said third control condition to derive said display input signal.

46. A method for cauterizing targeted abnormal tissue of a patient, said tissue having a given volume and peripheral extent, comprising the steps of:

(a) providing an electrosurgical generator assembly having an electrosurgical return, controllable to generate a first current defined output for carrying out electrosurgical cutting of tissue, and to generate a second current defined output for carrying out the cauterization of said abnormal tissue;

(b) providing an instrument electrically coupled with said electrosurgical generator, having a support member extending between a tip and a base region, having a forward end region with first and second electrode assemblies having a nested orientation for movement of said forward end region with respect to said tissue, actuable for outward, spaced apart deployment from said forward end region to corresponding first and second deployed orientations and futher actuable to retract toward said nested orientation;

(c) positioning said instrument forward end region in adjacency with said tissue peripheral extent, with said first and second electrodes assemblies in said nested orientation;

(d) actuating said instrument to deploy said first electrode assembly outwardly to a first cauterizing orientation in adjacency with said tissue peripheral extent;

(e) simultaneously with said step (d) controlling said electrosurgical generator assembly to apply said first current defined output to said first electrode in electrical association with said return during said first electrode assembly deployment;

(f) actuating said instrument to deploy said second electrode assembly outwardly to a second cauterizing orientation spaced from said first cauterizing orientation and in adjacency with said tissue peripheral extent;

(g) simultaneously with said step (f), controlling said electrosurgical generator assembly to apply said first current defined output to said second electrode assembly in electrical association with said return during said second electrode assembly deployment;

(h) controlling said electrosurgical generator assembly to apply said second current defined output across said first and second electrode assemblies, for an interval effective to cauterize said abnormal tissue;

(i) actuating said instrument to retract said first electrode assembly toward said nested orientation;

(j) actuating said instrument to retract said second electrode assembly into said nested orientation; and (k) removing said instrument forward end region from adjacency with said tissue peripheral extent.

47. The method of claim 46 wherein said steps (d) through (g) are carried out substantially simultaneously.

48. The method of claim 46 in which:

said electrosurgical return is provided as a patient return electrode having an extended surface area for atraumatic contact with tissue at a location remote from said targeted abnormal tissue;

including the step of: positioning said patient return electrode in a skin contacting relationship with said patient, and said steps (e) and (g) are carried out in electrosurgically monopolar fashion.

49. The method of claim 46 in which:

said electrosurgical return is provided comprising a return electrode mounted upon said support member at a location in electrical coupling association with said tissue when said forward end region is positioned in adjacency with said tissue peripheral extent; and said steps (e) and (g) are carried out in electrosurgically monopolar fashion.

50. The method of claim 49 in which said step (h) is carried out by applying said second current defined output across said first electrode assembly and said return electrode and across said second electrode assembly and said return electrode.

51. The method of claim 50 in which said second current defined output is applied simultaneously across said first and second electrode assemblies and said return electrode.

52. The method of claim 46 in which:

said instrument is provided having a temperature sensor mounted upon said support member at said forward end region and having a temperature output condition corresponding with the temperature of tissue in adjacency with it; and said step (h) application of said second current defined output is carried out until said temperature output condition corresponds with an effective cauterization of said abnormal tissue.

53. The method of claim 46 in which:

said steps (d) and (f) are carried out by deploying respective said first and second electrode assemblies to a sequence of incrementally outward said first and second cauterizing orientations from first to last; and said step (h) is carried out following movement of said first and second electrode assemblies to each said incrementally outward orientation from first to last.

54. The method of claim 46 in which:

said instrument is provided having a temperature sensor mounted upon said support member at said forward end region and having a temperature output condition corresponding with the temperature of tissue in adjacency with it; and said steps (e) and (g) include the steps of monitoring said temperature output condition and controlling said electrosurgical generator to maintain the temperature of tissue in contact with said first and second electrodes during said deployment thereof below about 75° C.

55. A method for cauterizing targeted abnormal tissue of a patient, said tissue having a given volume and peripheral extent, comprising the steps of:

(a) providing an electrosurgical generator assembly having an electrosurgical return, controllable to generate a first current defined output for carrying out electrosurgical cutting of tissue, and to generate a second current defined output for carrying out the cauterization of said abnormal tissue;

(b) providing an instrument electrically coupled with said electrosurgical generator assembly, having a support member extending between a tip and a base region, having a forward end region with a deployable first electrode assembly having a nested orientation for movement of said forward end region with respect to said tissue, actuable for outward deployment from said forward end region to a cauterizing orientation and futher actuable to retract toward said nested orientation, and having a surface mounted electrode in electrical communication with said electrosurgical return mounted upon said support member at a location for electrical coupling association with said tissue;

(c) positioning said instrument forward end region in adjacency with said abnormal tissue peripheral extent, with said first electrode assembly in said nested orientation and said surface mounted electrode in said electrical coupling association with said tissue peripheral extent;

(d) actuating said instrument to deploy said first electrode assembly outwardly to said cauterizing orientation in adjacency with said abnormal tissue peripheral extent;

(e) simultaneously with said step (d), controlling said electrosurgical generator assembly to apply said first current defined output to said first electrode in electrical association with said electrosurgical return through said second electrode during said deployment;

(f) controlling said electrosurgical generator assembly to apply said second current defined output across said first electrode assembly and said surface mounted electrode for an interval effective to cauterize said abnormal tissue;

(g) actuating said instrument to retract said first electrode toward said nested orientation; and (h) removing said instrument forward portion from adjacency with said tissue peripheral extent.

56. The method of claim 55 in which:

said instrument is provided having a temperature sensor mounted upon said support member at said forward end region and having a temperature output condition corresponding with the temperature of tissue in adjacency with it; and said step (f) application of said second current defined output is carried out until said temperature output condition corresponds with an effective cauterization of said abnormal tissue.

57. The method of claim 55 in which:
said step (d) is carried out by deploying said first electrode assembly to a sequence of incrementally outward cauterizing orientations from first to last; and
said step (f) is carried out following movement of said first electrode assembly to each said incrementally outward orientation from first to last.

58. The method of claim 55 in which:
said instrument is provided having a temperature sensor mounted upon said support member at said forward end region and having a temperature output condition corresponding with the temperature of tissue in adjacency with it; and
said steps (e) includes the step of monitoring said temperature output condition and controlling said electrosurgical generator to maintain the temperature of said electrode below about 75° C. during said deployment thereof.

59. Apparatus for carrying out the cauterization of a volume of tissue utilizing the applied electrical output, including a return, of an electrosurgical generator, comprising:
a support member extending between a tip and a rear region, having a forward end region extending along a longitudinal axis from said tip and positionable in an insertion mode at a location for the electrosurgical cutting of tissue, said forward end region having a first deployment assembly;
a first electrode of predetermined longitudinal dimension extending within said first deployment assembly in said insertion mode, deployable, in an electrosurgical cutting mode, outwardly from said electrode first deployment assembly to a first cauterization orientation for effecting cauterization of said volume of tissue; and
an actuator and electrical circuit assembly extending along said support member from said rear region, mechanically connected with said first electrode for effecting said deployment thereof, and having a terminal assembly connectable with said generator for coupling a first said applied output to said first electrode providing, in operative association with said return, localized electrosurgical cutting of said tissue in contact with said first electrode during said electrosurgical cutting mode, said terminal assembly conveying a second said applied output from said generator as a cauterization current to said first electrode when said first electrode is at said first cauterization orientation.

60. The apparatus of claim 59 including:
a second electrode of predetermined longitudinal dimension extending, during said insertion mode, within a second electrode deployment assembly of said forward end region spaced from said first electrode deployment assembly, the said second electrode being deployable in an electrosurgical cutting mode outwardly from said second electrode deployment assembly to a second cauterization orientation spaced a cauterization distance from said first electrode when at said first cauterization orientation; and
said actuator and electrical circuit assembly is mechanically connected with said second electrode for effecting said deployment thereof, and said terminal assembly is configured for coupling said first applied output to said second electrode during an electrosurgical cutting mode.

61. The apparatus of claim 60 in which:
said actuator and electrical circuit assembly is configured for coupling said second applied output across said first and second electrodes when said second electrode is at said second cauterization orientation and said first electrode is at said first cauterization orientation.

62. The apparatus of claim 61 including:
a third electrode of predetermined longitudinal dimension extending, during said insertion mode within a third electrode deployment assembly of said forward end region, spaced from said first and second electrode deployment assemblies, said third electrode being deployable in an electrosurgical cutting mode outwardly from said third electrode deployment assembly to a third cauterization orientation;
a fourth electrode of predetermined longitudinal dimension extending, during said insertion mode, within a fourth electrode deployment assembly of said forward end region, said fourth electrode deployment assembly being spaced from said third electrode deployment assembly, said fourth electrode being deployable in an electrosurgical cutting mode outwardly from said fourth electrode deployment assembly to a fourth cauterization orientation spaced a cauterization distance from said third electrode when at said third cauterization orientation; and
said actuator and electrical circuit assembly is mechanically connected with said third and fourth electrodes for effecting said deployment thereof, and said terminal assembly is configured for coupling said first applied output to said third and fourth electrodes during an electrosurgical cutting mode.

63. The apparatus of claim 62 in which:
said actuator and electrical circuit assembly is configured for coupling said second applied output across said third and fourth electrodes when said third electrode is at said third cauterization orientation and said fourth electrode is at said fourth cauterization orientation.

64. The apparatus of claim 63 in which:
said first, second, third and fourth electrode deployment assemblies are outwardly open, extending along said forward end region between a forward location adjacent said tip and a rearward location;
each said first, second, third and fourth electrodes is thin and elongate, having a distal end connected with said support member at a connection location adjacent said forward location and extending an arch defining distance beyond said rearward location; and
said actuator and electrical circuit assembly is configured to deploy each said first, second, third and fourth electrode by urging it forwardly in compression to effect movement generally transversely to said longitudinal axis to an extent curving it into an outwardly depending arch formation extending between said forward location and said rearward location.

65. The apparatus of claim 64 in which each said first, second, third and fourth electrode is electrically insulated from said support member adjacent said forward location and said rearward location.

66. The apparatus of claim 64 including:
a deflector guide component mounted within said support member forward end region and providing a component of said first, second, third and fourth deployment assemblies; and
each said first, second, third and fourth electrode is positioned in freely abutting outwardly biased relationship with said deflector guide component during said insertion mode.

67. The apparatus of claim 59 including:
a return electrode mounted upon said support member at a location for electrical coupling association with said tissue; and
said actuator and electrical circuit assembly terminal assembly is configured for coupling said return to said return electrode during said electrosurgical cutting mode.

68. The apparatus of claim 67 in which said actuator and electrical circuit assembly terminal assembly is configured for coupling said second applied output across said first electrode and said return electrode when said first electrode is in said first cauterization orientation.

69. The apparatus of claim 68 in which said return electrode is positioned at said forward end region.

70. The apparatus of claim 59 in which:
said first electrode deployment assembly comprises a guidance port defining a guidance channel having a guidance translation extending generally transversely outwardly from said longitudinal axis; and
said first electrode comprises a resilient wire extending within said first electrode deployment assembly, having a distal end aligned during said insertion mode for deployment through said guidance port, and actuable for deployment through said guidance port during said electrosurgical cutting mode.

71. The apparatus of claim 59 in which:
said first electrode deployment assembly comprises a guidance port in communication with a guidance channel with a guidance translation extending generally forwardly from said tip; and
said first electrode comprises a resilient wire extending within said first electrode deployment portion, having a distal end aligned during said insertion mode for deployment through said guidance port, and deployable generally forwardly from said tip through said guidance port to said first cauterization position.

72. The apparatus of claim 71 in which said first electrode, when deployed to said first cauterization position, is upwardly angularly oriented an angle, θ, with respect to said longitudinal axis; and
said angle, θ, is within a range of about 5° to 90°.

73. A system for carrying out the cauterization of a volume of tissue, comprising;
an electrosurgical generator assembly responsive to a first control input to generate a first current defined output for carrying out electrosurgical cutting, responsive to a second control input to generate a second current defined output for carrying out cauterization and having an electrosurgical return;
a support member extending between a tip and a rear region, having a forward end region extending along a longitudinal axis from said tip and positionable in an insertion mode at a select location within said tissue and having an electrode deployment portion adjacent said tip,
a first electrode of predetermined longitudinal dimension, extending within said deployment portion during said insertion mode, deployable to move outwardly from said electrode deployment portion to a first cauterization orientation within said tissue;
an actuator assembly extending along said support member from said rear region, mechanically connected with said first electrode and actuable for effecting the said deployment thereof; and
a control assembly in electrical communication with said electrosurgical generator assembly and said first electrode, actuable in correspondence with said first electrode deployment to effect derivation of said first control input and the application of said first current defined output to said first electrode in electrical association with said electrosurgical return simultaneously with said first electrode deployment toward said first cauterization orientation, subsequently actuable to effect derivation of said second control input and the application of said second current defined output to said first electrode when said first electrode is in said cauterization orientation.

74. The system of claim 73 including:
a second electrode of predetermined longitudinal dimension extending within said electrde deployment portion during said insertion mode, deployable to move outwardly from said electrode deployment portion to a second cauterization orientation within said tissue and spaced from said first electrode when said first electrode is at said first cauterization orientation;
said actuator assembly is mechanically connected with said second electrode and actuable for effecting the said deployment thereof; and
said control assembly is in electrical communication with said second electrode, actuable in the presence of said first control input to effect application of said first current defined output to said second electrode in electrical association with said electrosurgical return simultaneously with said second electrode deployment toward said second cauterization orientation.

75. The system of claim 74 in which:
said control assembly, in correspondence with said subsequent actuation, is configured for coupling said second current defined output across said first and second electrodes to carry out cauterization of said tissue.

76. The system of claim 75 including:
a third electrode of predetermined longitudinal dimension extending, during said insertion mode, within said electrode deployment portion, spaced from said first and second electrodes and deployable to move outwardly from said electrode deployment portion to a third cauterization orientation;
a fourth electrode of predetermined longitudinal dimension extending, during said insertion mode within said electrode deployment portion, spaced from said third electrode and deployable to move outwardly from said electrode deployment portion to a fourth cauterization orientation spaced a cauterization distance from said third electrode when at said third cauterization orientation; and
said control assembly is in electrical communication with said third and fourth electrodes, actuable in the presence of said first control input to effect application of said first current defined output to said third and fourth electrodes in electrical association with said electrosurgical return simultaneously with said third and fourth electrode deployment toward respective said third and fourth cauterization orientations.

77. The system of claim 76 in which:
said control assembly, in correspondence with said subsequent actuation, is configured for coupling said second current defined output across said third and fourth electrodes to carry out cauterization of said tissue.

78. The system of claim 73 including:
a return electrode mounted upon said support member at a location in electrical coupling association with said tissue when said first electrode is deployed toward said first cauterization orientation; and said control assembly is responsive to apply said electrosurgical return to said return electrode when said first electrode is deployed toward said first cauterization orientation.

79. The system of claim 78 in which said control assembly is responsive to apply said second current defined output across said first and return electrodes.

80. The system of claim 79 in which said return electrode is located in proximity to said forward end region.

81. The system of claim 73 in which:

said support member electrode deployment portion is outwardly open, extending along said forward end region between a forward location adjacent to said tip and a rearward location;

said first electrode is thin, elongate and resilient, having a distal end connected with said support member at a connection location adjacent said forward location and extending an arch defining distance beyond said rearward location; and said actuator assembly is configured to deploy said first electrode by urging it forwardly in compression to effect movement thereof generally transversely to said longitudinal axis to an extent curving it into an outwardly depending arch formation extending between said forward location and said rearward location.

82. The system of claim 81 in which said first electrode is electrically insulated from said support member adjacent said forward location and adjacent said rearward location.

83. The system of claim 81 in which:

said support member includes a deflector guide component located within said electrode deployment portion intermediate said forward location and said rearward location; and said first electrode is positioned in freely abutting outwardly biased relationship with said deflector guide component during said insertion mode.

84. The system of claim 81 in which:

said first electrode includes an array of electrically conductive flat panel shaped secondary electrodes, each having an outwardly disposed edge connected in electrically conductive association with said first electrode, said secondary electrodes depending from said first electrode toward said deployment portion when said first electrode is in said first cauterization orientation, and being nestably retained within said support member electrode deployment portion during said insertion mode.

85. The system of claim 81 in which:

said first electrode includes an array of thin, flexible electrically conductive secondary electrodes each having an outer end connected in electrically conductive association with the first electrode and having an inner end connected within said deployment portion, said secondary electrodes extending from said first electrode into said deployment portion when said first electrode is in said first cauterization orientation, and being retained within said support member electrode deployment portion during said insertion mode.

86. The system of claim 81 in which:

said first electrode includes a thin, elongate secondary electrode having a distal end connected with said support member at a connection location adjacent said forward location and extending a secondary arch defining distance less than said first electrode arch defining distance beyond said rearward location;

said actuation assembly is configured to deploy said secondary electrode by urging it forwardly in compression to effect movement thereof generally transversely to said longitudinal axis to an extent curving it into an outwardly depending arch formation extending substantially between said forward location and said rearward location; and said control assembly is electrically coupled with said secondary electrode and is responsive to effect application of said second current defined output thereto.

87. The system of claim 73 in which:

said support member electrode deployment portion comprises a guidance port and a guidance channel having a guidance translation extending generally transversely outwardly from said longitudinal axis; and said first electrode comprises a resilient wire extending within said electrode deployment portion, having a distal end aligned during said insertion mode for deployment through said guidance port, and deployable through said guidance port to said first cauterization orientation adjacent said tissue peripheral extent.

88. The apparatus of claim 73 in which:

said support member electrode deployment portion comprises a guidance port in communication with a guidance channel with a guidance translation extending generally forwardly from said tip; and said first electrode comprises a resilient wire extending within said electrode deployment portion, having a distal end aligned during said insertion mode for deployment through said guidance port, and deployable generally forwardly from said tip through said guidance port to said first cauterization position.

89. The apparatus of claim 88 in which said first electrode, when deployed to said first cauterization position, is upwardly angularly oriented an angle, $\theta$, with respect to said longitudinal axis; and said angle, $\theta$, is within a range of about 5° to 90°.

90. The system of claim 73 in which:

said first electrode is configured having predetermined length and principal cross sectional dimension;

said control assembly includes an electrical coding component mounted with said support member and exhibiting an electrical parameter corresponding with said predetermined dimension;

said electrosurgical generator includes a decoding circuit electrically coupled with said control assembly, responsive to electrically interrogate said electrical coding component to derive a corresponding selection signal, and is responsive to said selection signal to generate predetermined said first current defined output and second current defined output corresponding with said predetermined dimension.

91. The system of claim 73 in which:

said control assembly includes a temperature sensor mounted upon said support member at said forward end region and having a temperature output condition corresponding with the temperature of tissue in adjacency with it; and said electrosurgical generator includes a temperature logic circuit responsive to said temperature output condition and a predetermined first temperature value condition to derive a first control condition, said electrosurgical generator further including a control logic circuit responsive to said first control condition to modulate said first current defined output in correspondence therewith.

92. The system of claim 73 in which:

said control assembly includes a temperature sensor mounted upon said support member at said forward end region and having a temperature output condition corresponding with the temperature of tissue in adjacency with it; and said electrosurgical generator includes a temperature logic circuit responsive to said temperature output condition and a predetermined second temperature value condition to derive a second control condition, to modulate said second current defined output in correspondence therewith.

93. The system of claim 73 in which:

said control assembly includes a temperature sensor mounted upon said support member at said forward end region and having a temperature output condition corresponding with the temperature of tissue in adjacency with it; and said electrosurgical generator includes a temperature logic circuit responsive to said temperature output condition and a predetermined third temperature value condition corresponding with the necrosis of said abnormal tissue to derive a third control condition, said generator including a control logic circuit responsive to said third control condition to terminate generation of said second current defined output.

94. The system of claim 73 in which:

said control assembly includes a temperature sensor mounted upon said support member at said forward end region and having a temperature output condition corresponding with the temperature of tissue in adjacency with it;

said electrosurgical generator includes:
- a display assembly responsive to a display input signal to provide a perceptible output a procedure termination,
- a temperature logic circuit responsive to said temperature output condition and a predetermined third temperature value condition corresponding with the necrosis of said abnormal tissue to derive a third control condition, and
- a control logic circuit responsive to said third control condition to derive said display input signal.

95. A method for cauterizing tissue of a patient, comprising the steps of:

(a) providing an electrosurgical generator assembly having an electrosurgical return, controllable to generate a first current defined output for carrying out electrosurgical cutting of tissue, and to generate a second current defined output for carrying out the cauterization of said tissue;

(b) providing an instrument electrically coupled with said electrosurgical generator assembly, having a support member extending between a tip and a rear region, having a forward end region with first and second electrode assemblies having a nested orientation for movement of said forward end region with respect to said tissue, actuable for outward, spaced apart deployment from said forward end region to corresponding first and second deployed orientations and further actuable to retract toward said nested orientation;

(c) positioning said instrument forward end region in said tissue with said first and second electrodes in said nested orientation;

(d) actuating said instrument to deploy said first electrode assembly outwardly to a first cauterizing orientation;

(e) simultaneously with said step (d) controlling said electrosurgical generator assembly to apply said first current defined output to said first electrode assembly in electrical association with said return during said first electrode deployment;

(f) actuating said instrument to deploy said second electrode outwardly to a second cauterizing orientation spaced from said first cauterizing orientation;

(g) simultaneously with said step (f), controlling said electrosurgical generator assembly to apply said first current defined output to said second electrode assembly in electrical association with said return during said second electrode assembly deployment;

(h) controlling said electrosurgical generator assembly to apply said second current defined output across said first and second electrode assemblies, for an interval effective to cauterize tissue located substantially therebetween;

(i) actuating said instrument to retract said first electrode assembly toward said nested orientation;

(j) actuating said instrument to retract said second electrode assembly toward said nested orientation; and (k) removing said instrument forward end region from said tissue.

96. The method of claim 95 wherein said steps (d) through (g) are carried out substantially simultaneously.

97. The method of claim 95 in which:

said electrosurgical return is provided as a patient return electrode having an extended surface area for atraumatic contact with tissue at a location remote from said first and second electrodes;

including the step of: positioning said patient return electrode in a skin contacting relationship with said patient, and said steps (e) and (g) are carried out in electrosurgically monopolar fashion.

98. The method of claim 95 in which:

said electrosurgical return is provided comprising a return electrode mounted upon said support member at a location in electrical coupling association with said tissue when said forward end region is positioned in said tissue; and said steps (e) and (g) are carried out in electrosurgically monopolar fashion.

99. The method of claim 98 in which said step (h) is carried out by applying said second current defined output across said first electrode assembly and said return electrode and across said second electrode and said return electrode.

100. The method of claim 99 in which said second current defined output is applied simultaneously across said first and second electrode assemblies and said return electrode.

101. The method of claim 95 in which:

said instrument is provided having a temperature sensor mounted upon said support member at said forward end region and having a temperature output condition corresponding with the temperature of tissue in adjacency with it; and said step (h) application of said second current defined output is carried out until said temperature output condition corresponds with an effective cauterization of said tissue.

102. The method of claim 95 in which:

said steps (d) and (f) are carried out by deploying respective said first and second electrodes to a sequence of incrementally outward said first and second cauterizing orientations from first to last; and said step (h) is carried out following movement of said first and second electrode assemblies to each said incrementally outward orientation from first to last.

103. The method of claim 95 in which:

said instrument is provided having a temperature sensor mounted upon said support member at said forward end region and having a temperature output condition corresponding with the temperature of tissue in adjacency with it; and said steps (e) and (g) include the steps of monitoring said temperature output condition and controlling said electrosurgical generator to maintain the temperature of tissue in contact with said first and second electrodes during said deployment thereof below about 75° C.

104. A method for cauterizing tissue of a patient, comprising the steps of:

(a) providing an electrosurgical generator assembly having an electrosurgical return, controllable to generate a first current defined output for carrying out electrosurgical cutting of tissue, and to generate a second current defined output for carrying out the cauterization of tissue;

(b) providing an instrument electrically coupled with said electrosurgical generator assembly, having a support member extending between a tip and a rear region, having a forward end region with a deployable first electrode assembly having a nested orientation for movement of said forward end region with respect to said tissue, actuable for outward deployment from said forward end region to a cauterizing orientation and further actuable to retract toward said nested orientation, and having a surface mounted electrode in electrical communication with said electrosurgical return mounted upon said support member at a location for electrical coupling association with said tissue;

(c) positioning said instrument forward end region in said tissue with said first electrode assembly in said nested orientation and said surface mounted electrode in said electrical coupling association with said tissue;

(d) actuating said instrument to deploy said first electrode assembly outwardly to said cauterizing orientation;

(e) simultaneously with said step (d), controlling said electrosurgical generator assembly to apply said first current defined output to said first electrode in electrical association with said electrosurgical return through said second electrode during said deployment;

(f) controlling said electrosurgical generator assembly to apply said second current defined output across said first electrode and said surface mounted electrode for an interval effective to cauterize said abnormal tissue;

(g) actuating said instrument to retract said first electrode assembly toward said nested orientation; and (h) removing said instrument forward portion from said tissue.

105. The method of claim 104 in which:

said instrument is provided having a temperature sensor mounted upon said support member at said forward end region and having a temperature output condition corresponding with the temperature of tissue in adjacency with it; and said step (f) application of said second current defined output is carried out until said temperature output condition corresponds with an effective cauterization of said abnormal tissue.

106. The method of claim 104 in which:

said step (d) is carried out by deploying said first electrode assembly to a sequence of incrementally outward cauterizing orientations from first to last; and said step (f) is carried out following movement of said first electrode assembly to each said incrementally outward orientation from first to last.

107. The method of claim 104 in which:

said instrument is provided having a temperature sensor mounted upon said support member at said forward end region and having a temperature output condition corresponding with the temperature of tissue in adjacency with it; and said steps (e) includes the step of monitoring said temperature output condition and controlling said electrosurgical generator assembly to maintain the temperature of said electrode below about 75° C. during said deployment thereof.

* * * * *